(12) United States Patent
Martynow et al.

(10) Patent No.: US 7,897,793 B2
(45) Date of Patent: Mar. 1, 2011

(54) PROCESS FOR PREPARATION OF 13,14-DIHYDRO-PGF2 ALPHA DERIVATIVES

(75) Inventors: Jacek Martynow, Trzcianka (PL); Julita Szyc, Warsaw (PL); Wieslaw Szelejewski, Warsaw (PL); Osman Achmatowicz, Warsaw (PL); Andrzej Kutner, Warsaw (PL); Krzysztof Wiśniewski, Pruszków (PL); Jerzy Winiarski, Warsaw (PL); Oliwia Zegrocka-Stendel, Warsaw (PL); Piotr Golebiewski, Warsaw (PL)

(73) Assignee: Instytut Farmaceutyczny, Warsaw (PL)

( * ) Notice: Subject to any disclaimer, the term of this patent is extended or adjusted under 35 U.S.C. 154(b) by 243 days.

(21) Appl. No.: 11/874,218

(22) Filed: Oct. 18, 2007

(65) Prior Publication Data

US 2008/0207926 A1    Aug. 28, 2008

Related U.S. Application Data

(62) Division of application No. PCT/PL2006/000023, filed on Apr. 18, 2006.

(30) Foreign Application Priority Data

Apr. 18, 2005    (PL)    ..................................... 374461

(51) Int. Cl.
  *C07D 307/93*    (2006.01)
  *C07D 493/00*    (2006.01)
  *C07C 69/74*    (2006.01)

(52) U.S. Cl. ........................ 549/302; 549/351; 560/121

(58) Field of Classification Search .................. 549/302, 549/51, 513; 560/121
  See application file for complete search history.

(56) References Cited

FOREIGN PATENT DOCUMENTS

WO    WO 02/096898 A2 * 12/2002

OTHER PUBLICATIONS

Noyori et al. Angew. Chem. Int. Ed. Engl. 23 (1984) 847-876.*
van Tamelen et al. Proc. Natl. Acad. Sci. USA, (82), 1879-1880, 1985.*

* cited by examiner

*Primary Examiner*—D. Margaret Seaman
*Assistant Examiner*—Nizal S Chandrakumar
(74) *Attorney, Agent, or Firm*—Matthias Scholl, PC; Matthias Scholl

(57) ABSTRACT

The invention relates to a process for the preparation of 13,14-dihydro-PGF$_{2\alpha}$ derivatives of R or S configuration at carbon 15, represented by the general formula (I), wherein the identity of the substituents is defined in the description. Compounds of the formula (I) are valuable biologically-active substances or intermediates in the preparation thereof. The invention especially relates to the process for preparation of 13,14-dihydro-15(R)-17-substituted-18,19,20-trinor-PGF$_{2\alpha}$, i.e., latanoprost.

24 Claims, 4 Drawing Sheets

PROCESS FOR PREPARATION OF 13,14-DIHYDRO-PGF2 ALPHA DERIVATIVES

CROSS-REFERENCE TO RELATED APPLICATIONS

This application is a divisional of International Patent Application No. PCT/PL2006/000023, with an international filing date of Apr. 18, 2006, which is based on Polish Patent Application No. P-374461, filed Apr. 18, 2005. The contents of these specifications are incorporated herein by reference.

BACKGROUND OF THE INVENTION

1. Field of the Invention

This invention relates to 13,14-dihydro-PGF$_{2\alpha}$ derivatives having R or S configuration at the hydroxyl-substituted carbon 12 of the omega chain, and to the processes and intermediates used for the preparation of these biologically-active derivatives. More particularly, the invention relates to the process for preparation of 13,14-dihydro-15(R)-17-substituted-18,19,20-trinor-PGF$_{2\alpha}$, known as latanoprost, which is a pharmaceutically-active compound useful for the reduction of elevated intra-ocular pressure in patients with open angle glaucoma and ocular hypertension.

2. Description of the Related Art

Natural prostaglandins occur at very low concentrations in almost all human tissues and bodily fluids, and play an important role in such conditions as pregnancy, arterial hypertension, osteoporosis, chronic ulcer disease, asthma, and algesia. Some prostaglandins play a role in inflammatory processes and conditions related to myocardial infarction, in arthritis, and influence the incidence of adverse effects of antineoplastic chemotherapy.

Prostaglandins F$_{2\alpha}$ (PGF$_{2\alpha}$) are derived from 7-[3,5-dihydroxy-2-(3-hydroxy-1-octenyl)-cyclopentyl]-5-heptenoic acid, a cyclopentane ring substituted with two hydroxy groups in cis configuration with respect to one another, which further carries two hydrocarbon side chains, alpha and omega, which are trans to one another. In prostaglandins F$_{2\alpha}$ one unsaturated bond is situated between carbons 13 and 14 in the omega chain, and an additional double bond in the cis configuration is situated between carbons 5 and 6 of the alpha chain.

Analogues of PGF$_{2\alpha}$ and their use in the treatment of ocular hypertension and glaucoma are described inter alia in European patent applications EP-A1-0170258, EP-A1-0253094 and EP-A1-0364417. Review of medicines used in glaucoma treatment was undertaken by M. F. Sugrue (J. Med. Chem. 40 (1997), 2793-2809). Among PGF$_{2\alpha}$ analogues, an important therapeutic role plays latanoprost (C. B. Toris et al., Ophtalomology 100 (1993), 1297-1304). Latanoprost, 13,14-dihydro-17-phenyl-18,19,20-trinor-PGF$_{2\alpha}$ isopropyl ester, or (Z)-7-{(1R,2R,3R,5S)-3,5-dihydroxy-2-[(R)-5-phenyl-3-hydroxypentyl]cyclopentyl}-hept-5-enoic acid 2-propyl ester, having saturated omega side chain and esterified carboxylic group, has the following structure

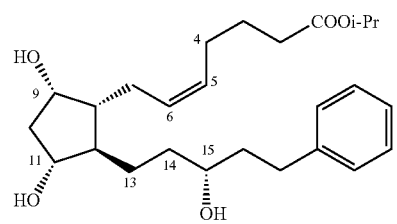

Latanoprost is described, for example, in European patent EP 0364417 B1.

General issues related to chemistry of prostaglandins, including PGF$_{2\alpha}$, are disccused, for example, in monographs in the field of organic chemistry by R. Noyori "Assymetric Catalysis In Organic Chemistry" John Wiley and Sons, Inc., New York, N.Y., 1994, chapter VI; E. J. Corey, X-M. Cheng "The Logic of Chemical Synthesis" John Wiley and Sons, Inc. New York, N.Y., 1989; chapter XI; and J.-H. Fuhrhop, G. Li "Organic Synthesis—Concepts and Methods" Wiley-VCH Verlag GmbH, Weinheim, 2003; Chapter II.

The numbering of the carbon skeleton of prostaglandins, used in the present description, is discussed, e.g., in the monograph of J. H. Fuhrhop, G. Li "Organic Synthesis—Concepts and Methods" Wiley-VCH Verlag GmbH, Weinheim, 2003; Chapter II.

In the synthesis of prostaglandin derivatives, three main strategies are generally used:

a. the Corey method, i.e., the so-called general method of synthesis of prostaglandins (E. J. Corey, X.-M. Cheng "The Logic of chemical Synthesis" John Wiley and Sons, Inc. New York, 1989; chapter XI. E. J. Corey, Angew. Chem. Int. Ed. Engl. 30, (1991), 455), b. the 1,4-addition method (S. Okamoto et al. J. Org. Chem. 53 (1988), 5590; E. J. Corey et al. Tetrahedron Lett. 27 (1986), 2199; C. J. Sih et al. J. Am. Chem. Soc. 97 (1975), 865), and c. the Noyori method, consisting in 1,4-addition with enolate uptake (R. Noyori "Asymetric Catalysis In Organic Chemistry" John Wiley and Sons, Inc. New York, N.Y., 1994; chapter VI).

These three strategies are demonstrated by simplification in FIG. 1.

Among the above-mentioned methods, the most important in practice is the Corey method, consisting in attachment, first, of the omega chain, and then the alpha chain, to an appropriately functionalized synthone of the central cyclopentane ring. This, in turn, is prepared by uncomplicated modifications of Corey (−)-lactone ((2S,3R,4S,5R)-4,5-dihydroxy-hexahydrocyclopenta[b]furan-2'-one).

For example, the synthesis of PGF$_{2\alpha}$ analogue, latanoprost, by the Coreys method comprises a sequence of the following reactions:

a. attachment of omega chain in the form of an enone to a synthone of the cyclopentane ring, e.g., using the Wittig olefination reaction;

b. reduction of the resultant 13,14-en-15-one to the 13,14-en-15-ol;

c. hydrogenation of the unsaturated bond between carbons 13 and 14;

d. attachment of the alpha chain; and, optionally, e. further transformation of the side chains.

According to the above methods, described inter alia in EP 0364417 B1, EP 0544899 B1 and in B. Resul et al., J. Med.

Chem. 36 (1993), p. 243-248 and 2242, a diastereoisomeric mixture of latanoprost and its 15S epimer is obtained from the p-phenylbenzoiloxy-derivative of Corey (−)-lactone. That mixture requires chromatographic resolution.

Two other impurities of latanoprost may include the 15S, 5,6E-isomer and the 15R, 5,6E-isomer.

In view of the regulatory requirements relating to chemical purity of pharmacologically-active substances, especially of ophtalmic substances, there is a necessity to develop improved methods of synthesis of appropriate diastereoisomer of $PGF_{2\alpha}$ derivatives, not only devoid of any residual intermediates and reagents that are used in multi-step synthesis, but also free of any diastereoisomeric byproducts of prostaglandins which may themselves exert biological activity and therapeutic effects.

International Patent Application Publication WO 93/00329 (EP 0544899 B1) resolves the problem of diastereoisomeric purity of latanoprost by partially regioselective hydrogenation of carbonyl group in the omega chain with borohydride and isolation of the desired 15R diastereoisomer of the intermediate alcohol by selective crystallization from diisopropyl ether.

Further improvements of that approach to synthesis of $PGF_{2\alpha}$ derivatives are proposed in the art, consisting in use of more preferable and/or additional hydroxyl protecting groups, or in different order of their introduction and/or removal (WO 01/55101, WO 92/02496, WO02/96898), other, more selective, methods of carbonyl group reduction (WO 02/96868), or methods of double bond reduction in the omega chain (WO 03/037857, U.S. Pat. No. 668,901).

Despite the development of stereoselective methods of generation of an asymmetric center at the position corresponding to the carbonyl carbon of the coupled enone, as described, for example, in the monograph of E. J. Corey, X.-M. Cheng "The Logic of Chemical Synthesis" John Wiley and Sons, Inc. New York, N.Y., 1989, chapter XI; U.S. Pat. No. 6,689,901 patent and publications of J. Hutton, Synthetic Commun. 9 (1979), 483 and M. Node et al. J. Am. Chem. Soc. 122 (2000), 1927-1936, the reduction always results in undesired side formation of a diastereoisomer of the opposite configuration. In practice, it means that the prepared crude compound needs to be purified of the undesired isomer, and this is the more laborious and the more difficult, the greater its amount in the mixture.

In the case of latanoprost, this difficulty is greater because the 15S, 5,6Z isomer is difficult to detect even with use of HPLC analysis due to similar retention times of both isomers (relative value of $R_{F(15S)}=0.95\times R_{F(15R)}$; WO 02/0968989). In practice, this means that preparative separation of 15S, 5,6Z isomer from latanoprost is difficult, both by column chromatography and by preparative HPLC.

Attempts to first introduce into Corey's lactone the omega chain, having in its structure the ready asymmetric center corresponding to the desired 15R configuration, and subsequently, to introduce into the synthone the alpha chain, are described, by way of example of $PGE_3$ and $PGF_{3\alpha}$ analogues, in the publication by E. J. Corey et al., J. Am. Chem. Soc. 93 (1971), 1490. However, due to the low total yield, these methods are not useful on industrial scale.

The strategy of first introducing the omega chain into the (phenylsulfonyl)methyl derivative of Corey's (−)-lactol in the reaction with optically active α-hydroxy-aldehydes, is also used for the preparation of racemic and non-racemic $PGF_{2\alpha}$. From the thus obtained 14,15-dihydroxy-13-sulfone, the sulfonate and the 14-hydroxy group are removed reductively, to give 13,14-alkenes, to which the alpha side chain is then added (B. Achmatowicz et al., Tetrahedron 44 (1988), 4989-98).

Precursors of prostaglandins, having β-hydroxysulfone moiety in the omega chain which is first introduced, are also prepared in the reaction of (phenylsulfonyl)methyl derivative of Corey's (−)-lactol with bases and epoxys. According to Polish patent PL 149389, a hydroxy group in omega chain is then oxidized to a ketone, whereas as the result of sulfone elimination, prostaglandin synthones are prepared, having the omega chain in the form of a 13,14-en-15-one. The use of this strategy in the synthesis of $PGF_{2\alpha}$ derivatives is not practically more advantageous than analogical method of introducing the 13,14-en-15-one in the Wittig reaction, because it requires stereoselective reduction of the carbonyl group and, then, introduction of the alpha chain, presenting the same difficulties as described above.

The strategy based on attaching the alpha chain first and then the omega chain is used in $PGF_{1\alpha}$ and $PGD_2$ synthesis starting from the derivatives of Corey (−)-lactone (T. K. Schaaf, E. J. Corey, J. Org. Chem. 37 (1972), 2921; E. J. Corey et al., J. Am. Chem. Soc. 93 (1971), 4326; E. J. Corey, K. Shimoji, J. Am. Chem. Soc. 105 (1983), 1662). In this way, in the case of PGF derivatives, the 5,6-saturated compounds of 13,14-en-15-one structure are obtained, requiring a reduction of the ketone group of the enone to an allyl alcohol of the 15R configuration. The above process would be burdened with significant difficulties if adapted to the synthesis of $PGF_{2\alpha}$ analogues related to occurrence of the 15S isomer and the need of a stereoselective reduction of the 13,14-alkene in the presence of the 5,6-alkene.

BRIEF SUMMARY OF THE INVENTION

The search for a stereoselective and practical method of preparation of 13,14-dihydro-$PGF_{2\alpha}$ derivatives lead to an attempt to introduce into Corey (−)-lactone the omega chain of the target prostaglandin having a desired asymmetric configuration at the hydroxy-substituted carbon. This process would eliminate the need for a regioselective reduction of the enone moiety and for separation of undesired regioisomers from the final product.

This aim has been realized in certain embodiments according to the invention, in which the alpha chain was first introduced into the starting derivative of Corey (−)-lactone, and subsequently, the omega chain of the target derivative of $F_{2\alpha}$ prostaglandin was attached having a chiral center at the hydroxyl-substituted carbon. The process according to the invention provides derivatives of 13,14-dihydro-$PGF_{2\alpha}$ of high diastereoisomeric excess of the desired isomer of R or S configuration, respectively, at the hydroxy-substituted carbon. This process allows particularly for the preparation of 13,14-dihydro-15(R)-17-substituted-18,19,20-trinor-$PGF_{2\alpha}$ derivatives of high diastereoisomeric excess.

The invention further provides a process for the preparation of prostaglandin $F_{2\alpha}$ derivatives having an R or S configuration at the hydroxy-substituted carbon of the omega chain of high diastereoisomeric excess, represented by the general formula (VIII),

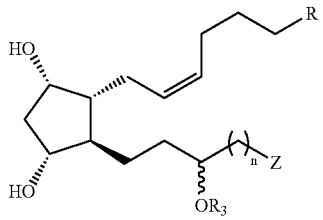

(VIII)

wherein:

R represents COOH or COOY,

Y is $C_{1-6}$-alkyl, alkylphenyl or phenyl, optionally substituted by $C_{1-3}$-alkyl;

Z represents H, methyl or phenyl, optionally substituted by $C_{1-3}$-alkyl, $C_{1-3}$-alkoxy or at least one halogen atom;

$R_3$ represents H or a hydroxyl protecting group, and n represents an integer from 0 to 6;

the process comprising the steps of:

(a) generating an anion of the sulfone of formula (V) at the α position in relation to the sulfonyl group

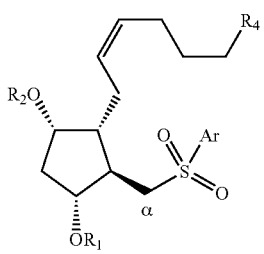

(V)

wherein $R_1$ and $R_2$, independently, represent a hydroxyl protecting group;

Ar represents substituted or unsubstituted aryl or heteroaryl containing at least one heteroatom selected from the group consisting of O, N, P and S atoms;

$R_4$ is an orthoester group represented by the general formula —$C(OR_6)_3$ or by the general formula (Va),

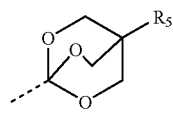

(Va)

$R_5$ represents H, substituted or unsubstituted $C_1$-$C_6$-alkyl or Ar; and $R_6$ is substituted or unsubstituted $C_1$-$C_{10}$-alkyl or aryl;

(b) reacting the anion generated in step (a) with an alkylating agent of the general formula (VI),

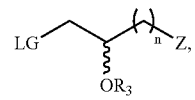

(VI)

to yield a compound of the general formula (VII)

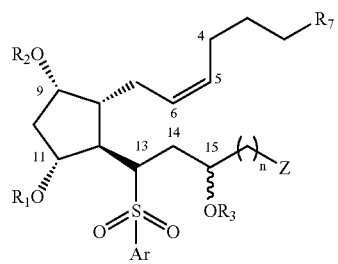

(VII)

wherein

LG represents a leaving group, and $R_3$ represents a hydroxyl protecting group; or LG and $R_3$ represent a chemical bond and/or taken together with the atoms to which they are attached and with an —S(O)— or an —$SO_2$— group form a cyclosulfite or a cyclosulfate; or LG and $R_3$ represent chemical bonds and/or taken together with the atoms to which they are attached form an epoxide;

the chiral configuration at the hydroxy-substituted carbon of the alkylating agent corresponds to the chiral configuration of the target prostaglandin;

$R_7$ is —C(=O)—$OR_8$, —$CH_2$—$C(CH_2OH)_2$—$R_5$, or an orthoester group represented by the general formula —$C(OR_6)_3$ or by the general formula (Va),

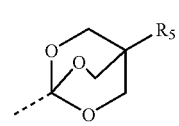

(Va)

$R_5$ represents H, substituted or unsubstituted $C_1$-$C_6$-alkyl or Ar; and $R_6$ is substituted or unsubstituted $C_1$-$C_{10}$-alkyl or aryl;

$R_8$ represents H, substituted or unsubstituted $C_{1-10}$-alkyl or phenyl;

Z represents H, methyl or phenyl, optionally substituted by $C_{1-3}$-alkyl, $C_{1-3}$-alkoxy or at least one halogen atom;

n represents an integer from 0 to 6;

$R_1$ and $R_2$, independently, represent a hydroxyl protecting group; and

Ar represents substituted or unsubstituted aryl or heteroaryl containing at least one heteroatom selected from the group consisting of O, N, P and S atoms;

(c) reductively desulfonating the compound of the general formula (VII) obtained in step (b) to yield the compound of the general formula (VIIa)

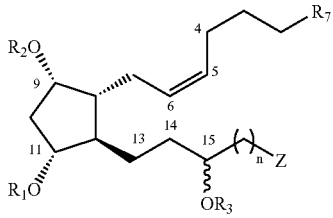

(VIIa)

wherein $R_1$, $R_2$ and $R_3$, independently, represent a hydroxyl protecting group;

$R_7$ is —C(=O)—$OR_8$, —$CH_2$—C($CH_2OH$)$_2$—$R_5$, or an orthoester group represented by the general formula —C($OR_6$)$_3$ or by the general formula (Va),

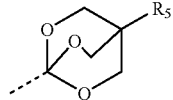

(Va)

$R_5$ represents H, substituted or unsubstituted $C_1$-$C_6$-alkyl or Ar; and $R_6$ is substituted or unsubstituted $C_1$-$C_{10}$-alkyl or aryl;

$R_8$ represents H, substituted or unsubstituted $C_{1-10}$-alkyl or phenyl; Ar represents substituted or unsubstituted aryl or heteroaryl containing at least one heteroatom selected from the group consisting of O, N, P and S atoms;

n represents an integer from 0 to 6; and

Z represents H, methyl or phenyl, optionally substituted by $C_{1-3}$-alkyl, $C_{1-3}$-alkoxy or at least one halogen atom;

(d) removing the hydroxyl protecting groups from the compound of the general formula (VIIa) to yield the compound of formula (VIIb)

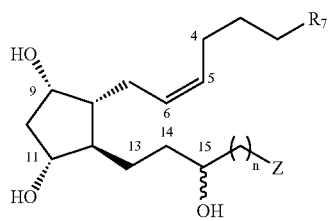

(VIIb)

wherein $R_7$ is —C(=O)—$OR_8$, —$CH_2$—C($CH_2OH$)$_2$—$R_5$, or an orthoester group represented by the general formula —C($OR_6$)$_3$ or by the general formula (Va),

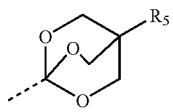

(Va)

$R_5$ represents H, substituted or unsubstituted $C_1$-$C_6$-alkyl or Ar; and $R_6$ is substituted or unsubstituted $C_1$-$C_{10}$-alkyl or aryl;

$R_8$ represents H, substituted or unsubstituted $C_{1-10}$-alkyl or phenyl;

Ar represents substituted or unsubstituted aryl or heteroaryl containing at least one heteroatom selected from the group consisting of O, N, P and S atoms;

n represents an integer from 0 to 6; and

Z represents H, methyl or phenyl, optionally substituted by $C_{1-3}$-alkyl, $C_{1-3}$-alkoxy or at least one halogen atom;

(e) converting the compound of formula (VIIb) obtained in step (d) to a compound of the general formula (VIII);

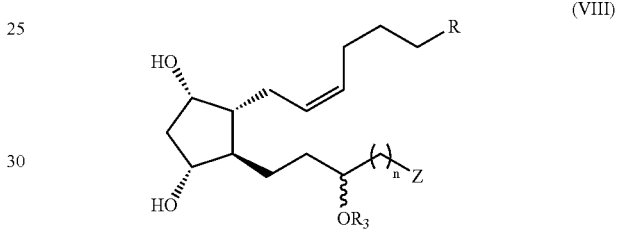

(VIII)

wherein

R represents COOH;

$R_3$ represents H;

n represents an integer from 0 to 6; and

Z represents H, methyl or phenyl, optionally substituted by $C_{1-3}$-alkyl, $C_{1-3}$-alkoxy or at least one halogen atom; and (f) optionally, esterifying the compound of formula (VIII) obtained at step (e) to yield the compound of formula (VIII), wherein R represents COOY, Y is $C_{1-6}$-alkyl, alkylphenyl or phenyl, optionally substituted by $C_{1-3}$-alkyl;

Z represents H, methyl or phenyl, optionally substituted by $C_{1-3}$-alkyl or $C_{1-3}$-alkoxy or at least one halogen atom; and n represents an integer from 0 to 6.

In other aspects, the invention also provides a compound, used in the above process, represented by the general formula (V)

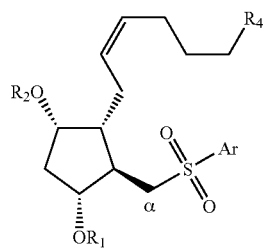

(V)

wherein

R$_1$ and R$_2$, independently, represent H or a hydroxyl protecting group;

Ar represents a substituted or an unsubstituted aryl or heteroaryl containing at least one heteroatom selected from the group consisting of O, N, P and S atoms;

R$_4$ is an orthoester represented by the general formula —C(OR$_6$)$_3$ or by the general formula (Va),

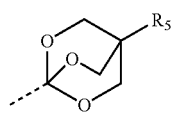
(Va)

R$_5$ represents H, substituted or unsubstituted C$_1$-C$_6$-alkyl or an Ar; and R$_6$ is a substituted or an unsubstituted C$_1$-C$_{10}$-alkyl, or Ar.

In other aspects, the invention also provides a compound, used in the above process, represented by the general formula (V)

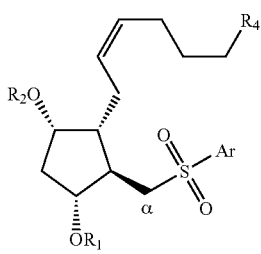
(V)

wherein

R$_1$ and R$_2$, independently, represent H or a hydroxyl protecting group;

Ar represents a substituted or an unsubstituted aryl or heteroaryl containing at least one heteroatom selected from the group consisting of O, N, P and S atoms;

R$_4$ is an orthoester represented by the general formula —C(OR$_6$)$_3$ or by the general formula (Va),

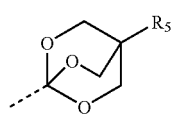
(Va)

R$_5$ represents H, substituted or unsubstituted C$_1$-C$_6$-alkyl or Ar; and

R$_6$ is a substituted or an unsubstituted C$_1$-C$_{10}$-alkyl or Ar.

In other aspects, the invention provides a process for preparation of the compound of the general formula (V)

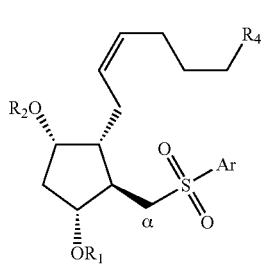
(V)

wherein

R$_1$ and R$_2$, independently, represent H or a hydroxyl protecting group;

Ar represents a substituted or an unsubstituted aryl or heteroaryl containing at least one heteroatom selected from the group consisting of O, N, P and S atoms;

R$_4$ is an orthoester represented by the general formula —C(OR$_6$)$_3$ or by the general formula (Va),

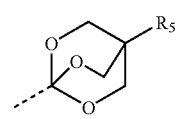
(Va)

R$_5$ represents H, substituted or unsubstituted C$_1$-C$_6$-alkyl or Ar; and

R$_6$ is a substituted or an unsubstituted C$_1$-C$_{10}$-alkyl or Ar;

the process comprising the steps of:

(a) converting a derivative of Corey (−)-lactone of the general formula (I) to a sulfide of the general formula (II)

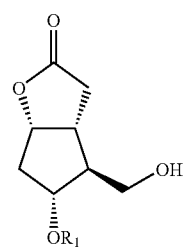
(I)

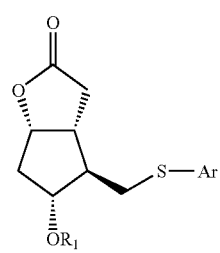
(II)

wherein

R$_1$ represents H or a hydroxyl protecting group; and

Ar represents a substituted or an unsubstituted aryl or heteroaryl containing at least one heteroatom selected from the group consisting of O, N, P and S atoms;

(b) selectively oxidizing the sulfide of the general formula (II) to a sulfone of the general formula (III);

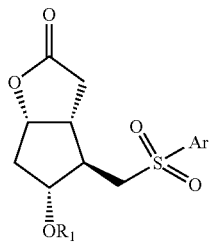
(III)

wherein
$R_1$ represents H or a hydroxyl protecting group; and
Ar represents a substituted or an unsubstituted aryl or heteroaryl containing at least one heteroatom selected from the group consisting of O, N, P and S atoms;

(c) reducing the carbonyl group of sulfone of formula (III) and isolating the derivative of lactol of formula (IV) having a desired configuration at the reduced carbon (depending on the desired configuration of the final prostaglandin derivative)

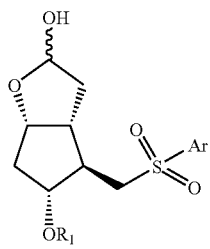
(IV)

wherein
$R_1$ represents H or a hydroxyl protecting group;
Ar represents a substituted or an unsubstituted aryl or heteroaryl containing at least one heteroatom selected from the group consisting of O, N, P and S atoms;

(d) reacting the lactol of formula (IV) in a Wittig reaction with a precursor of the alpha side chain of the target prostaglandin to yield a compound of the general formula (V)

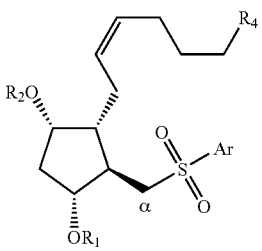
(V)

wherein
$R_1$ represents H or a hydroxyl protecting group;
$R_2$ represents H;
Ar represents a substituted or an unsubstituted aryl or heteroaryl containing at least one heteroatom selected from the group consisting of O, N, P and S atoms;

$R_4$ is an orthoester represented by the general formula $—C(OR_6)_3$ or by the general formula (Va),

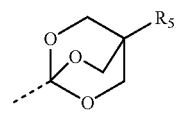
(Va)

$R_5$ represents H, substituted or unsubstituted $C_1$-$C_6$-alkyl or Ar; and
$R_6$ is a substituted or an unsubstituted $C_1$-$C_{10}$-alkyl or Ar;

(e) isolating the compound of the general formula (V), and
(f) optionally, protecting the hydroxyl group $—OR_2$.

In other aspects, the invention provides novel precursors of a synthone of the omega side chain of $PGF_{2\alpha}$, having an R or S configuration at the hydroxy-substituted carbon, represented by the general formula (VI)

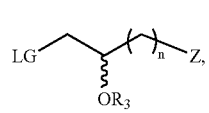
(VI)

wherein
LG represents a halogen, an alkylsulfonyloxy, an alkylarylsulfonyloxy, or a arylsulfonyloxy group, and $R_3$ represents H or a hydroxyl protecting group; or LG and $R_3$ represent a chemical bond and/or taken together with the atoms to which they are attached and with an $—S(O)—$ or an $—SO_2—$ group form a cyclosulfite or a cyclosulfate; or LG and $R_3$ represent chemical bonds and/or taken together with the atoms to which they are attached form an epoxide;

Z represents H, methyl or phenyl, optionally substituted by $C_{1-3}$-alkyl, $C_{1-3}$-alkoxy or at least one halogen atom; and
n represents an integer from 0 to 6.

Preferred novel compounds of formula (VI) are those, in which LG represents an iodine or a bromine atom or p-toluenesulfonyloxy group, and $R_3$ represents a hydroxyl protecting group.

In certain classes of this embodiment, the novel compounds of formula (VI) have an S configuration at the hydroxyl-substituted carbon.

In other aspects, the invention provides processes for the preparation of the compounds of the general formula (VI), having an R or S configuration at the hydroxyl-substituted carbon, and particularly compounds of the general formula (VI) having a high enantiomeric excess.

In other aspects, invention provides intermediates prepared in the process for preparation of the 13,14-dihydroxy-derivatives of $PGF_{2\alpha}$ according to the invention.

One group of novel compounds are those represented by the general formula (VII)

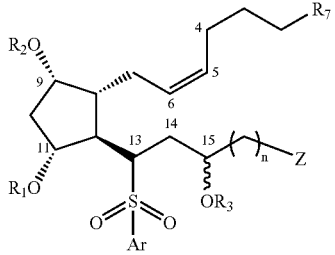

(VII)

wherein $R_1$, $R_2$ and $R_3$, independently, represent a hydroxyl protecting group;

$R_7$ is —C(=O)—$OR_8$, —$CH_2$—C($CH_2OH$)$_2$—$R_5$, or an orthoester group represented by the general formula —C($OR_6$)$_3$ or by the general formula (Va),

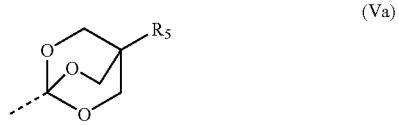

(Va)

$R_5$ represents H, substituted or unsubstituted $C_1$-$C_6$-alkyl or Ar; and $R_6$ is a substituted or an unsubstituted $C_1$-$C_{10}$-alkyl or Ar;

$R_8$ represents H, a substituted or an unsubstituted $C_{1-10}$-alkyl, phenyl, or —$CH_2$—C—($CH_2OH$)$_2$—$R_5$;

Z represents H, methyl or phenyl, optionally substituted by $C_{1-3}$-alkyl, $C_{1-3}$-alkoxy or at least one halogen atom;

n represents an integer from 0 to 6;

Ar represents substituted or unsubstituted aryl or heteroaryl containing at least one heteroatom selected from the group consisting of O, N, P and S atoms;

Another group of novel compounds are those compounds represented by the general formula (VIIa)

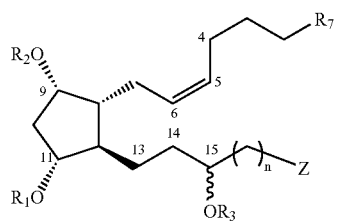

(VIIa)

wherein $R_1$ $R_2$ and $R_3$, independently, represent H or a hydroxyl protecting group;

$R_7$ is —C(=O)—$OR_8$, —$CH_2$—C($CH_2OH$)$_2$—$R_5$, or an orthoester group represented by the general formula —C($OR_6$)$_3$ or by the general formula (Va),

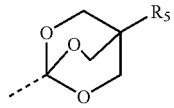

(Va)

$R_5$ represents H, substituted or unsubstituted $C_1$-$C_6$-alkyl or Ar; and $R_6$ is substituted or unsubstituted $C_1$-$C_{10}$-alkyl or Ar;

$R_8$ represents H, substituted or unsubstituted $C_{1-10}$-alkyl, phenyl, or —$CH_2$—C($CH_2OH$)$_2$—$R_5$ group;

n represents an integer from 0 to 6;

Ar represents substituted or unsubstituted aryl or heteroaryl containing at least one heteroatom selected from the group consisting of O, N, P and S atoms; and Z represents H, methyl or phenyl, optionally substituted by $C_{1-3}$-alkyl, $C_{1-3}$-alkoxy or at least one halogen atom.

DETAILED DESCRIPTION OF THE INVENTION

Figure 1:
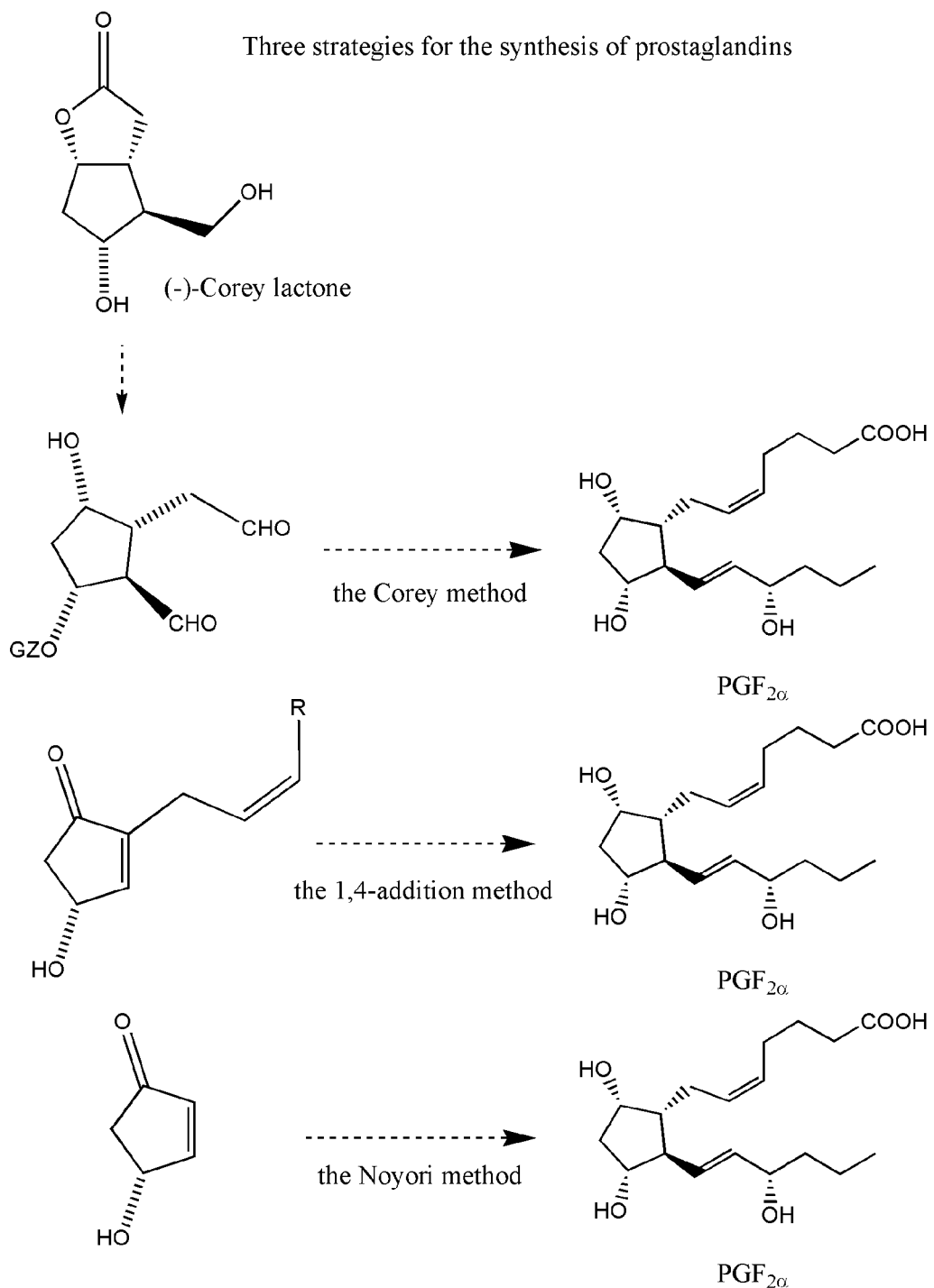
FIG. 1 is an illustration of the known strategies for the preparation of prostaglandins.

Starting compound in the process for preparation of derivatives of 13,14-dihydro-F$_{2\alpha}$ prostaglandins, is a sulfone of the general formula (V)

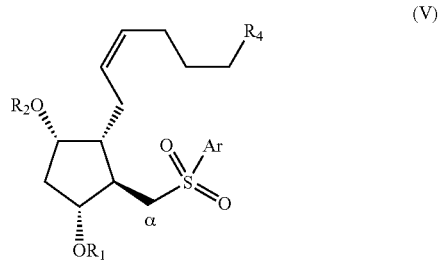

(V)

wherein $R_1$ and $R_2$, independently, represent H or hydroxyl protecting group;

Ar represents a substituted or an unsubstituted aryl or heteroaryl containing at least one heteroatom selected from the group consisting of O, N, P and S atoms;

$R_4$ is an orthoester represented by the general formula —C($OR_6$)$_3$ or by the general formula (Va),

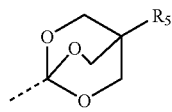

(Va)

R₅ represents H, a substituted or an unsubstituted $C_1$-$C_6$-alkyl or Ar; and

R₆ is a substituted or an unsubstituted $C_1$-$C_{10}$-alkyl or Ar.

The term "aryl" used hereby with reference to Ar group means phenyl group, naphthyl group or 9,10-methaneanthracen-(10H)-yl group, each of them may be optionally substituted by one or more of the following substituents: halogen, $C_{1-4}$-alkyl or alkoxyl.

The term "heteroaryl" used hereby with reference to Ar group means aromatic five- or six-membered group, containing at least one heteroatom selected from the group including oxygen, phosphorus and sulfur, such as thienyl, furanyl, pyrrolil, pyridinyl, pyridazil, quinolinyl, indolyl, imidazolyl, oxazolyl, izoxazolyl, benzofuranyl, benzo[b]thienyl and the like.

The term "alkyl group" used hereby, unless otherwise specified, means straight or branched hydrocarbon group, containing detailed number of carbon atoms.

Unless otherwise specified, each alkyl group, aryl group or heteroaryl group may be optionally substituted by one or more of the following substituents: halogen, $C_{1-4}$-alkyl, $C_{1-4}$-alkoxyl or nitro group.

Hydroxy groups in the starting compound (V) are protected by introduction of protecting groups, which may be the same or different at each occurrence.

Introduction and removing of groups protecting hydroxy groups is well known in the art of organic synthesis (T. W. Greene, P. G. M. Wuts "Protective Groups in Organic Synthesis", ed. 3, John Wiley and Sons, Inc., New York, N.Y., 1999; P. J. Kocienski "Protecting Groups", Georg Thieme Verlag, Stuttgart, 1994; J. March, Advanced Organic Chemistry", John Wiley and Sons, New York, N.Y., 1982).

In the processes of the invention, typical protecting groups are independently used, of sufficient stability in the presence of bases and acids, such as alkyl or arylsilyl groups, alkyl and arylcarbonyl groups (ester groups); acyl groups; alkylaminocarbonyl (carbamate) groups; alkyl groups; alkoxy groups and other.

Silyl groups are trialkylsilyl groups, dialkylarylsilyl groups, alkyldiarylsilyl groups, triarylsilyl groups, such as, for example, trimethylsilyl, triethylsilyl, t-butyldimethylsilyl, t-butyldiphenylsilyl, triphenylsilyl. Acyl groups include alkanoyl groups and carboxyalkanoyl groups, having 1 to 6 carbon atoms, such as an acetate group. Typical alkoxyalkyl groups are, for example, methoxymethyl, ethoxymethyl, tetrahydrofuranyl, and tetrahydropyranyl.

Carboxyl group in the starting compound (V) is protected, for example, in the form of orthoester group, or oxabicyclo [2.2.2]octane group (OBO).

Use of orthoesters and oxabicyclo[2.2.2]octane group as protecting carboxyl group is generally discussed in the monograph of T. W. Greene, P. G. M. Wuts "Protective Groups in Organic Synthesis", 3 ed., John Wiley and Sons, Inc. New York, N.Y., 1999; chapter V, and in the publication of U. Pindur; J. Mueller, C. Filo, H. Witzell Chem. Soc. Rev. 1987, 75. However, there are few examples of oxabicycleoctane group use in the art of prostaglandin synthesis (G. H. Verdoorn et al. South African Journal of Chemistry 40 (1987), 134-8; E. J. Corey, X.-M. Cheng "The Logic of Chemical Synthesis" John Wiley and Sons, Inc., New York, N.Y., 1989; chapter XI), due to the limited stability of the oxabicyclooctane moiety under acidic conditions. The compounds of the 4-methyl-2,6,7-trioxabicyclo[2.2.2]octane structure easily hydrolyze to the corresponding 2,2-bis(hydroxymethyl)-1-propyl esters, which may be then converted into other esters, for example, alkyl esters, into salts of corresponding acids or into corresponding carboxylic acids (P. J. Kocienski "Protecting Groups", Georg Thieme Verlag, Stuttgart, 1994; T. W. Greene, P. G. M. Wuts "Protective Groups in Organic Synthesis", $3^{rd}$ ed., John Wiley and Sons, Inc., New York, N.Y., 1999; J. March "advanced Organic Chemistry" John Wiley and Sons, New York, N.Y., 1992). In the suitably selected conditions, 4-alkyl-2,6,7-trioxabicyclo[2.2.2]octane groups and other orthoesters are very useful carboxyl protecting groups, especially under basic conditions.

Methods of alkylation of compound containing active methylene groups, such as (arylsulfonyl)methyl group, with use of alkyl sulfonates or alkyl halides, are discussed, for example, in the monograph of H. O. House "Modern Synthetic Reactions", W. A. Benjamin, Inc., Menlo Park, Calif., USA, 1972; Chapter 9. Activation of such group (generation of stabilized carbanion —CH—$SO_2$—Ar) is known in the art and proceeds under the influence of bases: P. E. Magnus, Tetrahedron 33 (1977), 2019; B. M. Trost Bull. Chem. Soc. Jpn. 61 (1988), 107; N. S. Simpkins Tetrahedron 46 (1990), 6951. Bases used for generating carbanions stabilized by (arylsulfonyl)methyl group are, for example, butyllithium or lithium hexamethyldisilazide (lithium bis(trimethylsilyl) amide (LiHMDS), $Me_3$—Si—N(Li)—Si—$Me_3$), cited, for example, in I. R. Baldwin, R. J. Whitby Chem. Commun. (2003), 2786-2787.

In a preferred embodiment of the invention, a sulfone anion of the general formula (V) is generated in situ, with the use of a strong organic base, for example, metal bis(trimethylsilyl) amide, and preferably lithium bis(trimethylsilyl)amide, in a non-aqueous solvent.

Activation of sulfone (V) allows its effective alkylation with use of an alkylating agent of the general formula (VI) of an R or S configuration at the hydroxy-substituted carbon atom,

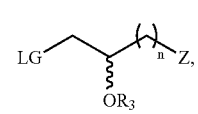

(VI)

wherein

LG represents a halogen, an alkylsulfonyloxy, an alkylarylsulfonyloxy, or a arylsulfonyloxy group, and R₃ represents H or a hydroxyl protecting group; or LG and R₃ represent a chemical bond and/or taken together with the atoms to which they are attached and with an —S(O)— or an —$SO_2$— group form a cyclosulfite or a cyclosulfate; or LG and R₃ represent a chemical bond and/or taken together with the atoms to which they are attached form an epoxide;

Z represents H, methyl or phenyl, optionally substituted by $C_{1-3}$-alkyl, $C_{1-3}$-alkoxy or at least one halogen atom; and n represents an integer from 0 to 6.

A good leaving group LG in the compound (VI) is a halogen atom, such as iodine, bromine, chlorine, fluorine; alkylsulfonyloxy, alkylarylsulfonyloxy, or arylsulfonyl group, such as benzenesulfonyl, p-toluenesulfonyl, methanesulfonyl, trifluoromethanesulfonyl, alkylsulfonyl, substituted alkylsulfonyl, naphthylsulfonyl, substituted phenylsulfonyl, chlorosulfonyl, substituted naphthylsulfonyl, or another group easily leaving with an electron pair, such as, for example, an oxygen atom of an epoxy ring.

The alkylation reaction employs, in step (b), a compound of the general formula (VI) having an R or S configuration at the hydroxy-substituted carbon in a high enantiomeric excess, matching the configuration of the corresponding target prostaglandin of formula (VIII). The enantiomeric excess is defined according to the definition in the monograph of E. L. Eliel; S. H. Wilen; L. N. Mander "Stereochemistry of Organic Compounds" John Wiley and Sons, Inc. Preferably, the compound (VI) having an enantiomeric excess above 99% is used, more preferably, above 99.5%.

In the process according to the invention, preferred alkylating agents are those, in which LG represents an iodine atom, a bromine atom, or a p-toluenesulfonyloxy group, and $R_3$ represents a hydroxyl protecting group.

Preferably, in the compounds of the general formula (VI) the $R_3$ group is —Si(R)$_9$(R$_{10}$)(R$_{11}$), wherein $R_9$, $R_{10}$, and $R_{11}$ are the same or different and independently and at each occurrence represent a $C_1$-$C_6$-alkyl or a phenyl.

The alkylation in step (b) yields a compound of the general formula (VII) having an (R) or (S) configuration at the hydroxy-substituted carbon,

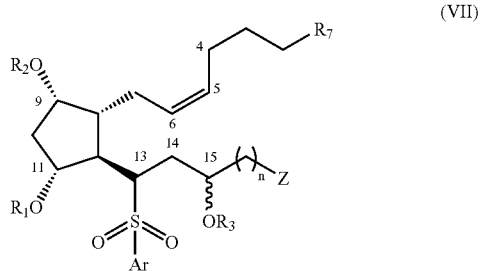

(VII)

wherein $R_1$, $R_2$ and $R_3$, independently, represent a hydroxyl protecting group;

$R_7$ is —C(=O)—OR$_8$, —CH$_2$—C(CH$_2$OH)$_2$—R$_5$, or an orthoester group represented by the formula —C(OR$_6$)$_3$ or by the general formula (Va),

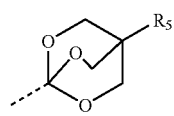

(Va)

$R_5$ represents H, a substituted or an unsubstituted $C_1$-$C_6$-alkyl or Ar; and $R_6$ is a substituted or an unsubstituted $C_1$-$C_{10}$-alkyl or Ar;

$R_8$ represents H, a substituted or an unsubstituted $C_{1-10}$-alkyl, a phenyl, or —CH$_2$—C(CH$_2$OH)$_2$—R$_5$;

Z represents H, a methyl, or a phenyl, optionally substituted by $C_{1-3}$-alkyl, $C_{1-3}$-alkoxy or at least one halogen atom;

n represents an integer from 0 to 6;

Ar represents substituted or unsubstituted aryl or heteroaryl containing at least one heteroatom selected from the group consisting of O, N, P and S atoms;

In step (c), a compound of the general formula (VIII) is subjected to a selective desulfonation to yield a compound of the general formula (VIIa)

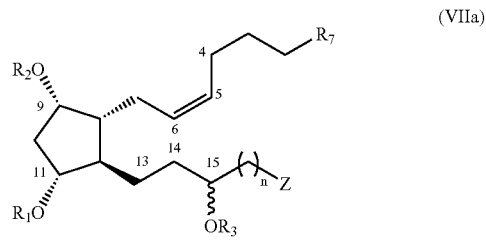

(VIIa)

wherein $R_1$ $R_2$ and $R_3$, independently, represent H or a hydroxyl protecting group;

$R_7$ is —C(=O)—OR$_8$, —CH$_2$—C(CH$_2$OH)$_2$—R$_5$, or an orthoester group represented by the general formula —C(OR$_6$)$_3$ or by the general formula (Va),

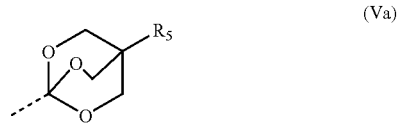

(Va)

$R_5$ represents H, substituted or unsubstituted $C_1$-$C_6$-alkyl or Ar; and $R_6$ is a substituted or an unsubstituted $C_1$-$C_{10}$-alkyl or Ar;

$R_8$ represents H, a substituted or an unsubstituted $C_{1-10}$-alkyl, a phenyl, or —CH$_2$—C(CH$_2$OH)$_2$—R$_5$ group;

Ar represents substituted or unsubstituted aryl or heteroaryl containing at least one heteroatom selected from the group consisting of O, N, P and S atoms;

n represents an integer from 0 to 6; and

Z represents H, methyl or phenyl, optionally substituted by $C_{1-3}$-alkyl, $C_{1-3}$-alkoxy or at least one halogen atom.

Arylsulfonate group may be reductively removed from the substituted (arylsulfonyl)alkanes under various conditions, depending on the structure of the starting compound (Y. Liu, Y. Zhang, Org. Prep. Proc. Int. 33 (2001), 372). Among general methods, reduction with use of dissolving metals in liquid ammonia should be mentioned (e.g., J. R. Hwu et al., J. Org. Chem. 61 (1996), 1493-1499); reduction with use of Mg/MeOH or Mg/EtOH+HgCl$_2$ (G. H. Lee et al., Tetrahedron Lett. 34 (1993), 4541-2; A. C. Brown, L. A. Carpino, J. Org. Chem. 50 (1985), 1749-50), and reduction with use of sodium amalgam in MeOH and Na$_2$HPO$_4$ buffering conditions (B. M. Trost et al., Tetrahedron Lett. 17 (1976), 3477-8). In the reactions of reductive desulfonation, alkene by-products may be generated via elimination of ArS(O)OH (B. M. Trost et al., Tetrahedron Lett. 17 (1976), 3477-8).

In the preferred embodiment of the invention, reductive desulfonation is carried out with use of sodium amalgam (Na/Hg).

In step (d), the hydroxy groups of the thus obtained compound (VIIa) are deprotected, by the method known to those skilled in the art, to give a compound of the general formula (VIIb)

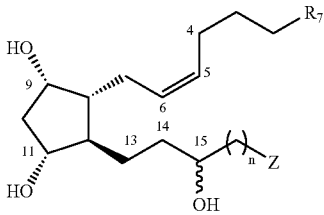

wherein $R_7$ is —C(=O)—$OR_8$, —$CH_2$—C($CH_2OH$)$_2$—$R_5$, or an orthoester group represented by the general formula —C($OR_6$)$_3$ or by the general formula (Va),

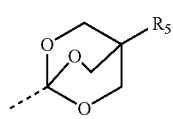

$R_5$ represents H, substituted or unsubstituted $C_1$-$C_6$-alkyl or Ar; and $R_6$ is substituted or unsubstituted $C_1$-$C_{10}$-alkyl or aryl;

$R_8$ represents H, substituted or unsubstituted $C_{1-10}$-alkyl or phenyl;

Ar represents substituted or unsubstituted aryl or heteroaryl containing at least one heteroatom selected from the group consisting of O, N, P and S atoms;

n represents an integer from 0 to 6; and

Z represents H, methyl or phenyl, optionally substituted by $C_{1-3}$-alkyl, $C_{1-3}$-alkoxy or at least one halogen atom;

Deprotection of the hydroxy groups is carried out, depending on the type of protecting groups used, in acidic or basic conditions. The silyl groups are removed, for example, in acidic conditions by the use of protonic acid solutions or their salts with organic bases, in organic solvents, such as THF or acetone, optionally in the presence of water.

The removal of hydroxyl protecting groups under acidic conditions in the processes according to the invention is accompanied by the hydrolysis of the orthoester or ester ($R_7$) group to a carboxyl group.

If needed, the protecting group from the $R_7$ substituent may be removed in step (e) by the use of a strong base solution, for example, lithium hydroxide in the mixture of solvents, such as methanol, ethanol, THF, dioxane and/or water.

In certain embodiments, the reactions carried out in the process of the invention yield 13,14-dihydro-PGF$_{2\alpha}$ represented by formula (VIII),

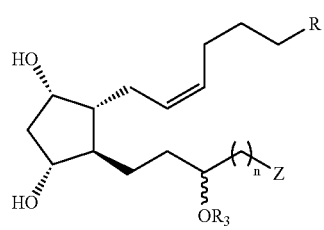

wherein:

R represents COOH,

Z represents H, methyl or phenyl, optionally substituted by $C_{1-3}$-alkyl, $C_{1-3}$-alkoxy or at least one halogen atom;

$R_3$ represents H, and n represents an integer from 0 to 6;

characterized by high diastereomeric excess (defined according to the monograph of E. L. Eliel; S. H. Wilen; L. N. Mander "Stereochemistry of Organic Compounds" John Wiley and Sons, Inc., New York, N.Y., 1994), exceeding 99%, and preferably exceeding 99.5%.

Then, a carboxyl group of the thus obtained compound of the general formula (VIII) is esterified, to give the compound (VIII), in which R represents COOY; Y represents a $C_{1-6}$-alkyl, an alkylphenyl or a phenyl, optionally substituted by $C_{1-3}$-alkyl groups; Z represents H, a methyl or a phenyl, optionally substituted by $C_{1-3}$-alkyl groups or $C_{1-3}$-alkoxy groups or at least one halogen atom; and n represents an integer from 0 to 6.

Steps (e) and (f) according to the invention may be carried out simultaneously, if a salt of an acid of formula (VIII) is used directly for the reaction with the esterifying agent, and Y represents a metal cation or a quaternary ammonium cation.

The esterification reaction is carried out according to the methods known for those skilled in the art of chemistry of PGF$_{2\alpha}$ derivatives, for example, according to the method described in the publication of B. Resul et al., J. Med. Chem. 36 (1993), 243-248 or in International Patent Application publications WO 92/02496; WO 93/00329; WO 01/55101; WO 01/87816; WO 02/096868. Typical esterifying agents are alkyl or phenyl halides and sulfonates. The reaction is carried out in non-aqueous solvents, preferably in aprotic non-aqueous solvents.

In certain embodiments, a process according to the invention allows for the preparation of PGF$_{2\alpha}$ derivatives of high diastereomeric excess of a desired isomer of R or S configuration at the hydroxy-substituted carbon atom in the omega chain, by a method comprising an addition of the synthone of the alpha chain first, and then the synthone of the omega chain, to synthone derivative of Corey (−)-lactone. Optical purity of the product obtained depends on the optical purity of the starting compound of formula (VI), used in the process.

In the preferred embodiment, the process according to the invention is employed for the preparation of latanoprost of high diastereomeric excess and advantageous profile of by-products and impurities. Contrary to processes known in the art, purification of latanoprost prepared in the process according to the invention is relatively simple, due to a very low content of the undesired 15S, 5,6Z diastereoisomer of latanoprost, which depends on controllable degree of optical purity of compounds of formula (VI). In this way, difficulties related to use of preparative HPLC are avoided.

In the process according to the invention, the starting compounds of formula (V) are prepared from Corey (−)-lactone-protected derivatives.

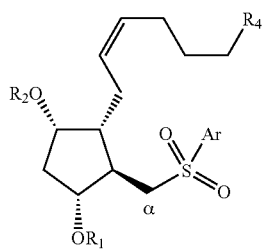

(V)

wherein $R_1$ and $R_2$, independently, represent H or a hydroxyl protecting group; Ar represents a substituted or an unsubstituted aryl or heteroaryl containing at least one heteroatom selected from the group consisting of O, N, P and S atoms;

$R_4$ is an orthoester represented by the general formula —$C(OR_6)_3$ or by the general formula (Va),

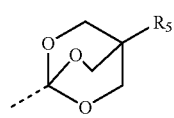

(Va)

$R_5$ represents H, substituted or unsubstituted $C_1$-$C_6$-alkyl or Ar; and $R_6$ is a substituted or an unsubstituted $C_1$-$C_{10}$-alkyl or Ar.

The process for preparation of compounds of formula (V) is characterized in that in comprised the following steps:

(a) converting a derivative of Corey (−)-lactone of the general formula (I) to a sulfide of the general formula (II)

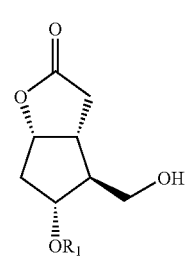

(I)

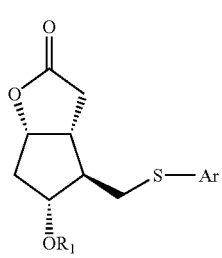

(II)

wherein $R_1$ represents H or a hydroxyl protecting group; and

Ar represents a substituted or an unsubstituted aryl or heteroaryl containing at least one heteroatom selected from the group consisting of O, N, P and S atoms;

(b) selectively oxidizing the sulfide of the general formula (II) to a sulfone of the general formula (III);

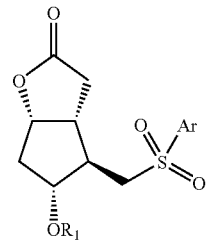

(III)

wherein $R_1$ represents H or a hydroxyl protecting group; and

Ar represents a substituted or an unsubstituted aryl or heteroaryl containing at least one heteroatom selected from the group consisting of O, N, P and S atoms;

(c) reducing the carbonyl group of sulfone of formula (III) and isolating the derivative of lactol of formula (IV) having a desired configuration at the reduced carbon (depending on the desired configuration of the final prostaglandin derivative)

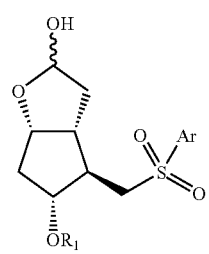

(IV)

wherein $R_1$ represents H or a hydroxyl protecting group; Ar represents a substituted or an unsubstituted aryl or heteroaryl containing at least one heteroatom selected from the group consisting of O, N, P and S atoms;

(d) reacting the lactol of formula (IV) in a Wittig reaction with a precursor of the alpha side chain of the target prostaglandin to yield a compound of the general formula (V)

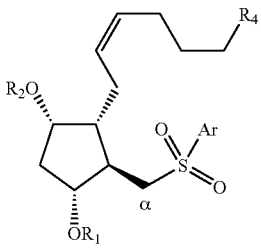

(V)

wherein $R_1$ represents H or a hydroxyl protecting group;

$R_2$ represents H;

Ar represents a substituted or an unsubstituted aryl or heteroaryl containing at least one heteroatom selected from the group consisting of O, N, P and S atoms;

$R_4$ is an orthoester represented by the general formula —$C(OR_6)_3$ or by the general formula (Va),

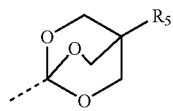

$R_5$ represents H, substituted or unsubstituted $C_1$-$C_6$-alkyl or Ar; and $R_6$ is a substituted or an unsubstituted $C_1$-$C_{10}$-alkyl or Ar;
(e) isolating the compound of the general formula (V), and
(f) optionally, protecting the hydroxyl group —$OR_2$.

The starting derivatives of Corey (−)-lactone of the general formula (I)

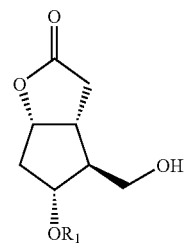

wherein $R_1$ represents H or a hydroxyl protecting group are commercially available or may be obtained by the methods described, for example, in the monograph of E. J. Corey, X-M. Cheng "The Logic of Chemical" John Wiley and Sons, Inc., New York, N.Y., 1989; chapter XI, and in the publication of E. J. Corey, Angew. Chem. Int. Ed. Engl. 30, (1991), 455.

These compounds may be converted into sulfides of formula (II)

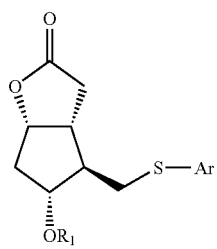

wherein $R_1$ represents H or a hydroxyl protecting group; and Ar represents a substituted or an unsubstituted aryl or heteroaryl containing at least one heteroatom selected from the group consisting of O, N, P and S atoms; in a nucleophilic substitution reaction, allowing the interconversion of primary hydroxyl group of the compound (I) for a leaving group LG. Conveniently, this reaction is carried out under Mitsunobu reaction conditions (Mitsunobu, O, Synthesis 1981, 1), consisting in activation of hydroxyl by dialkyl diazocarboxylate in the presence of $PPh_3$ or $Bu_3P$. In these conditions, addition of a suitable thiophenol results in the formation of a sulfide (D. J. Cundy et al. Org. Prep. Proc. Intl. 32 (2000), 461, P. R. Blakemore et al. Synlett 1998, 26). In order to convert a primary alcohol into an aryl sulfide, the conditions which do not require participation of diazocarboxylate are also used, for example, $PhSSPh/Bu_3P/C_5H_5N$(H. Miayaoka et al., Tetrahedron Lett. 42 (2001), 9233).

Oxidation of sulfides to sulfones (K. R. Guertin, A. S. Kende, Tetrahedron Lett. 34 (1993), 5369 and cited references) is a conversion often used in organic synthesis due to great usefulness of sulfone in synthesis (P. E. Magnus, Tetrahedron 33 (1977), 2019; B. M. Trost Bull. Chem. Soc. Jpn. 61 (1988), 107; N. S. Simpkins, Tetrahedron 46 (1990), 6951). Suitable oxidizing agents are, for example, organic peracids (J. Lamsa, FR 2604707); V. Meladinis et al., Zeitschrift fur Naturforschung, B: Chemical Sciences 44 (1989), 1453: M,-Y. Chen et al., Journal of Organic Chemistry 69 (2004) 2884; M. Therien, Synthesis 2001, 1778). In a preferred embodiment of the invention, the oxidation step is carried out in a two-phase system: an organic solvent non-miscible with water/water, using magnesium monoperoxyphatalate in anhydrous or hydrate form.

Preferably, the oxidation reaction, according to the invention, is carried out in water/methylene chloride medium, in the temperature range of 0-40° C.

Such oxidation conditions reaction eliminate the need for catalysts use and allow easy isolation of product by simple separation of phases after completion of the reaction.

Reduction of lactones to lactols (cyclic hemiacetals of aldehydes) may be carried out, for example, with use of alkyl aluminum hydrides, such as diisobutyl aluminum hydride (i-Bu)$_2$AlH (DIBAL, DIBAL-H). Use of this reagent for reduction of lactones is widely documented in the art of prostaglandin chemistry, especially in the Corey method (E. J. Corey, X.-M. Cheng "The Logic of Chemical Synthesis" John Wiley and Sons, Inc., New York, N.Y., 1989; chapter XI).

Properties of the starting materials of the general formula (II) and the reaction conditions that allow for the preparation of lactols of the general formula (IV)

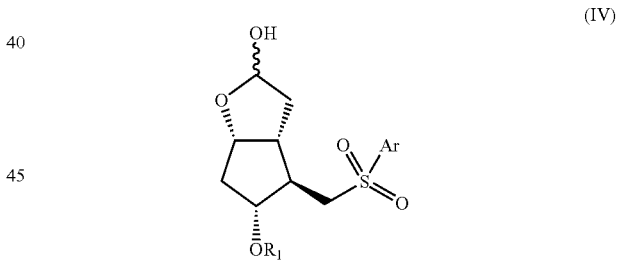

to which the alpha chain of the target derivative of prostaglandin $F_{2\alpha}$ is introduced, are, for example, the same as those of a typical Wittig reaction which uses, e.g., quaternary phosphonium salts.

Quaternary phosphonium salts used as reagents in a Wittig reaction are suitable alkylphosphonium halides, such as bromide, iodide, or chloride. The mechanism and compounds used in a Wittig reaction are generally known. For example, the Wittig reaction of [4'-[4-methyl-2,6,7-trioxabicyclo[2.2.2]oct-1-yl)butyl]triphenylphosphonium bromide with aldehydes is described in G. H. Verdoorn et al., South African Journal of Chemistry 40 (1987), 134-8.

[4-Methyl-2,6,7-trioxabicyclo[2.2.2]oct-1-yl)butyl]triphenylphosphonium iodide has not been described in the prior art. The synthesis of the potentially useful starting compound for the synthesis of this Wittig salt, 1-(4'-iodobutyl)-4-methyl-2,6,7-trioxabicyclo[2,2,2]octane, is described in U.S.

Pat. No. 5,538,995. The preparation of quaternary phosphonium salts useful for the Wittig reaction is usually accomplished by the reaction of triphenylphosphine with an alkyl halide (A. Maeycker, Organic reactions, Wiley, New York, N.Y., 1965, tom 14, p. 270). Reaction of alkyl iodides of complex structure with triphenylphosphine resulting in quaternary phosphonium salts proceeds especially easily in the presence of sulfolane ((J. A. Secrist III, S. R. Wu J. Org. Chem. 44 (1979) 1434).

The Wittig reaction of aldehydes and ylides that are not coupled with electron-accepting groups, carried out without an excess of lithium salts, magnesium salts or salts of other metal of Lewis acid character, results exclusively or largely in the formation of alkens of Z configuration (E. L. Eliel; S. H. Wilen; L. N. Mander "Stereochemistry of Organic Compounds" John Wiley and Sons, Inc., New York, N.Y., 1994; Chapter 9 and Chapter 12). The Wittig reaction of phosphonium salts with γ-hydroxy-aldehydes or their equivalents, which are five-membered lactols, is described, among others, in the case of prostaglandins (H. O. House "Modern Synthetic Reactions", W. A. Benjamin, Inc., Menlo Park, Calif., USA, 1972; E. J. Corey, X.-M. Cheng "The Logic of Chemical Synthesis", John Wiley and Sons, Inc., New York, N.Y., 1989; chapter XI). In such reactions, bases, such as potassium t-butoxide (t-BuOK), butyllithium (BuLi), lithium hexamethyldisilazide (LHMDS), dimesilate anion, and tertiary amines, are used for the generation of the anion (ylide).

In the preferred embodiment of the invention, the Wittig reaction is carried out in the presence of aluminum organocompounds, preferably in the presence of Al(t-BuO)$_3$.

The use of aluminum organo-compounds, such as Al(t-BuO)$_3$, in the reactions of this type, has not been described in the prior art. However, high chemical affinity of many aluminum (III) salts for oxygen atoms present in organic compound molecules is known (H. Yamamoto "Organoaluminum Compounds", in: M. Schlosser, ed.: "Organometallics in Synthesis", John Wiley and Sons, New York, N.Y., 1994; Chapter 7), as well as is the strong basic character of tert-BuO$^-$ ion (H. O. House "Modern Synthetic Reactions", W. A. Benjamin, Inc., Menlo Park, Calif., USA, 1972; J. March "Advanced Organic Chemistry" John Wiley and Sons, New York, N.Y., 1992), on which the concept of their use in the synthesis according to the invention is based.

Essential for the course of preparation of PGF$_{2\alpha}$ and especially for purification of the final product is the use of the compound of the general formula (VI) of high enantiomeric purity for the reaction with Corey (−)-lactone.

Compounds of the general formula (VI) having an R or S configuration at the hydroxy-substituted carbon, Z represents H, methyl or phenyl, optionally substituted by C$_{1-3}$-alkyl, C$_{1-3}$-alkoxy or at least one halogen atom; and n represents an integer from 0 to 6;

are prepared in a process characterized in that:

(a) a primary hydroxyl group of a corresponding (2S)- or (2R)-4-phenyl-1,2-alkyldiol of formula OH—CH—CH(OH)—(CH$_2$)$_n$-Z, wherein Z represents H, methyl or phenyl, optionally substituted by C$_{1-3}$-alkyl, C$_{1-3}$-alkoxy or at least one halogen atom; and n represents an integer from 0 to 6; is converted selectively into an ArSO$_2$O— group, wherein Ar represents a substituted or an unsubstituted aryl or heteroaryl containing at least one heteroatom selected from the group consisting of O, N, P and S atoms; to obtain the compound of formula (VI), wherein LG represents a substituted or an unsubstituted aryl or heteroaryl;

(b) a secondary hydroxyl group of the compound of formula (VI) obtained at step (a) is protected by introducing an R$_3$ protecting group;

(c) the ArSO$_2$O— group of compound of formula (VI) is substituted by halogen atom, to obtain the compound of formula (VI), wherein LG is halogen atom;

(d) the compound (VI), wherein LG represents a halogen atom or an ArSO$_2$O— group, and R$_3$ represents a protecting group, is converted into the compound of formula (VI), wherein LG and OR$_3$ together form a cyclic epoxy ring; or, alternatively are prepared in a process characterized in that:

(e) (2S)- or (2R)-4-phenyl-1,2-alkyldiol of formula OH—CH—CH(OH)—(CH$_2$)$_n$-Z, wherein Z represents H, methyl or phenyl, optionally substituted by C$_{1-3}$-alkyl, C$_{1-3}$-alkoxy or at least one halogen atom; and n represents an integer from 0 to 6, is converted into the compound of formula (VI), wherein LG and R$_3$ form a sulfite (—S(O)—) ring, and then, optionally, (f) the compound of formula (VI) of step (e) is oxidized to a compound of formula (VI), wherein LG and R$_3$ taken together form a sulfate (—S(O$_2$)—) ring, and, optionally, (g) the hydroxyl group is protected.

The oxidation in step (f) may be carried out with the use of a strong inorganic oxidizing agent, such as NaIO$_4$/RuCl$_3$.

Optionally, the cyclic sulfate may be prepared directly in the reaction of 2(S)- or 2(R)-phenyl-1,2-alkyldiol with sulfuryl chloride.

An alternative process for preparation of a compound of the general formula (VI) having an R or S configuration at the hydroxy-substituted carbon

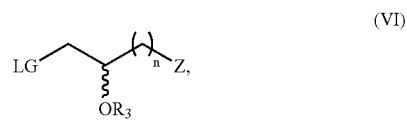

(VI)

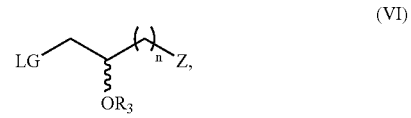

(VI)

wherein

LG represents a halogen, an alkylsulfonyloxy, an alkylarylsulfonyloxy, or a arylsulfonyloxy group, and R$_3$ represents H or a hydroxyl protecting group; or LG and R$_3$ represent a chemical bond and/or taken together with the atoms to which they are attached and with an —S(O)— or an —SO$_2$— group form a cyclosulfite or a cyclosulfate; or LG and R$_3$ represent chemical bonds and/or taken together with the atoms to which they are attached form an epoxide;

wherein

LG represents a halogen, an alkylsulfonyloxy, an alkylarylsulfonyloxy, or a arylsulfonyloxy group, and R$_3$ represents H or a hydroxyl protecting group; or LG and R$_3$ represent a chemical bond and/or taken together with the atoms to which they are attached and with an —S(O)— or an —SO$_2$— group form a cyclosulfite or a cyclosulfate; or LG and R$_3$ represent chemical bonds and/or taken together with the atoms to which they are attached form an epoxide;

Z represents H, methyl or phenyl, optionally substituted by $C_{1-3}$-alkyl, $C_{1-3}$-alkoxy or at least one halogen atom; and
n represents an integer from 0 to 6;

is characterized in that:

(a) a derivative of D- or L-glyceric aldehyde of formula $R_{1}O$—CH—CH(OR$_2$)—CHO, wherein $R_1$ and $R_2$ represent a hydroxyl protecting group or taken together constitute a fragment of a dioxolane ring, is reacted in a Wittig reaction with a tertiary phosphonium salt of the formula $^{(+)}PPh_3$—$CH_2$—$(CH_2)_{n-2}$-$ZX^{(-)}$, wherein Z represents H, methyl or phenyl, optionally substituted by $C_{1-3}$-alkyl, $C_{1-3}$-alkoxy or at least one halogen atom; n represents an integer from 0 to 6; and $X^{(-)}$ represents bromide, iodide or chloride anion;

(b) the alkene obtained in step (a) is hydrogenated;

(c) the hydroxyl protecting groups are removed, to obtain a derivative of a 1,2-diol;

(d) the primary hydroxyl group of (2S)- or (2R)-4-phenyl-1,2-alkyl-diol of formula OH—CH—CH(OH)—$(CH_2)_n$-Z, wherein Z represents H, methyl or phenyl, optionally substituted by $C_{1-3}$-alkyl, $C_{1-3}$-alkoxy or at least one halogen atom; and n represents an integer from 0 to 6; obtained in step (b) or (c), is converted into a $ArSO_2O$—, a Cl—SO—O— or a $C_1$—$SO_2$—O— group, wherein Ar represents an aryl or a heteroaryl;

(e) the secondary hydroxyl group of the compound prepared in step (d) is protected; and, optionally, (f) the $ArSO_2O$— group is substituted by a halogen atom.

Figure 2:
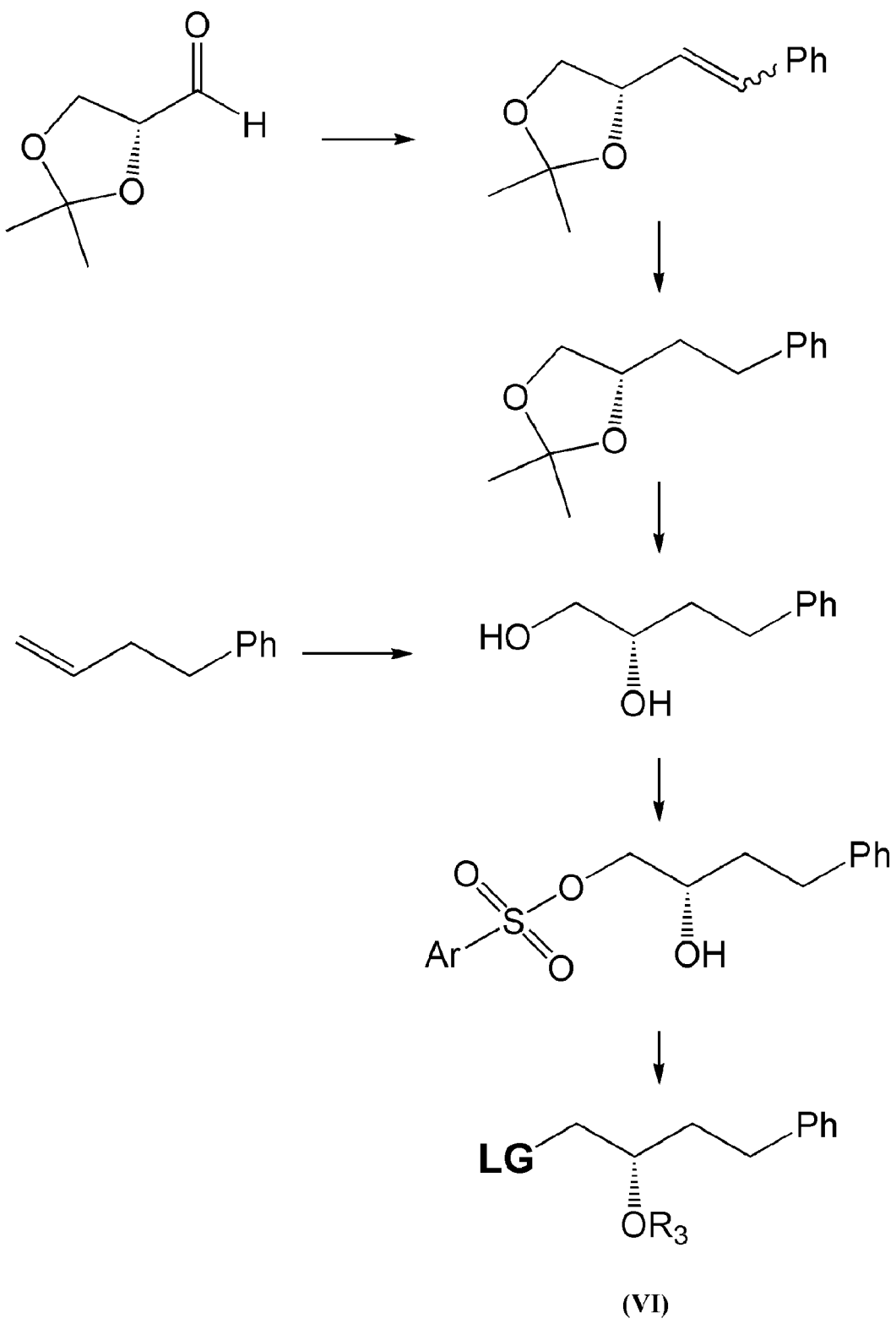
FIG. 2 shows the general route for the synthesis of compounds of formula (VI).
Figure 3:
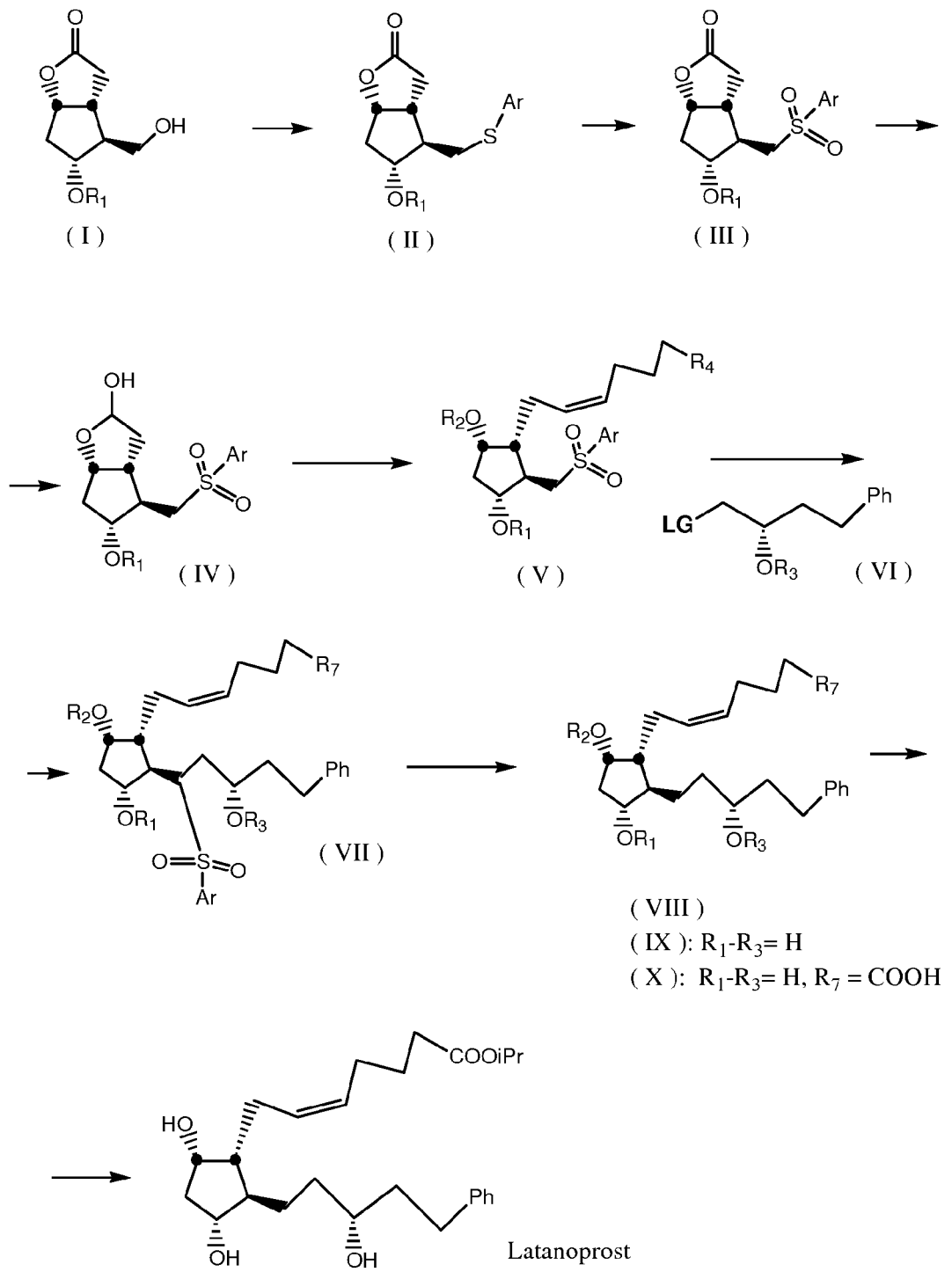
FIG. 3 shows the general route of the process for preparation of 13,14-dihydro-PGF$_{2\alpha}$ derivatives according to the invention, on the example of latanoprost, i.e., 13,14-dihydro-17-phenyl-18,19,20-trinor-PGF$_{2\alpha}$ isopropyl ester.
Figure 4:
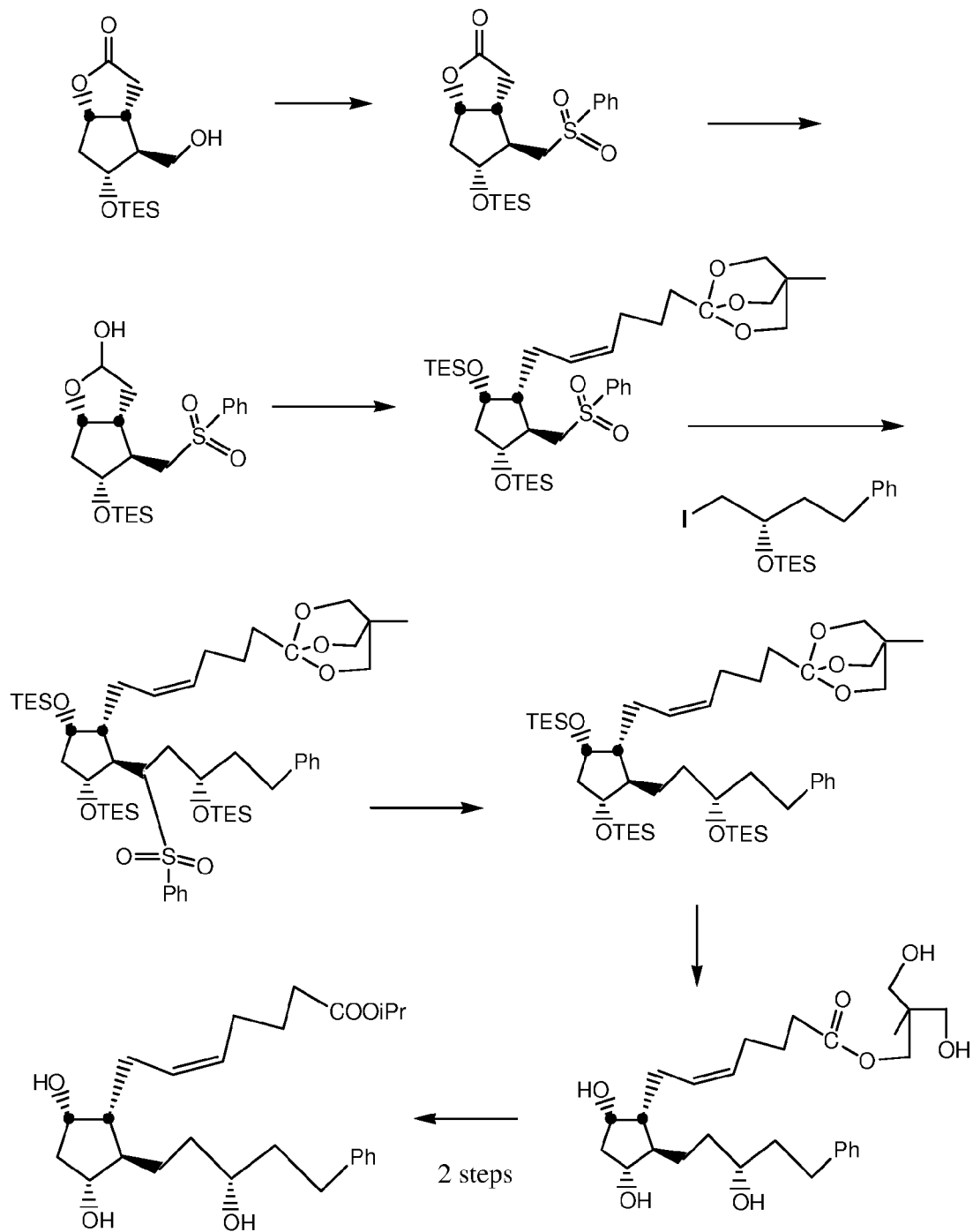
FIG. 4 illustrates the synthesis of latanoprost using the compound of formula (V) as a starting material, wherein R is an orthoester group (OBO).

The process for the preparation of the preferred compound of the formula (VI) having an S configuration, wherein n=2, and Z represents phenyl, being a valuable starting compound in the process of preparation of latanoprost according to the invention, is illustrated in FIG. 2.

Using of 2(S)-4-phenyl-1,2-butanediol of enantiomeric excess above 99%, and preferably above 99.5%, as the starting compound in the above process, provides compounds of the formula (VI) which are useful for latanoprost preparation.

Generally, derivatives of terminal 1,2-diols of high degree of optical purity are prepared, for example, in the reaction of asymmetrical dihydroxylation of terminal alkenes (H. Becker, K. B. Sharpless, Angew, Chem. Int. Ed. Engl. 35 (1996), 448-450; T. J. Hodgkinson, M. Shipman, Synthesis 1998, 1141-1144; H. C. Kolb et al., Chem. Rev. 94 (1994)). Synthesis of (2R)-1,2-dihydroxy-4-phenylbutane of ee=84% enantiomeric excess, with use of $(DHQD)_2PHAL$ catalyst, is described in Z.-M. Wang et al., Tetrahedron Lett. 34 (1993), 2267-2270. Preparation of non-racemic (2S)-1,2-dihydroxy-4-phenylbutane is also described in: J. Hasegawa at al., Agric. Biol. Chem. 54 (1990), 1819-1827; T. Tsujigami at al., Tetrahedron: Asymmetry 12 (2001), 2543-2549; B. P. Branchaud, H. S. Blanchette, Tetrahedron Lett. 43 (2002), 351-353; T. Ishida at al., Adv. Synth. Catal. 345 (2003), 576-579; M. Rezaei at al., Tetrahedron Lett. 44 (2003), 7513-7516.

Optically active 2,3-O-isopropylidene-D-glyceric aldehyde, the starting compound in one of variants of the synthesis of the compounds (VI), may be prepared in the process described by C. R. Schmid et al., Organic Syntheses, Coll. Vol. 9 (1998), 450, from readily available D-mannitol, which is first converted into bis-acetonide, and then into 2,3-O-isopropylidene-D-glyceric aldehyde, by use of sodium periodate. 2,3-Isopropylidene-D-glyceric aldehyde may be used as a chiral synthone of 1,2-diol in a chain extension reaction. One method of the extension of chain of defined functionalization and stereochemistry is the Wittig reaction between functionalized aliphatic aldehydes and ylides prepared from alkyltriphenylfosphonim salts. It results in the formation of alkenes, often in the form of a mixture of E and Z isomers, which may be then further reacted, for example, in a hydrogenation reaction on palladium catalyst (H. O. House "Modern Synthetic Reactions", W. A. Benjamin, Inc., Menlo Park, Calif., USA, 1972), to give alkanes of longer carbon chain with retention of substitutents which are primarily attached to the starting alkyl chain of the aldehyde. The use of such process for the synthesis of non-racemic (2S)-1,2-dihydroxy-4-phenylbutane is described in publications of J. Hasegawa et al., Agric. Biol. Chem., 54 (1990); and M. Rezaei et al., Tetrahedron Lett 44 (2003), 7513-7516. 1,2-O-isopropylidene derivatives are easily hydrolyzed, for example, in the presence of protonic acids (T. W. Greene, P. G. M. Wuts "Protective Groups in Organic Synthesis", $3^{rd}$ ed., John Wiley and Sons, Inc., New York, N.Y., 1999), resulting in the formation of 1,2-diols in a good yield.

The thus prepared 1,2-diol is reacted with thionyl chloride or with sulfuryl chloride to firm a cyclic sulfite or sulfate, respectively (H. C. Kolb et al., Chem. Rev. 94 (1994) and cited references). Optionally, a cyclic sulfate is prepared in the process of oxidation of a cyclic sulfate.

The 1,2-diol of high enantiomeric excess is then converted into an alkylating agent of the formula (VI), wherein LG represents a good leaving group. Good leaving groups are, for example, sulfonate groups and halogen atoms (J. March "Advanced Organic Chemistry", John Wiley and Sons, New York, N.Y., 1992; H. O. House "Modern Synthetic Reactions", W. A. Benjamin, Inc., Menlo Park, Calif., USA, 1972), especially if they are attached directly to a methylene group having a small steric hindrance. Both primary halides and primary alkyl sulfonates react easily in nucleophilic substitution reactions. Processes for conversion of sulfonates into the corresponding iodides or bromides are described in the same publications.

However, the preparation of (S)-2-hydroxy-4-phenylbutyl 4-methylbenzenesulfonate in the substitution reaction of 2(S)-1,2-epoxy-3-p-toluenesulfonyloxypropane with benzyl anion usually results in a formation of compounds of low enantiomeric excess (ee=94%, 3% of isomer 3(R)). J. M. Klunder et al., J. Org. Chem. 54 (1989), 1295-1304).

In contrast, the process according to this invention allows for the preparation of 3(S)-1-phenyl-3-hydroxy-4-p-toluenesulfonyloxybutane of very high enantiomeric excess, when starting 2(S)-4-phenyl-1,2-butanediol of high optical purity (ee>99%) is used.

Conversion of 2-hydroxy-1-sulfonyloxyalkanes into primary alkyl halides in the presence of a base is accompanied by formation of 1,2-epoxys, which are also useful as alkylating agents (H. C. Kolb et al., Chem. Rev. 94 (1994); B. Achmatowicz et al., J. Chem. Soc. Chem. Commun. (1987), 1226-8). However, this reaction may be avoided, after prior introduction of 2-hydroxyl protecting group, e.g., the O-silyl group.

The following examples are provided to illustrate the invention. The examples are not meant to limit the scope of the invention as defined in the claims.

EXAMPLES

A protected Corey (−)-lactone, the (3aR,4S,5R,6aS)-4-hydroxymethyl-5-triethylsilyloxy-hexahydrocyclopenta[b]furan-2-one, was used as a starting material. It was commercially available from Pharma Tech International Inc. $[\alpha]_D$= (−)47.5° (CHCl$_3$, 20° C., c=1); $^1$H-NMR (CDCl$_3$; 200 MHz) δ 0.59 (6H, q, 8 Hz), 0.95 (9H, t, 8 Hz), 2.00 (3H, m), 2.28 (1H, m), 2.54 (1H, dd: 16.7, 1.8 Hz), 2.74 (2H, m), 3.60 (2H, bd: 5.8 Hz), 4.13 (1H, q, 5.7 Hz), 4.93 (1H, ddd: 7.0, 7.0, 2.8 Hz); $^{13}$C-NMR (CDCl$_3$; 50 MHz) δ 4.7 (3C), 6.7 (3C), 35.4, 38.8, 41.0, 56.2, 62.7, 74.6, 83.5, 177.1.

Example 1

(3aR,4R,5R,6aS)-4-(phenylthio)methyl-5-(triethylsilyloxy)hexahydrocyclopenta[b]furan-2-one

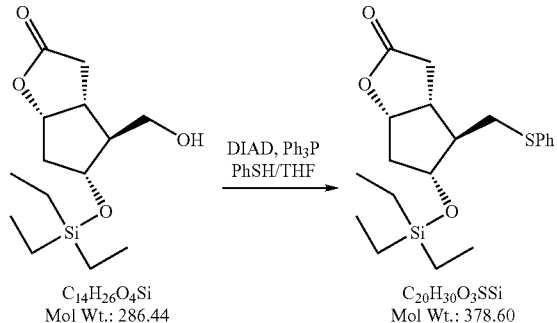

C$_{14}$H$_{26}$O$_4$Si
Mol Wt.: 286.44

C$_{20}$H$_{30}$O$_3$SSi
Mol Wt.: 378.60

(3aR,4S,5R,6aS)-4-Hydroxymethyl-5-(triethylsilyloxy)-hexahydrocyclopenta[b]furan-2-one (11.45 g, 40.0 mM) was dissolved in anhydrous CH$_2$Cl$_2$ (40 mL). Then, anhydrous tetrahydrofurane (20 mL) and Ph$_3$P (13.1 g, 50 Mm) were added and stirred at room temperature. After dissolution, the reaction mixture was cooled to +15° C. and PhSH was added (5.51 g, 5.15 mL, 50 mM). After stirring for 5 minutes, a solution of diisopropyl diazocarboxylate (DIAD, 95%; 10.4 mL, 50 mM) in anhydrous THF e was added slowly, over 5 minutes, from a syringe. The reaction mixture was allowed to stir while being slowly heated to +25° C. After 15 hours, THF (25 mL) was added and the mixture was heated to +40° C. under argon for 9 hours, and then it was stirred at room temperature for 16 hours. The mixture was concentrated under vacuum to give 41 g mass (oil), which was purified by flash chromatography on silica gel column 230-400 mesh (440 g). The product was eluted with hexane (75%)-EtOAc (12.5%)-CH$_2$Cl$_2$ (12.5%) mixture of solvents.

(3aR,4R,5R,6aS)-4-(phenylthio)methyl-5-(triethylsilyloxy)hexahydrocyclopenta[b]furan-2-one (10.84 g, 71.6%) was obtained as a colorless, thick oil; $[\alpha]_D=(-)31.0°$ (CHCl$_3$, 25° C., c=1); $^1$H-NMR (CDCl$_3$; 200 MHz) δ 0.56 (6H, q: 8.0 Hz), 0.92 (9H, t: 8.0 Hz), 2.00 (1H, m), 2.08 (1H, m), 2.22 (1H, m), 2.45-2.85 (4H, m), 3.02 (1H, dd: 13.2, 5.9 Hz), 4.08 (1H, q: 5.0 Hz), 4.95 (1H, ddd: 7.0, 6.8, 2.8 Hz), 7.31 (5H, m); $^{13}$C-NMR (CDCl$_3$; 50 MHz) δ 4.6 (3C), 6.7 (3C), 35.8, 36.1, 40.6, 41.8, 54.0, 76.3, 83.1, 126.2, 129.0 (2C), 129.1 (2C), 135.4, 176.9; EI MS m/z 379 (M+H, 2%); Elem. analysis: for C$_{20}$H$_{30}$O$_3$SSi calc. % C, 63.45; % H, 7.99; % S, 8.47. found. % C, 63.37; % H, 8.03; % S, 8.46.

Example 2

(3aR,4R,5R,6aS)-4-(phenylosulfonyl)methyl-5-triethylsilyloxy)hexahydro-cyclopenta[b]furan-2-one

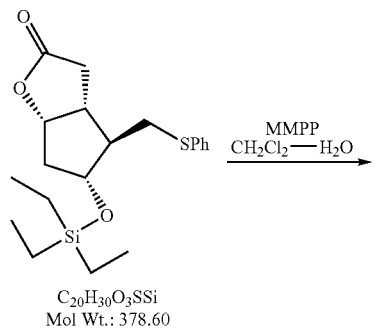

C$_{20}$H$_{30}$O$_3$SSi
Mol Wt.: 378.60

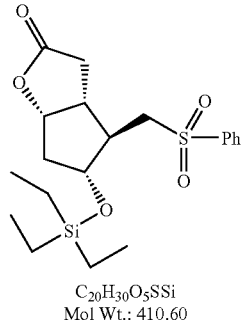

C$_{20}$H$_{30}$O$_5$SSi
Mol Wt.: 410.60

(3aR,4R,5R,6aS)-4-(Phenylthio)methyl-5-(triethylsilyloxy)-hexahydrocyclopenta[b]furan-2-one (9.55 g, 25.2 mM) was dissolved in CH$_2$Cl$_2$ (150 mL). The solution was cooled in a water bath (17° C.). Upon intensive stirring, over 2 minutes, a suspension of magnesium monoperoxyphtalate hexahydrate (MMPP×6H$_2$O) (89.7 g, 80%, approx. 145 mM, approx. 5.7 of equivalent) in H$_2$O (230 mL) was added. The stirring was continued for 65 minutes, CH$_2$Cl$_2$ (100 mL) was added, and upon intensive stirring and cooling (17° C.), saturated aqueous solution of NaHCO$_3$ (350 mL) was added dropwise over 20 minutes. After the dropwise addition was completed, it was stirred for 15 minutes more; then the layers were separated, the aqueous layer was extracted with CH$_2$Cl$_2$ (40 mL), the organic layers were combined and extracted again with saturated aqueous NaHCO$_3$ (300 mL) solution. Phases were separated, the aqueous phase was washed with CH$_2$Cl$_2$ (40 mL). The combined organic phases were extracted with 10% Na$_2$S$_2$O$_3$ aqueous solution (500 mL). Phases were again separated, and the aqueous phase was washed with CH$_2$Cl$_2$ (40 mL). The combined organic phases were extracted with NaHCO$_3$ solution (300 mL), dried over MgSO$_4$ (50 g), the drying agent was filtered and washed with CH$_2$Cl$_2$ (5 mL). The filtrates were combined, concentrated and dried under vacuum (1 mm Hg, 30° C., 30 min.). Colorless oil was obtained (11.86 g). The oil was purified by flash chromatography on silica gel column 230-400 mesh (350 g), eluent: 40% EtOAc in hexane. The collected fractions containing product were concentrated and dried over vacuum (1 mm Hg, 30° C., 60 min.).

(3aR,4R,5R,6aS)-4-(Phenylosulfonyl)methyl-5-(triethylsilyloxy)hexahydrocyclopenta[b]furan-2-one was obtained in the form of a colorless solidifying oil (9.81 g, 94.8%); $[\alpha]_D=(-) 24.9°$(CHCl$_3$, 25° C., c=1); $^1$H-NMR (CDCl$_3$; 200 MHz) δ 0.53 (6H, q: 8.0 Hz), 0.89 (9H, t: 8.0 Hz), 1.98 (1H, m), 2.15 (1H, m), 2.33 (1H, m), 2.62-2.98 (4H, m), 3.18 (1H, dd: 13.9, 4.4 Hz), 4.01 (1H, q: 5.1 Hz), 4.98 (1H, ddd: 7.1, 6.8, 3.5 Hz); $^{13}$C-NMR (CDCl$_3$; 50 MHz) δ 4.6 (3C), 6.7 (3C), 35.8, 40.4, 41.9, 49.4, 58.5, 76.7, 82.6, 127.7 (2C), 129.4 (2C), 133.9, 139.0, 176.6; ESI HRMS m/z 433.1497 (M+Na$^+$); 411.1676 (M+H$^+$), for C$_{20}$H$_{31}$O$_5$SSi 411.1662 was calculated, for C$_{20}$H$_{30}$O$_5$SSiNa 433.1481 was calculated; elem. analysis: for C$_{20}$H$_{30}$O$_5$SSi calc. % C, 58.50; % H, 7.36; % S, 7.81. found. % C, 58.36; % H, 7.22; % S, 8.01.

Example 3

(2R/S,3aR,4R,5R,6aS)-4-(phenylosulfonyl)methyl-5-(triethylsilyloxy)hexahydro-2H-cyklopenta[b]furan-2-ol

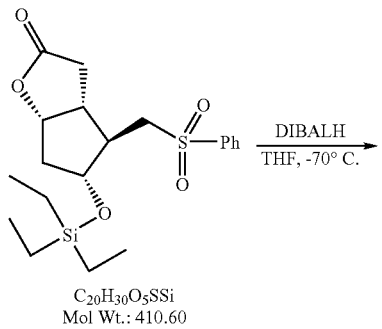

C$_{20}$H$_{30}$O$_5$SSi
Mol Wt.: 410.60

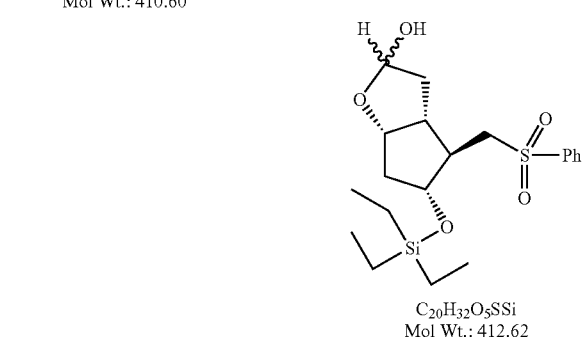

C$_{20}$H$_{32}$O$_5$SSi
Mol Wt.: 412.62

(3aR,4R,5R,6aS)-4-(Phenylsulfonyl)methyl-5-(triethylsilyloxy)hexahydro-cyclopenta[b]furan-2-one (9.26 g, 22.55 mM) was dissolved in anhydrous THF (120 mL). The solution was cooled under argon to −75° C. DIBALH solution (1.4 M in toluene; 35 mL, 49.6 mM) was added slowly, over 5 minutes. The solution was stirred under argon at −75° C. After 2 hours, upon continuation of vigorous stirring and cooling in CO$_2$/MeOH bath, MeOH (9.5 mL, 234 mM) was slowly added dropwise. Then the cooling bath was removed and stirring was continued, allowing for slow warming of the mixture to −5° C. H$_2$O (130 mL) and 2M aqueous solution of NaHSO$_2$ (100 mL) were consecutively added dropwise, and stirring was continued for 5 minutes. EtOAc (100 mL) was added, phases were separated after extraction, and the aqueous phase was extracted twice with EtOAc (2×80 mL). Organic layers were combined and extracted twice with brine (2×200 mL), then they were dried over anhydrous Na$_2$SO$_4$ (50 g); the drying agent was filtered, washed with EtOAc (40 mL). The combined filtrates were concentrated and dried under vacuum (5 mm Hg, 30° C., 30 min. and 1 mm Hg, 30° C., 1 hour). Thick, colorless oil (10.1 g) was obtained. This sample was purified by flash chromatography on silica gel column 230-400 mesh (200 g), eluent: 42% EtOAc in hexane+0.02% C$_5$H$_5$N. Upon resolution, EtOAc concentration was gradient-increased up to 50%. The product was dried under vacuum (1 mm Hg, 30° C., 90 min.).

(2R/S,3aR,4R,5R,6aS)-4-(Phenylsulfonyl)methyl-5-(triethylsilyloxy)hexahydro-2H-cyclopenta[b]furan-2-ol was obtained (approx. 3:1 mixture of two epimers), as a colorless thick oil (8.50 g, 91.3%); $^1$H-NMR (CDCl$_3$; 200 MHz) δ 0.52 (6H, 2×q), 0.89 (9H, 2×t), 1.62 (0.75H, m), 1.98-2.37 (4H, m), 2.62 (1.25H, m), 2.90-3.04 (1.75H, m), 3.23 (0.25H, dd: 14.1, 4.4 Hz), 3.36 (0.75H, dd: 14.0, 3.1 Hz), 3.78 (0.75H, ddd: 8.8, 8.6, 5.8 Hz), 3.98 (0.25H, bq: 5.1 Hz), 4.60 (1.25H, m), 5.48 (0.25H, ddd: 6.4, 4.5, 1.7 Hz), 5.62 (0.75H, dd: 3.7, 3.5 Hz), 7.91 (2H, m), 7.61 (3H, m); $^{13}$C-NMR (CDCl$_3$; 50 MHz) δ 4.45, 4.73, 6.63, 6.73, 40.36, 40.68, 40.99, 42.54, 44.18, 46.43, 48.45, 49.08, 59.04, 59.80, 77.39, 78.46, 79.90, 83.62, 100.42 i 101.22 (hemiacetal), 127.61, 127.80, 129.19, 129.23, 133.54, 133.66, 139.28, 139.58; Elem. anal: for C$_{20}$H$_{32}$O$_5$SSi calc. % C, 58.22; % H, 7.82; % S, 7.77. found. % C, 57.98; % H, 7.78; % S, 8.05.

Example 4

[4-(4-methyl-2,6,7-trioxabicyclo[2.2.2]oct-1-yl)butyl]triphenylphosphonium iodide

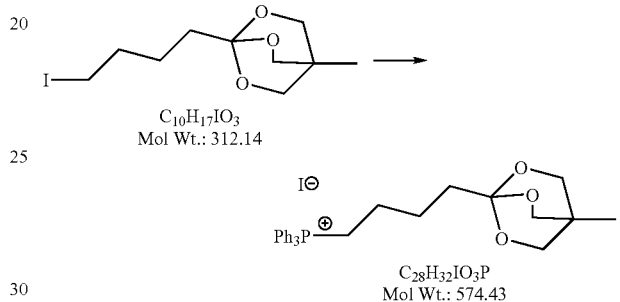

C$_{10}$H$_{17}$IO$_3$
Mol Wt.: 312.14

C$_{28}$H$_{32}$IO$_3$P
Mol Wt.: 574.43

In a 250 mL flask, 1-(4-iodobutyl)-4-methyl-2,6,7-trioxabicyclo[2.2.2]octane prepared according to process described in U.S. Pat. No. 5,538,995 (15.8 g, 50.6 mM), triphenylphosphine (14.6 g, 55.66 mM), sulfolane (20 mL) and C$_5$H$_5$N (0.10 mL) were placed under argon. The content of the flask was stirred and heated under argon at 80° C. After 70 minutes, the mixture was cooled to 40° C. and CHCl$_3$ containing 0.3% of pyridine (70 mL) was added. This solution was added dropwise over 10 minutes to the mixture of Et$_2$O (1.5 L) and EtOAc (0.6 L) and vigorously stirred under argon. The reaction mixture was vigorously stirred (600 r.p.m.) for 15 minutes at room temperature, then it was stirred more slowly (150 r.p.m.) for 15 minutes, and the solution was decanted. The thus obtained precipitate was dissolved in CHCl$_3$ containing 0.2% of C$_5$H$_5$N (75 mL). This solution was added dropwise to vigorously stirred mixture of Et$_2$O (1.2 L) and EtOAc (0.5 L). It was stirred under argon at room temperature. After 20 minutes, stirring was stopped. After 10 minutes, the solution was decanted, the precipitate was washed with Et$_2$O (100 mL) and Et$_2$O layer was decanted again. The obtained precipitate was dried under vacuum (1 mm Hg, 25° C., 1.5 h). The crude product (28.95 g, 100%) was obtained. This sample was dissolved in MeOH containing 0.04% of C$_5$H$_5$N (35 mL), EtOAc containing 0.04% of C$_5$H$_5$N (65 mL) was added and it was allowed for crystallization at +4° C. After 1.5 h, the precipitate was filtered and dried (1 mm Hg, 25° C., 1 h). [4-(4-methyl-2,6,7-trioxabicyclo[2.2.2]oct-1-yl)butyl]triphenylphosphonium iodide was obtained (14.01 g, 48.3%) as colourless, thick prisms, t.t.=130-134° C.; $^1$H-NMR (CDCl$_3$; 200 MHz) 6; 0.78 (3H, s), 1.58-1.80 (6H, m), 3.45 (2H, m), 3.79 (6H, s), 7.70-7.88 (15H, m); $^{13}$C-NMR (CDCl$_3$; 50 MHz) δ 14.5, 21.7 (d: 4.0 Hz), 22.7 (d: 50.8 Hz), 24.0 (d: 16.8 Hz), 30.2, 34.7, 72.3 (3×C), 108.5, 117.8 (3×C, d: 86 Hz), 130.5 (6×C, d: 12.4 Hz), 133.5 (6×C, d: 10.0 Hz), 135.1 (3×C, d: 2.8 Hz).

Example 5

(1R,3S,4R,5R)-4-[(Z)-6-(4-methyl-2,6,7-trioxabicyclo[2.2.2]octan-1-yl)hex-2-enyl]-5-[(phenylosulfonyl)methyl]cyclopentane-1,3-diol and the mixture of (1R,2R,3R,4S)-3-[(Z)-6-(4-methyl-2,6,7-trioxabicyclo[2.2.2]octan-1-yl)hex-2-enyl]-2-[(phenylsulfonyl)methyl]-4-(triethylsilyloxy)cyclopentanol and (1S,2R,3R,4R)-2-[(Z)-6-(4-methyl-2,6,7-trioxabicyclo[2.2.2]octan-1-yl)hex-2-enyl]-3-[(phenylsulfonyl)methylo]-4-(triethylsilyloxy)cyclopentanol.

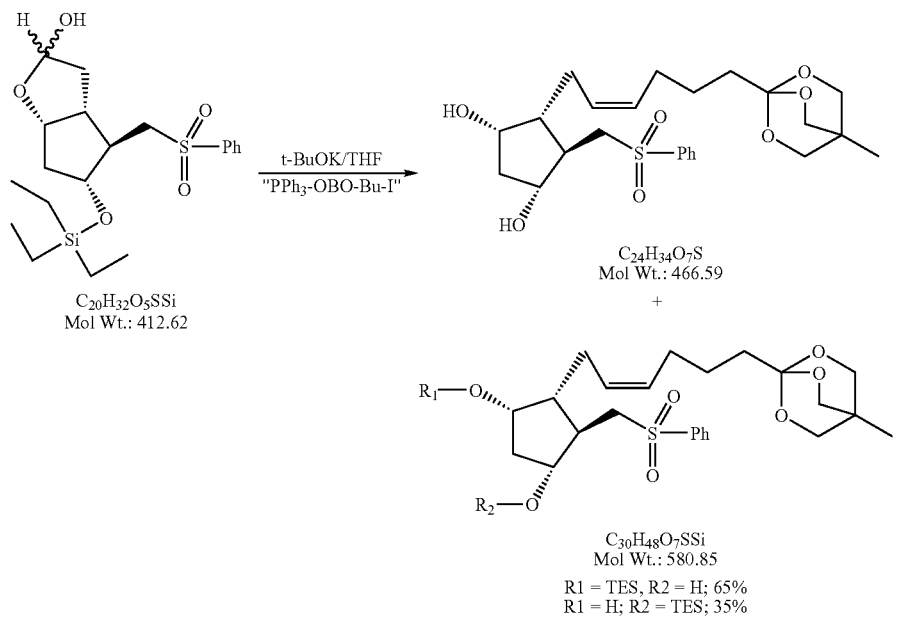

[4-(4-methyl-2,6,7-trioxabicyclo[2.2.2]octan-1-yl)butyl]triphenylphosphonium iodide (7.98 g, 13.9 mM) and anhydrous THF were stirred under argon at room temperature for 30 minutes. Then the mixture was cooled under argon to 0° C. and t-BuOK was added in several portions (Fluka>97%, 3.85 g total, approx. 34 mM). The mixture was stirred at 0° C. for 5 minutes, then the cooling bath was removed, anhydrous THF (10 mL) was added, and it was stirred over 20 minutes, allowing the mixture to warm up to approx. 20° C. Then the mixture was cooled again to 0° C. and, over 3 minutes, while stirring vigorously, the solution of (2R/S,3aR,4R,5R,6aS)-4-(phenylsulfonyl)methyl-5-(triethylsilyloxy)hexahydro-2H-cyclopenta[b]furan-2-ol (mixture of epimers) (2.70 g, 6.54 mM) in anhydrous THF (10 mL) was added dropwise. Stirring at 0° C. was continued for 15 minutes, then the cooling bath was removed and it was vigorously stirred under argon, allowing the mixture to warm up to 20° C. 80 minutes after lactol was added dropwise, Al(t-BuO)$_3$ (420 mg, approx. 1.7 mM) was added and stirring was continued at 20° C. under argon. Exactly 5 hours after the reaction was started, the reaction mixture was cooled to 0° C. and 3% solution of pyridine in H$_2$O (10 mL) was added very slowly. It was stirred for 5 minutes, then the mixture was transferred to a separator containing EtOAc (70 mL) and saturated aqueous solution of NaHCO$_3$ (70 mL). After extraction, the layers were separated, the aqueous layer was extracted twice with EtOAc (50 mL, 30 mL), then the organic layers were combined and extracted twice with saturated brine (50 mL, 50 mL). 3 drops of pyridine were added to the organic layer, and it was dried over anhydrous Na$_2$SO$_4$ (25 g) at +4° C. over night. Then the drying agent was filtered, washed with EtOAc (30 mL), the combined filtrates were concentrated and dried under vacuum. Thick oil (8.2 g) was obtained, which was dissolved in CH$_2$Cl$_2$ (20 mL) and injected on flash chromatographic silica gel column 230-400 mesh (250 g), previously prepared in the mixture of 70% EtOAc-30% hexane+0.15% C$_5$H$_5$N (Phase I). After collecting of 2 L of eluate washed out with Phase I, mobile phase was exchanged for Phase II: 84% EtOAc-16% hexane+0.15% C$_2$H$_5$N. Fractions obtained by washing out with Phase I were combined on the basis of TCL chromatograms, concentrated and dried under vacuum.

The mixture of (1R,2R,3R,4S)-3-[(Z)-6-(4-methyl-2,6,7-trioxabicyclo[2.2.2]octan-1-yl)hexe-2-nyl]-2-[(phenylsulfonyl)methyl]-4-(triethylsilyloxy)cyclopentanol (ca. 65%) and (1S,2R,3R,4R)-2-[(Z)-6-(4-methyl-2,6,7-trioxabicyclo[2.2.2]octan-1-yl)hex-2-enyl]-3-[(phenylsulfonyl)methyl]-4-(triethylsilyloxy)cyclopentanol (ca. 35%) (584 mg of the mixture, yield 15.4%), colorless glaze was obtained; $^1$H-NMR (CDCl$_3$; 200 MHz) δ 0.57 (6H, 2×q), 0.79 (1.95H, s), 0.80 (1.05H, s), 0.93 (9H, 2×t), 1.34-1.54 (3.5H, m), 1.56-1.78 (3H, m), 1.82-2.20 (6.6H, m), 3.01 (0.65H, dd: 14.4, 11.2 Hz), 3.32 (0.65H, dd: 14.4, 2.6 Hz), 3.56 (0.65H, m), 3.88 (3.9H, s), 3.89 (2.1H, s), 3.90 (0.35H, m), 4.13 (1.30H, m), 5.15-5.38 (2H, m), 7.54-7.74 (3H, m), 7.93-7.99 (2H, m); fractions prepared after washing out with Phase II were combined on the basis of TLC chromatograms, concentrated and dried under vacuum. Glaze was obtained (3.597 g) containing slight amount of triphenylphosphine oxide, which was removed by two-time maceration with Et$_2$O (8 mL, 4 mL). (1R,3S,4R,5R)-4-[(Z)-6-(4-Methyl-2,6,7-trioxabicyclo[2.2.2]octan-1-yl)hex-2-enyl]-5-[(phenylsulfonyl)methyl]cyclopentane-1,3-diol was prepared (2.0 g, 65.5%); $^1$H-NMR (CDCl$_3$; 200 MHz) δ 0.80 (3H, s), 1.36-1.52 (3H, m), 1.61 (2H, m), 1.8-2.29 (8H, m), 3.05 (1H, dd: 14.3, 11.2 Hz), 3.33 (1H, dd: 14.3, 2.6 Hz), 3.53 (1H, bs, OH), 3.88 (6H, s), 4.09 (1H, m), 4.31 (1H, m), 5.17-5.39 (2H, m), 7.47-7.74 (3H, m), 7.93-7.99 (2H, m).

Example 5a (2R/S,3aR,4R,5R,6aS)-4-(Phenylsulfonyl)methyl-5-(triethylsilyloxy)hexahydro-2H-cyclopenta[b]furan-2-ol (mixture of two epimers) (1.74 g, 3.03 mM) was reacted in the Wittig reaction in conditions described above, with the difference that Al(t-BuO) was not added. After processing and chromatographic purification (as above), the following was obtained: mixture of (a) (1R,2R,3R,4S)-3-[(Z)-6-(4-methyl-2,6,7-trioxabicyclo[2.2.2]octan-1-yl)hex-2-enyl]-2-[(phenylsulfonyl)methyl]-4-(triethylsilyloxy)cyclopentanol (ca. 65%) and (1S,2R,3R,4R)-2-[(Z)-6-(4-methyl-2,6,7-trioxabicyclo[2.2.2]octan-1-yl)hex-2-enyl]-3-[(phenylsulfonyl)methyl]-4-(triethylsilyloxy)cyclopentanol (ca. 35%) (140 mg of the mixture, yield. 5.7%), (b) (1R,3S,4R,5R)-4-[(Z)-6-(4-methyl-2,6,7-trioxabicyclo[2.2.2]octan-1-yl)hex-2-enyl]-5-[(phenylsulfonyl)methyl]cyclopentane-1,3-diol (499 mg, 25.4%); and (c) (2R/S,3aR,4R,5R,6aS)-4-[(phenylsulfonyl)methyl]hexahydro-2H-cyclopenta[b]furano-2,5-diol

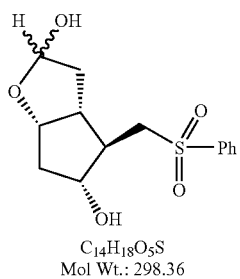

$C_{14}H_{18}O_5S$
Mol Wt.: 298.36

(mixture of isomers approx. 1:1) (127 mg, 10.1%), colorless glaze; $^1$H-NMR (CDCl$_3$; 200 MHz) δ 1.78-2.42 (5H, m), 2.48-2.75 (2H, m), 3.07 (1H, dd: 14.2, 7.5 Hz), 3.26 (1H, dd: 14.2, 6.8 Hz), 3.61 (1H, bs, OH), 3.99 (1H, m, $W_{h/2}$=14 Hz), 4.61 (1H, m, ddd: 13.5, 6.8, 4.2 Hz), 5.53 (0.5H, d: 5.1 Hz), 5.62 (0.5H, bd: 4.0 Hz), 7.41-7.72 (3H, m), 7.91-7.96 (2H, m); EI MS m/z 298 (M$^+$, 3%); $^{13}$C-NMR (CDCl$_3$; 50 MHz) δ 39.65, 39.81, 40.09, 42.38, 46.34, 47.04, 48.43, 48.51, 59.79, 60.43, 78.35, 78.46, 80.49, 83.86, 99.87, 100.8, 127.99 (2C), 129.46, 129.50, 134.01, 134.08, 138.99, 139.14; elem. analysis: for $C_{14}H_{18}O_5S$ calc. % C, 56.36; % H, 6.08; % S, 10.75. found. % C, 56.43; % H, 6.09; % S, 10.57.

Example 6

1-{(Z)-6-[(1R,2R,3R,5S)-2-((phenylsulfonyl)methyl)-3,5-bis-1-triethylsilyloxy)cyclopentyl]hex-4-enyl}-4-methyl-2,6,7-trioxabicyclo[2.2.2]octane

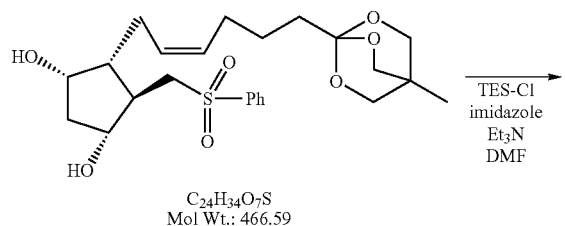

$C_{24}H_{34}O_7S$
Mol Wt.: 466.59

→ TES-Cl
imidazole
Et$_3$N
DMF

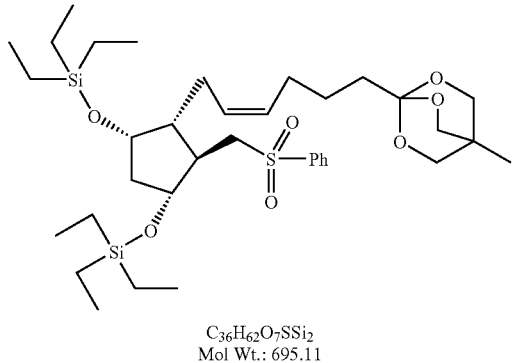

$C_{36}H_{62}O_7SSi_2$
Mol Wt.: 695.11

(1R,3S,4R,5R)-4-[(Z)-6-(4-methyl-2,6,7-trioxabicyclo[2.2.2]octan-1-yl)hex-2-enyl]-5-[(phenylsulfonyl)methyl]cyclopentane-1,3-diol (279 mg, 0.58 mM) was dissolved in anhydrous DMF (10 mL). The solution was cooled under argon to 0° C. Imidazole was added (160 mg, 2.34 mM), and then Et$_3$N (300 μL, 218 mg, 2.15 mM). The mixture was stirred at 0° C. under argon and TES-Cl (420 μL, 377 mg, 2.5 mM) was added. After 2 hours and 20 minutes, pyridine (0.50 mL) was added and the reaction mixture was transferred quantitatively to the separator containing saturated aqueous solution of NaHCO$_3$ (60 mL). It was extracted with the mixture of EtOAc-hexane (1:1; 60 mL). Layers were separated; the aqueous layer was extracted with hexane (40 mL). Organic layers were combined and extracted with saturated aqueous solution of NaHCO$_3$ (60 mL). The layers were separated, the organic layer was dried over anhydrous Na$_2$SO$_4$ (12 g). The drying agent was filtered, washed with hexane (15 mL), the combined filtrates were concentrated and dried under vacuum. The crude product obtained in this way was purified by flash chromatography on silica gel column 230-400 mesh gel (60 g), eluent 18% EtOAc in hexane+0.07% C$_5$H$_5$N. The fractions, which were pure on TCL, were combined, concentrated under vacuum and dried under vacuum (1 mm Hg, 25° C., 3 hours).

1-{(Z)-6-[(1R,2R,3R,5S)-2-((phenylsulfonyl)methyl)-3,5-bis-(triethylsilyloxy)cyclopentyl]hex-4-enyl}-4-methyl-2,6,7-trioxabicyclo[2.2.2]octane (361 mg, 87%) was obtained, as pale yellowish, thick oil; $[α]_D$=(+)9.3° (CHCl$_3$, 22° C., c=1); $^1$H-NMR (CDCl$_3$; 200 MHz) δ 0.55 (12H, 2×q: 8.0 Hz), 0.80 (3H, s), 0.92 (18H, t: 8.0 Hz), 1.39-1.72 (6H, m), 1.84 (1H, m), 1.98 (1H, m), 2.16 (4H, m), 3.19 (2H, bd: 5.3 Hz, CH$_2$SO$_2$Ph), 3.89 (6H, s), 4.14 (2H, m), 5.33 (2H, m, $W_{h/2}$=10.6 Hz), 7.50-7.68 (3H, m), 7.89-7.95 (2H, m). $^{13}$C-NMR (CDCl$_3$; 50 MHz) δ 4.69 (3C), 4.82 (3C), 6.77 (3C), 6.82 (3C), 14.49, 23.15, 25.18, 26.94, 30.12, 36.16, 43.65, 46.73, 47.15, 57.40, 71.40, 72.47 (3C), 74.74, 108.95, 127.95 (2C), 128.54, 129.08 (2C), 130.28, 133.38, 140.27; elem. analysis: for $C_{36}H_{62}O_7SSi_2$ calc. % C, 62.20; % H, 8.99. found % C, 62.04; % H, 8.68.

Example 7

1-{(Z)-6-[(1R,2R,3R,5S)-2-((phenylsulfonyl)methyl)-3,5-bis-(triethylosilyloxy)cyclopentyl]hex-4-enyl}-4-methyl-2,6,7-trioxabicyclo[2.2.2]octane and (Z)-7-[(1R,2R,3R,5S)-2-((phenylsulfonyl)methyl)-3,5-bis-(triethylsilyloxy)cyclopentyl]hept-5-enoic acid 2,2-bis(hydroxymethyl)propyl ester

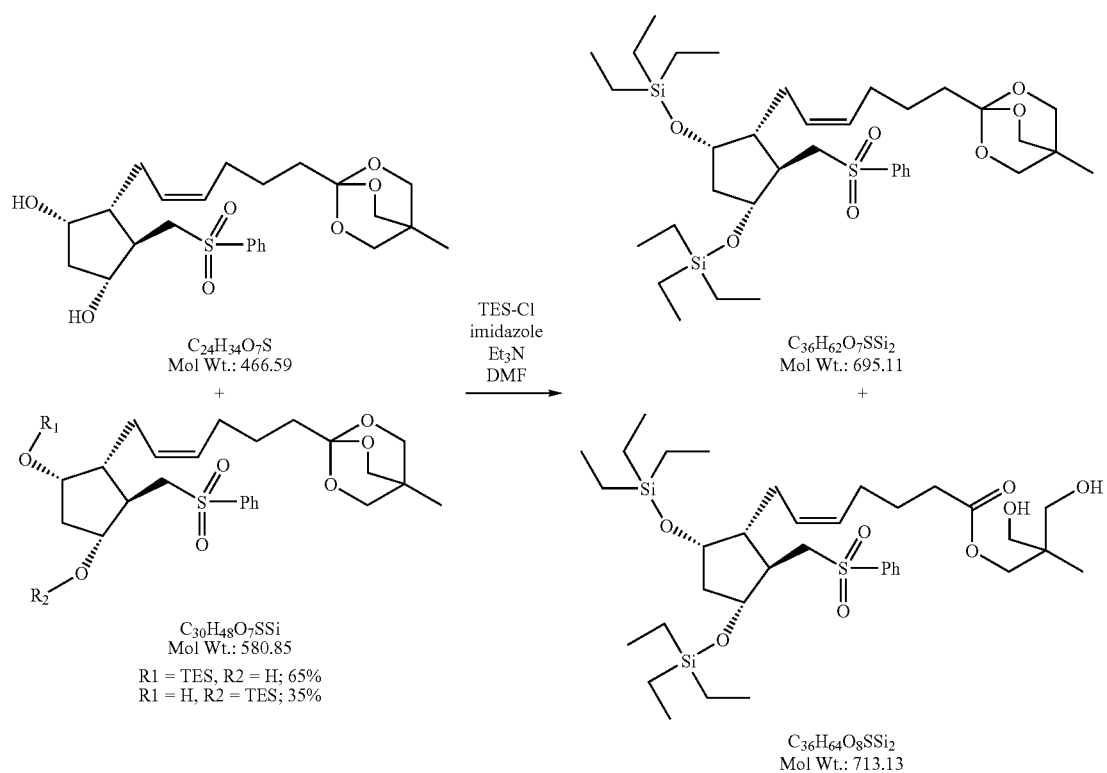

In a 100 mL flask, (1R,3S,4R,5R)-4-[(Z)-6-(4-methyl-2,6,7-trioxabicyclo[2.2.2]octan-1-yl)hex-2-enyl]-5-[(phenylsulfonyl)methyl]cyclopentane-1,3-diol (2.0 g, 4.28 mmola) and the mixture of (1R,2R,3R,4S)-3-[(Z)-6-(4-methyl-2,6,7-trioxabicyclo[2.2.2]octan-1-yl)hex-2-enyl]-2-[(phenylsulfonyl)methyl]-4-(triethylsilyloxy)cyklopentanol and (1S,2R,3R,4R)-2-[(Z)-6-(4-methyl-2,6,7-trioxabicyclo[2.2.2]octan-1-ylo)hex-2-enyl]-3-[(phenylsulfonyl)methyl]-4-(triethylsilyloxy)cyclopentanol (0.558 g, 0.961 mM) were placed. Anhydrous DMF (35 mL) was added. After dissolution, imidazole (2.396 g) was added, the mixture was cooled under argon to 0° C., Et$_3$N was added (4.20 mL), then TES-Cl (5.05) was added. After 4 hours, processing was carried out. The crude product (approx. 7 g) was maintained at +4° C. until the next day. Then, chromatographic purification was carried out similarly to Example 6 (flash chromatography on silica gel column 230-400 mesh (250 g), eluent 18% EtOac in hexane+0.07% C$_5$H$_5$N). Polar by-product was washed out with the mixture of EtOAc-hexane solvents (1:1).

After drying of pure fractions on TCL, the following compounds were obtained: (a) 1-{(Z)-6-[(1R,2R,3R,5S)-2-((phenylsulfonyl)methyl)-3,5-bis-(triethylsilyloxy)cyclopentyl]hex-4-enyl}-4-methyl-2,6,7-trioxabicyclo[2.2.2]octane (2.422 g, 66.5%), pale yellowish, thick oil; $^1$H-NMR (CDCl$_3$; 200 MHz) identical with described in Example 6, and (b) (Z)-7-[(1R,2R,3R,5S)-2-((phenylsulfonyl)methyl)-3,5-bis-(triethylsilyloxy)cyclopentyl]hept-5-enoic acid 2,2-bis(hydroxymethyl)propyl ester (1.18 g, 31.5%), colourless glaze; $^1$H-NMR (CDCl$_3$; 200 MHz) δ 0.55 (12H, 2×q: 8.0 Hz), 0.84 (3H, s), 0.93 (18H, t: 8.0 Hz), 1.42-1.82 (6H, m), 1.86-2.40 (7H, m), 3.19 (3H, m), 3.55 (4H, bs), 3.89 (1H, d:1.4 Hz), 4.12 (3H, m), 5.39 (2H, m, W$_{h/2}$=34 Hz), 7.51-7.68 (3H, m), 7.89-7.94 (2H, m).

Example 8

Preparation of Omega Chain Synthones of General Formula (VI), of High Enantiomeric Excess

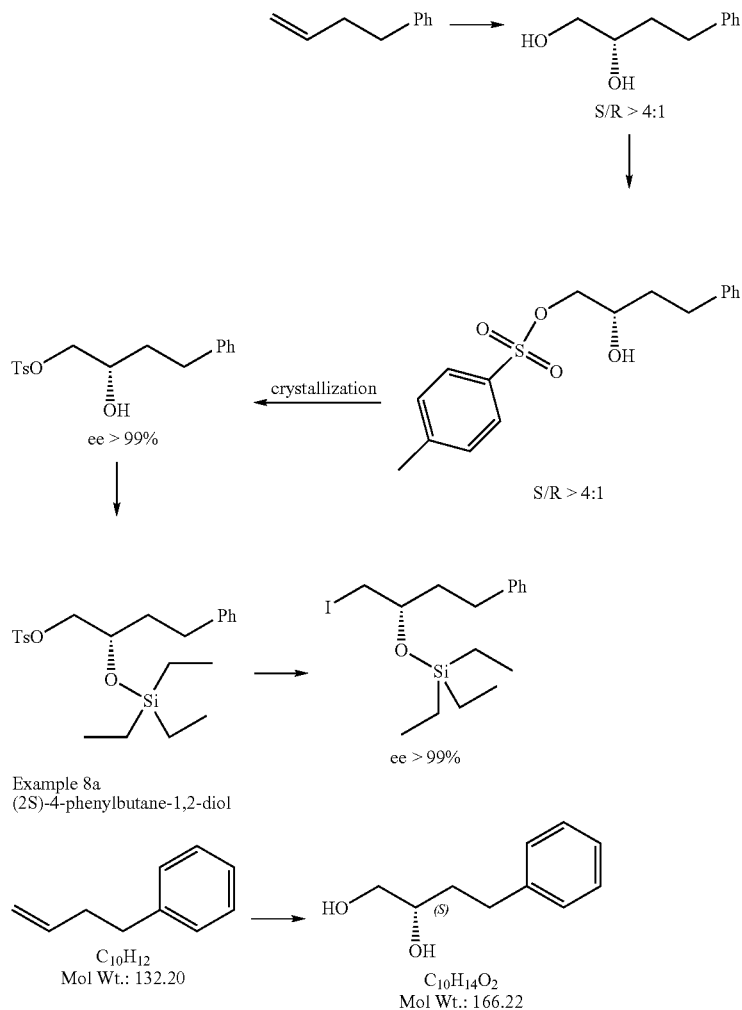

Example 8a
(2S)-4-phenylbutane-1,2-diol

In a 2 L three-neck flask, t-butanol (450 mL), distilled water (450 mL), (DHQ)$_2$AQN (Aldrich, 95%; 990 mg, 1.10 mM), K$_3$Fe(CN)$_6$ (93.1 g, 280 mM), K$_2$CO$_3$ (38.7 g, 280 mM) and K$_2$OsO$_2$(OH)$_4$ (133 mg, 0.36 mM) were placed. The mixture was stirred at room temperature over 1.5 h, then cooled to 0° C. (ice-water bath). Then, 4-phenyl-butene (11.90 g, 13.52 mL, 90.0 mM) was added and stirring was continued at 0° C. After 17 hours, upon continuation of stirring and cooling at 0° C., Na$_2$S$_2$O$_5$ (130 g, 680 mM) was added. Cooling bath was removed and stirring was continued, allowing the mixture to heat to room temperature. After 1 hour, EtOAc (400 mL) was added, vigorous stirring was carried out for 10 minutes, then phases were separated; the aqueous phase was extracted with EtOAc (100 mL); organic phases were combined and dried over Na$_2$SO$_4$ (100 g). Then the drying agent was filtered and washed with EtOAc (100 mL). The combined filtrates were concentrated under vacuum, nearly completely removing the solvents. Yellow oil obtained in this way was purified by flash chromatography on silica gel column (350 g), EtOAc as eluent. Fractions pure on TLC were concentrated and dried under vacuum (1 mm Hg, 30° C., 1 hour).

As a result, (2S)-4-phenyl-1,2-butanediol (14.70 g, 98%) was obtained as pale yellowish, thick oil; $^1$H-NMR (CDCl$_3$; 200 MHz) δ 1.72 (2H, m, W$_{h/2}$=23 Hz), 2.70 (2H, m, W$_{h/2}$=42 Hz), 3.31 (2H, bs, 2×OH), 3.42 (1H, dd: 11.2, 7.7 Hz), 3.61 (1H, dd: 11.2, 2.9 Hz), 3.69 (1H, m, W$_{h/2}$=18 Hz), 7.13-7.31 (5H, m); $^{13}$C-NMR (CDCl$_3$; 50 MHz) δ 31.8, 34.6, 66.6, 71.5, 125.8, 128.2 (2C), 128.3 (2C), 141.5. Analysis of this sample, by use of chiral HPLC chromatography, was carried out on Chiracel OD column (250+20)×4.6 mm, 10 μm, eluent: hexane (80% vol)-2-propanol (20% vol), flow rate 1.0 mL/min.: R$_t$ 8.47 min. (17.2%), R$_t$ 11.06 min. (81.9%), enantiomeric excess ee=65.3%. As a standard for calibration of HPLC measurement, racemic 4-phenylbutane-1,2-diol was used, prepared from 4-phenyl-1-butene in the hydroxylation reaction according to the above procedure, in which DABCO was used instead of (DHQ)$_2$AQN).

Example 8b (S)-2-hydroxy-4-phenylbutyl 4-methylbenzenesulfonate

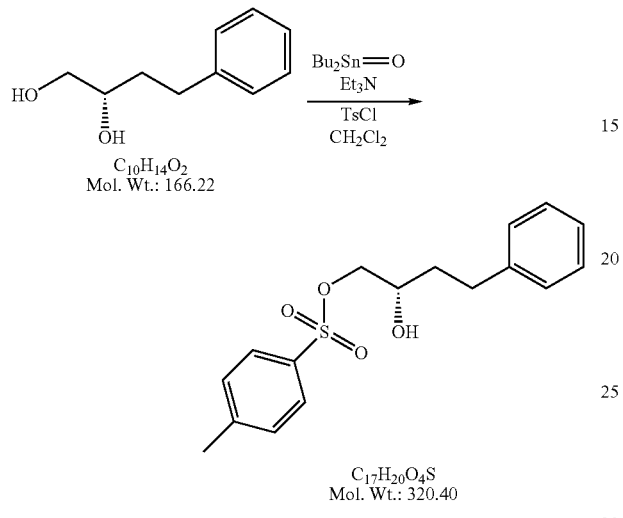

(2S)-4-Phenyl-1,2-butanediol (13.58 g, 81.7 mM) was dissolved in anhydrous CH$_2$Cl$_2$ (190 mL). To this solution, stirred under argon, Bu$_2$SnO (720 mg, 2.89 mM) was added. The suspension was stirred for 5 minutes, then Et$_3$N was added (11.40 mL, 8.276 g, 81.79 mM) and, upon continuation of stirring, the reaction mixture was cooled to 0° C., then p-toluenesulfonyl chloride was added (16.03 g, 84.08 mM). The whole was stirred at 0° C. for 5 more minutes; then the cooling bath was removed and stirring was continued under argon, allowing for slow warming of the mixture to room temperature. After 1.5 h, the mixture was put away at +4° C. for 18 hours. Then the mixture was concentrated to the volume of 100 mL and injected on flash chromatographic silica gel column 230-400 mesh (500 g). As a mobile phase, the solution of 25% EtOAc in hexane was used. On the basis of TLC analysis, the pure fractions were combined, concentrated and dried under vacuum (1 mm Hg, 30° C., 2 hours).

Partly racemic (3S)-1-phenyl-3-hydroxy-4-p-toluenesulfonyloxybutane was obtained (20.10 g, 76.8%) as colorless, thick oil; $^1$H-NMR (CDCl$_3$; 200 MHz) δ 1.73 (2H, m), 2.19 (1H, d: 4.6 Hz, OH), 2.45 (3H, s), 2.70 (2H, m), 3.85 (2H, m), 4.02 (1H, dd: 9.5, 2.9 Hz), 7.11-7.37 (7H, m), 7.79 (2H, ddd: 8.4, 2.0, 1.8 Hz); $^{13}$C-NMR (CDCl$_3$; 50 MHz) δ 21.6, 31.3, 34.1, 68.5, 73.8, 125.9, 127.8 (2C), 128.2 (2C), 128.3 (2C), 129.8 (2C), 132.4, 140.9, 144.9. Analysis of this sample, with use of chiral HPLC chromatography, was carried out on Chiracel OD column (250+20)×4.6 mm, 10 µm, eluent: hexane (80% vol)-2-propanol (20% vol), flow rate 1.0 mL/min.: R$_t$ 13.10 min. (83.7%), R$_t$ 15.53 min. (16.14%), enantiomeric excess ee=67.7%.

This sample of tosylate (ee=67.7%; 19.85 g) was crystallized from Et$_2$O (60 mL). The prepared crystalline product (10.51 g) was crystallized twice with Et$_2$O in analogical conditions. As a result of these operations, optically pure (ee=99.26%) (3S)-1-phenyl-3-hydroxy-4-p-toluenesulfonyloxybutane was prepared (4.77 g, 18.45%) as colorless needles, m.p. 68-69° C.; [α]$_D$=(+) 0.70° (CHCl$_3$, 25° C., c=1); $^1$H-NMR (CDCl$_3$; 200 MHz), spectrum identical with that described above. Analysis of this sample, with use of chiral HPLC chromatography, was carried out on Chiracle OD column (250+20)×4.6 mm, 10 µm, eluent: hexane(80% vol)-2-propanol (20% vol), flow rate 1.0 mL/min.: R$_t$ 13.28 min. (99.59%), R$_t$ 15.88 min. (0.37%), enantiomeric excess ee=99.26%; elem. analysis: for C$_{17}$H$_{20}$O$_4$S calc. % C, 63.73; % H, 6.29; % S, 10.01. found. % C, 63.79; % H, 6.19; % S, 10.16.

Example 8c (S)-2-(Triethylsilyloxy)butyl 4-methylbenzenesulfonate

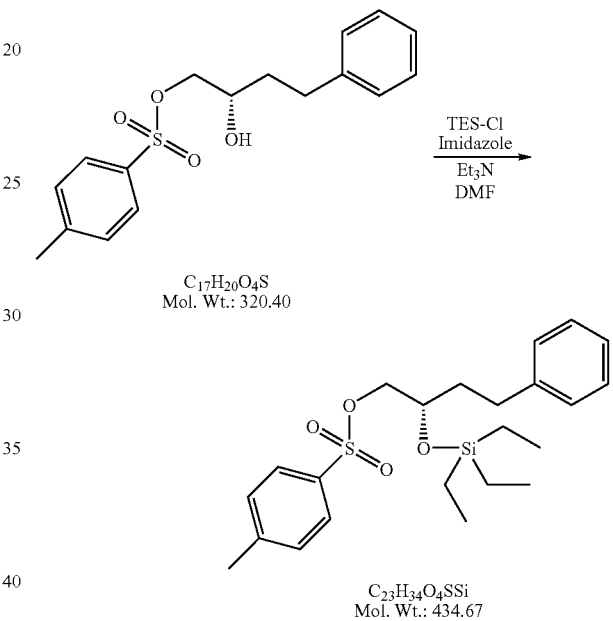

(3S)-1-Phenyl-3-hydroxy-4-p-toluenesulfonyloxybutane (ee=99.26%; 4.537 g, 14.16 mM) was dissolved in anhydrous DMF (38 mL). The solution was cooled under argon to 0° C., imidazole (1.069 g) and Et$_3$N (2.00 mL) were added. The mixture was vigorously stirred under argon at 0° C. and TES-Cl was added dropwise (2.52 mL). The mixture was stirred at 0° C. for 1 hour, then at room temperature for 20 minutes, then hexane was added (100 mL) and saturated aqueous solution of NaHCO$_3$ (90 mL). After extraction, the layers were separated, the aqueous layer was again extracted twice extracted with hexane (2×40 mL). The combined aqueous layers were extracted with aqueous solution of NaHCO$_3$ (100 mL). The layers were separated, the organic layer was dried over Na$_2$SO$_4$ (20 g). The drying agent was filtered and washed on the filter with hexane (20 mL). The combined filtrates were concentrated and dried under vacuum to give an oil (7.0 g), which was purified by flash chromatography on silica gel column 230-400 mesh (185 g), eluent: 10% EtOAc in hexane. Fractions, which were pure on TLC, were combined, concentrated and dried under vacuum (1 mm Hg, 27° C.; 2 hours).

(3S)-1-Phenyl-4-p-toluenesulfonyloxy-3-triethylsilyloxybutane (6.127 g, 99.5%) was obtained as colorless, thick oil; [α]$_D$=(+)4.9° (CHCl$_3$, 25° C., c=1); $^1$H-NMR (CDCl$_3$; 200

MHz) δ 0.56 (6H, q: 8.0 Hz), 0.91 (9H, t: 8.0 Hz), 1.74 (2H, m), 2.44 (3H, s), 2.60 (2H, m), 3.90 (3H, bs), 7.09-7.36 (7H, m), 7.78 (2H, ddd: 8.4, 2.0, 1.8 Hz); $^{13}$C-NMR (CDCl$_3$; 50 MHz) δ 4.8 (3C), 6.8 (3C), 21.6, 31.0, 35.8, 69.4, 72.8, 125.8, 127.8 (2C), 128.1 (2C), 128.3 (2C), 129.7 (2C), 132.7, 141.4, 144.7; Elem. analysis: for C$_{23}$H$_{34}$O$_4$SSi calc. % C, 63.55; % H, 7.88; % S, 7.38. found. % C, 63.62; % H, 7.72; % S, 7.40.

Example 8d (3S)-1-Phenyl-4-iodo-3-triethylsilyloxybutane

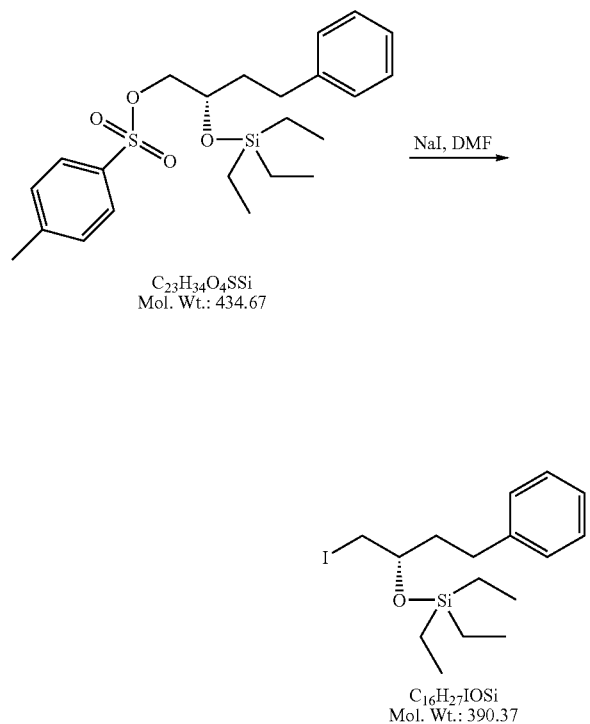

Example 8d.1

(3S)-1-Phenyl-4-p-toluenesulfonyloxy-3-triethylsilyloxybutane (ee=99.26%; 3.145 g; 7.23 mM) was dissolved in anhydrous DMF (30 mL). The solution was stirred vigorously at room temperature under argon and sodium iodide was added (4.60 g, 30.7 mM). Upon vigorous stirring, content of the flask was heated to +80° C. under argon. After 2 hours, the mixture was cooled to room temperature, saturated aqueous solution of NaHCO$_3$ (70 mL) and hexane (70 mL) was added. Phases were separated after extraction. The aqueous phase was extracted with hexane twice (2×40 mL). The combined organic layers were extracted with hexane (2×40 mL). The combined organic layers were extracted with aqueous solution of NaHCO$_3$ (70 mL), then dried over Na$_2$SO$_4$ (16 g), the drying agent was filtered, washed with hexane (15 mL), the combined filtrates were concentrated and dried under vacuum. Pale yellowish oil was obtained (2.88 g), which was purified by flash chromatography on silica gel column 230-400 mesh (100 g), eluent: 3-10% EtOAc in hexane.

After drying (1 mm Hg, 25° C., 2 hours) of pure fractions on TCL, the following compounds were obtained: (a) (3S)-1-phenyl-4-iodo-3-triethylsilyloxybutane (ee=99.2%; 2.423 g, 85.8%), colourless oil; [α]$_D$=(−)9.1° (CHCl$_3$, 20° C., c=1); $^1$H-NMR (CDCl$_3$; 200 MHz) δ 0.62 (6H, q: 7.6 Hz), 0.98 (9H, t: 7.6 Hz), 1.78 (2H, m), 2.65 (2H, m), 3.23 (2H, dd: 5.1, 0.6 Hz), 3.66 (1H, m), 7.14-7.33 (5H, m); $^{13}$C-NMR (CDCl$_3$; 50 MHz) δ 5.05 (3C), 6.90 (3C), 13.25, 31.26, 38.61, 71.01, 125.73, 128.16 (2C), 128.25 (2C), 141.58; HR ESI MS for C$_{16}$H$_{27}$IOSiNa calc. (M+Na$^+$) m/z 413.07736, found. 413.0764, and (b) (3S)-1-phenyl-4-p-toluenesulfonyloxy-3-triethylsilyloxybutane (recovered substrate; 317 mg, 10.1%); $^1$H-NMR (CDCl$_3$; 200 MHz) identical with cited above for this compound.

Example 8d.2

(3S)-1-Phenyl-4-p-toluenesulfonyloxy-3-triethylsilyloxybutane (ee=99.26%; 5.90 g; 13.57 mM) was dissolved in anhydrous DMF (60 mL). The solution was stirred vigorously at room temperature under argon and sodium iodide was added (8.8 g, 58.7 mM). Upon vigorous stirring, the content of the flask was heated to +85° C. under argon. After 3 hours, lack of substrate and presence of unexpected polar product was determined by TLC in the amount approximately 50%. The reaction mixture was cooled to room temperature, diisopropyl ether (70 mL) and H$_2$O (120 mL) were added. After extraction, the phases were separated, the aqueous phase was extracted twice with diisopropyl ether (2×50 mL). The organic phases were combined and extracted with H$_2$O (80 mL), the organic phase was dried over Na$_2$SO$_4$ (22 g). The drying agent was filtered and washed with diisopropyl ether (25 mL). The filtrates were combined, concentrated and dried under vacuum to the mass of 5.51 g (crystallizing oil).

This sample was dissolved in anhydrous DMF (40 mL). The solution was cooled under argon to 0° C., then imidazole was added (1.63 g; 23.9 mM). The mixture was stirred until dissolution, then TES-Cl was added (2.0 mL, 11.9 mM). The solution was stirred under argon in 0° C. After 30 minutes, the cooling bath was removed and stirring was continued while allowing the sample to heat to room temperature. After the complete reaction time of 1 hour, diisopropyl ether (100 mL) and then saturated aqueous solution of NaHCO$_3$ were added (150 mL). The mixture was transferred to the separator. The phases were separated after extraction, the aqueous phase was extracted twice with diisopropyl ether (2×50 mL).

The organic phases were combined and extracted with saturated aqueous solution of NaHCO$_3$ (100 mL). The organic phase was dried over anhydrous Na$_2$SO$_4$ (25 g), the drying agent was filtered and washed with diisopropyl ether. The filtrates were combined and concentrated under vacuum. The crude product was purified by flash chromatography on silica gel column 230-400 mesh (200 g), eluent: 2% EtOaAc in hexane. After drying (1 mm Hg, 25° C., 2 hours) of the pure fractions on TLC, the following compounds were obtained: (a) (3S)-1-phenyl-4-iodo-3-triethylsilyloxybutane (ee=99.2%; 5.09 g, 96%), colorless oil; [α]$_D$=(−)9.1°; $^1$H-NMR (CDCl$_3$; 200 MHz): spectrum identical with that described in Example 8d. 1.

Example 8e

(3S)-1-Phenyl-4-p-toluenesulfonyloxy-3-triethylsilyloxybutane and (3S)-1-phenyl-4-iodo-3-triethylsilyloxybutane

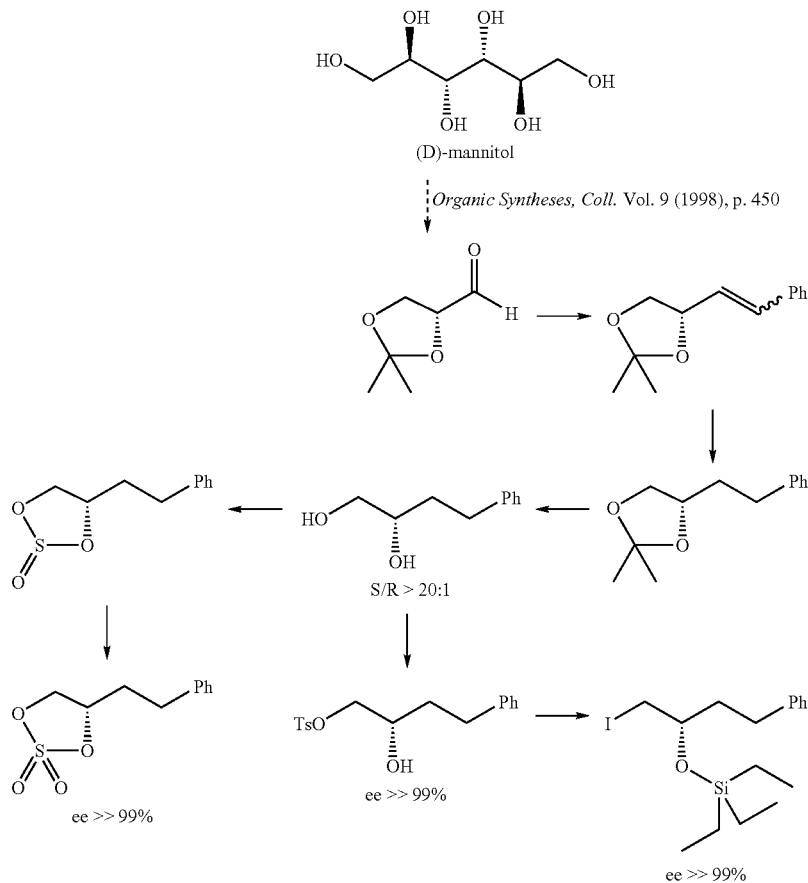

2,3-O-Isopropylidene derivative of (R)-glyceric aldehyde was prepared from D-mannitol according to the procedure described in the publication of C. R. Schid et al., Organic Syntheses, Coll. Vol. 9 (1998), 450. The obtained aldehyde was distilled directly prior use in the reaction described in Example 8e.1 (boiling temperature: 47-51° C./20 mm Hg).

Example 8e.1

(E/Z,4S)-2,2-Dimethyl-4-styryl-[1,3]dioxolane

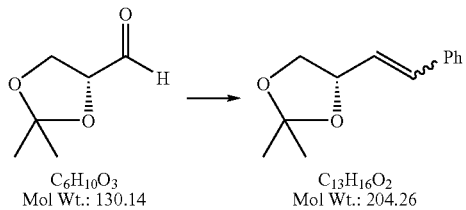

In a 2 L three-necked flask, provided with a magnetic stirrer, a thermometer, a dropper with pressure compensation and argon inlet, tetrahydrofurane (1.21 L) and benzyltriphenylphosphonium bromide (189.4 g, 0.437 mM) were placed. The suspension was vigorously stirred in argon atmosphere and cooled to 0° C. Then, 2.5 M solution of hexyllithium in hexane (170 mL, 0.425 M), maintaining the temperature of the mixture below 5° C. Over 1 hour, the mixture was heated to 15° C., stirred for 30 minutes at this temperature, then cooled to 0° C. Then, the cooled below 5° C. solution of freshly distilled 2,2, —O-isopropylidene derivative of (R)-glyceryl aldehyde (52.3 g, 0.402 M) in tetrahydrofurane (150 mL) was added dropwise. After completion of dropwise addition, the mixture was heated to 20° C. and stirred at this temperature for 2 hours, then methanol (10 mL) was slowly added. The prepared suspension was filtered through Celite (100 g), the solid was washed twice with the mixture of hexane-EtOAc (2:1; 2×200 mL). The combined filtrates were concentrated under vacuum to viscous oil, which was then purified by flash chromatography on silica gel column 230-400 mesh (500 g). Eluent: hexane-EtOAc (1:1).

After concentration of pure fractions and drying under vacuum, (E/Z,4S)-2,2-dimethyl-4-styryl-[1,3]dioxolanes were prepared (mixture of isomers; 50.9 g, 62%); colourless, thick oil; $^1$H-NMR (CDCl$_3$; 200 MHz) δ 1.39 (2.3H, s, CH$_3$), 1.43 (0.7H, s, CH$_3$), 1.47 (3H, bs, CH$_3$), 3.68 (1H, m), 4.08 (0.3H, m), 4.16 (0.7H, m), 4.67 (0.3H, m), 4.92 (0.7H, m), 5.70 (0.7H, dd: 11.6, 9.0 Hz), 6.16 (0.3H, dd: 15.8, 7.6 Hz), 6.70 (1H, m), 7.23-7.42 (5H, m); $^{13}$C-NMR (CDCl$_3$; 50

MHz) δ 25.89, 25.94, 26.75, 26.86, 69.51, 69.70, 72.41, 77.24, 109.37, 109.43, 126.61, 126.71, 127.52, 127.98, 128.29, 128.57, 128.70, 129.20, 133.38, 133.97, 136.13, 136.24.

Example 8e.2

(4S)-2,2-Dimethyl-4-phenetyl-[1,3]dioxolane

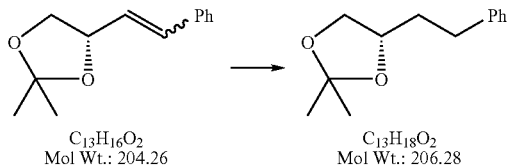

The mixture of (E)/(Z) (4S)-2,2-dimethyl-4-styryl-[1,3] dioxolanes (50.0 g) was dissolved in methanol (0.50 L). The solution was placed in autoclave (Parr, 1.6 L), 10% Pd/C catalyst was added (5.0 g). Hydrogenation was carried out under the pressure of 10 bars, at the temperature of 30° C., for 24 hours. The catalyst was filtered and washed three times with methanol (3×50 mL). The filtrates were combined and concentrated under vacuum, then dried under vacuum. (4S)-2,2-dimethyl-4-phenethyl-[1,3]dioxolane (49.9 g, 98.8%) was obtained as colourless oil; $[\alpha]_D$=(+)3.8° (CHCl$_3$, 20° C., c=1); $^1$H-NMR (CDCl$_3$; 200 MHz) δ 1.36 (3H, bs), 1.43 (3H, bs), 1.88 (2H, m, W=66 Hz), 2.70 (2H, m, W=57 Hz), 3.52 (1H, dd: 7.5, 7.0 Hz), 4.05 (2H, m, W=39 Hz), 7.14-7.33 (5H, m); $^{13}$C-NMR (CDCl$_3$; 50 MHz) δ 25.73 (CH$_3$), 26.99 (CH$_3$), 32.02 (CH$_2$), 35.33 (CH$_2$), 69.31 (CH$_2$), 75.35 (CH), 108.71 (quat. C), 125.95 (CH), 128.35 (2×CH), 125.41 (2×CH), 141.53 (quat. C).

Example 8e.3

(S)-4-Phenylbutane-1,2-diol

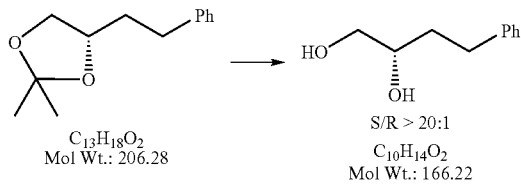

(4S)-2,2-Dimethyl-4-phenetyl-[1,3]dioxolane, obtained according to example 8e.2 (49.8 g, 0.241 mM) was dissolved in methanol (0.60 L), p-toluenesulfonic acid (0.50 g) was added and stirring was carried out at 40° C. for 4 hours. Then, Et$_3$N (2 mL) was added to the mixture and the solvent was evaporated under vacuum. The prepared oil was purified by flash chromatography silica gel column (500 g), EtOAc was used as eluent. (S)-4-Phenylbutane-1,2-diol (40.0 g, 99%) was obtained as colorless, thick oil, solidifying at +4° C.; m.p.=34-36° C.; $[\alpha]_D$=(−)13.6° (CHCl$_3$, 20° C., c=1); $[\alpha]_D$= (−)33.1° (EtOH, 20° C., c=1); $^1$H-NMR (CDCl$_3$; 200 MHz): spectrum identical with spectrum described for (3S)-t-phenyl-3,4-butanediol in Example 8a.

Analysis of this sample by chiral HPLC chromatography was carried on Chiracel OD column (250+20)×4.6 mm, 10 μm, eluent: hexane (80% vol)-2-propanol (20% vol), flow rate 1.0 mL/min.: R$_t$ 8.5 min. (0.33%), R$_t$ 11.1 min. (98.86%), ee=99.3%. In order to calibrate HPLC measurement, racemic 4-phenyl-1,2-butanediol was used, as in Example 8a above.

Example 8e.4

(S)-2-Hydroxy-4-phenylbutyl 4-methylbenzenesulfonate

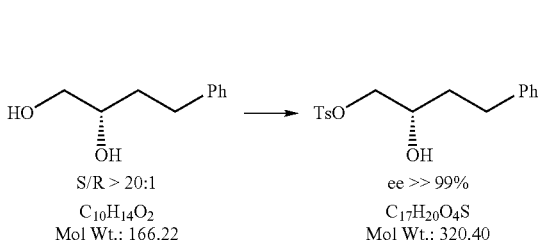

Example 8e.4

(S)-4-Phenyl-3,4-butane-1,2-diol obtained according to procedure described in Example 8e.3 of enantiomeric excess ee=99.3% (40 g) was subjected to the reaction of monotosylation, as in Example 8b. After processing, the mixture was concentrated to 200 mL vol and injected on flash chromatographic column with silica gel 230-400 mesh (1000 g). As a mobile phase, the solution of 25% EtOAc in hexane was used. (3S)-1-Phenyl-3-hydroxy-4-p-toluenesulfonyloxybutane was obtained (60 g, 77.8%) as colourless, thick oil; $^1$H-NMR (CDCl$_3$; 200 MHz): spectrum identical with that described in Example 8.b. This sample of tosylate (ee=99.7%) was crystallized from Et$_2$O (V$_{Et2O}$: m=3.5). Crystalline (S)-2-hydroxy-4-phenylbutyl 4-methylbenzenesulfonate was obtained (52 g, 67.4%) as colourless needles; $[\alpha]_D$=(+) 1.0° (CHCl$_3$, 20° C., c=1). Analysis of this sample by chiral HPLC chiral chromatography was carried out on Chiracel OD column OD (250+20)×4.6 mm, 10 μm, eluent: hexane (80% obj.)-2-propanol (20% obj.), flow rate 1.0 mL/min.: R$_t$ 13.2 min. (98.37%), R$_t$ 15.9 min. (0.039%); ee=99.92%.

Example 8e.5

(S)-2-(Triethylsilyloxy)-4-phenylbutyl and (S)-1-phenyl-4-iodo-3-(triethylsilyloxy)butane 4-methylbenzenesulfonate

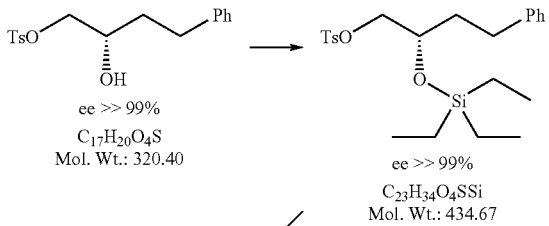

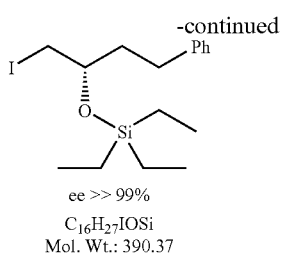

ee >> 99%
C$_{16}$H$_{27}$IOSi
Mol. Wt.: 390.37

Example 8e.5

Crystalline (S)-2-hydroxy-4-phenylbutyl 4-methylbenzenesulfonate (ee=99.92%, 10.0 g) was silylated with chlorotriethylsilane according to the procedure described in Example 8c. (S)-2-(Triethylsilyloxy)-4-phenylbutyl 4-methylbenzenesulfonate (13.43 g, 99%); ee=99.2%; spectrum $^1$H-NMR identical with that described for this compound in Example 8c, was obtained. This sample of (3S)-1-phenyl-4-p-toluenesulfonyloxy-3-triethylsilyloxybutane (13.2 g) was reacted with NaI/DMF according to the procedure described in Example 8d.1, while heating at 75-80° C. was carried out for 2.5 h. After processing and chromatographic purification, as in Example 8d.1, (S)-1-phenyl-4-iodo-3-(triethylsilyloxy)butane was prepared (10.55 g, 89%); ee=99.92%; spectrum $^1$H-NMR identical with that described for this compound in Example 8d.

Example 8.f (2R/S, 4S)-4-Phenethyl-[1,3,2]dioxathiolate-2-oxide

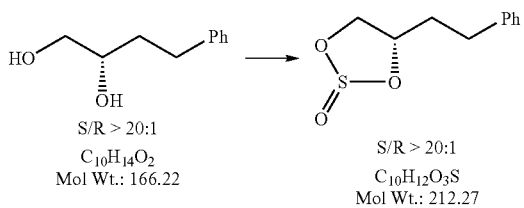

S/R > 20:1
C$_{10}$H$_{14}$O$_2$
Mol Wt.: 166.22

S/R > 20:1
C$_{10}$H$_{12}$O$_3$S
Mol Wt.: 212.27

To a 1 L round-bottom flask, provided with a magnetic stirrer, a thermometer, argon inlet and a dropper with pressure compensation, 13.4 g of (S)-4-phenylbutane-1,2-diol (ee=99.92%) and 600 mL if dichloromethane were added, and stirring was continued for 5 minutes. The solution of 28.2 mL of N,N-diisopropyylethylamine was added, the mixture was cooled to 5° C. Then, over 10 minutes, thionyl chloride (6.20 mL) was added dropwise under the surface of the solution, so that the temperature was maintained in the range of 0-5° C. Stirring was continued at this temperature for 1 hour. The reaction mixture was poured into 500 mL of 0.1 M phosphate buffer of pH 7.2 of the temperature of 0° C. Organic layer was separated and washed with 500 mL of 2% NaCl solution. The mixture was dried with anhydrous sodium sulfate, concentrated and dried under the reduced pressure.

The cyclic sulfite of (2R/S, 4S)-4-phenethyl-[1,2,3]dioxathiolate-2-oxide in the from of an oil (16.5 g, 96% yield), two diastereoisomers (approx. 1:1) was obtained; $^1$H-NMR (200 MHz, CDCl$_3$) δ: 1.83-2.38 (2H, m), 2.62-2.97 (2H, m), 3.90 (0.5H, dd: 8.1, 6.8 Hz), 4.24-4.52 (1H, m), 4.62 (0.5H, dd: 8.5, 6.4 Hz), 4.87-5.00 (0.5H, m), 7.16-7.35 (5H, m); $^{13}$C-NMR (50 MHz, CDCl$_3$) δ: 31.58, 31.99, 34.09, 35.13, 70.20, 71.50, 79.41 (CH), 82.98 (CH), 126.45, 126.49, 128.42, 128.46, 128.6, 128.70, 140.06, 140.16.

Example 8.g (S)-4-Phenethyl-[1,3,2]dioxathiolate-2,2-dioxide

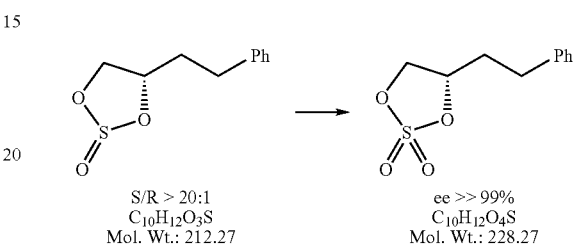

S/R > 20:1
C$_{10}$H$_{12}$O$_3$S
Mol. Wt.: 212.27 ee >> 99%
C$_{10}$H$_{12}$O$_4$S
Mol. Wt.: 228.27

To the vigorously stirred solution of (2R/S, 4S)-4-phenethyl-[1,3,2]dioxathiolate-2-oxide prepared according to the procedure described in Example 8.f (7.8 g) in 100 mL of acetonitrile, 11.0 g of sodium periodate, 81 mg of ruthenium chloride hydrate RuCl$_3$×3H$_2$O and 20 mL of water were added. The reaction mixture heated from 20° to approx. 40° C. over 10 minutes, and after this time complete oxidation of sulfite to sulfate was found on the basis of TLC (hexane/AcOEt 2:1). After cooling to the temperature of 20° C., 100 mL of diethyl ether and 80 mL of water were added. Layers were separated, aqueous phase was extracted with Et$_2$O (2×100 mL). The combined ether solutions were dried over anhydrous sodium sulfate, the solvents were evaporated under the reduced pressure. 7.9 g of dark precipitate was obtained, which was crystallized from 20 mL of Et$_2$O. (S)-4-Phenethyl-[1,3,2]dioxathiolate-2,2-dioxide was obtained (3.5 g, 42%); white crystals, t.t.=50-51° C.; [α]$_D$=(−)42.9° (MeOH, 20° C., c=1); IR (KBr) 651, 702, 757, 783, 853 (s), 965 (s), 1013, 1038, 1210 (s), 1381 (s), 1602 cm$^{-1}$; $^1$H-NMR (200 MHz, CDCl$_3$) δ: 1.93-2.11 (1H, m), 2.19-2.37 (1H, m), 2.65-2.94 (2H, m), 4.28 (1H, t: 8.1 Hz), 4.60 (1H, dd: 9.0, 6.0 Hz), 4.85-4.98 (1H, m), 7.16-7.38 (5H, m); $^{13}$C-NMR (50 MHz, CDCl$_3$) δ: 30.73, 33.86, 72.68, 81.99 (CH), 126.68, 128.31, 128.76, 139.07. Elem. analysis: for C$_{10}$H$_{12}$O$_4$S calc. % C, 52.62; % H, 5.30; % S, 14.05. found. % C, 52.66; % H, 5.34; % S, 14.09.

Analysis of this sample by chiral HPLC chromatography was carried out on Chiracel OD column (250+20)×4.6 mm, 10 μm, eluent: hexane (85% vol)-2-propanol (15% vol), flow rate 1.0 mL/min.: R$_t$ 41.0 min. (100%), peak of the second isomer was not found; and also on Chiracel AD column (250+20)×4.6 mm, 10 μm, eluent: hexane (85% vol)-2-propanol (15% vol), flow rate 1.0 mL/min.: R$_t$ 10.5 min. (100%), peak of the second isomer was not found; ee=approx. 100%.

Example 8.h

(S)-1,2-Epoxy-4-phenylbutane

Example 8.h.1

(S)-4-phenyl-1-iodobutan-2-ol

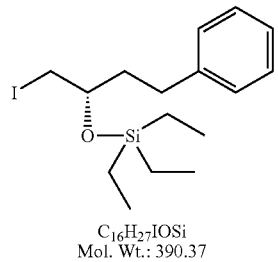

C$_{16}$H$_{27}$IOSi
Mol. Wt.: 390.37

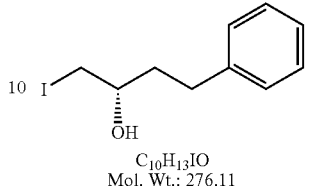

C$_{10}$H$_{13}$IO
Mol. Wt.: 276.11

(S)-1-Phenyl-4-iodo-3-triethylsilyloxybutane of enantiomeric excess ee=99.2% (3.52 g, 9.0 mM) was dissolved in acetone (20 mL). H$_2$O was added (2 mL). The solution was stirred at 20° C. under argon and pyridinium p-toluenesulfonate was added (200 mg). After 20 hours, the mixture was poured on 3% aqueous solution of NaHCO$_3$ (150 mL), and the mixture of Et$_2$O-EtOAc was added (1:1, 100 mL). After extraction, the layers were separated, the organic layer was dried over Na$_2$SO$_4$ (15 g), the drying agent was filtered and washed with EtOAc (20 mL). The filtrates were combined and concentrated under vacuum. The prepared oil was purified by flash chromatography on silica gel column 230-400 mesh, 120 g, eluent: 15% EtOAc/hexane. The obtained fractions, which were pure on TLC, were concentrated to the volume of 10 mL and put away at 0° C. for 2 hours.

The obtained crystals were filtered and dried. (S)-4-Phenyl-1-iodobutane was obtained (1.80 g, 72%), white needles, t.t.=° C.; [α]$_D$=(−)15.8° (CHCl$_3$, 20° C., c=1); $^1$H-NMR (200 MHz, CDCl$_3$) δ: 1.87 (2H, m), 2.74 (2H, m), 3.24 (1H, dd: 10.2, 6.8 Hz), 3.38 (1H, dd: 10.1, 3.5 Hz), 3.52 (1H, m, W=28 Hz), 7.15-7.34 (5H, m); $^{13}$C-NMR (50 MHz, CDCl$_3$) δ: 16.59, 31.91, 38.14, 70.12, 126.07, 128.42 (2C), 128.50 (2C), 141.26. Elem. analysis: for C$_{10}$H$_{13}$IO$_3$ calc. % C, 43.50; % H, 4.75; % I, 45.96. found. % C, 43,49; % H, 4,61; % I, 46.00.

Analysis of this sample by chiral HPLC chromatography was carried out on Chiracel OD column (250+20)×4.6 mm, 10 μm, eluent: hexane (85% vol)-2-propanol (15% vol), flow rate 1.0 mL/min.: R$_t$ 8.20 min. (99.867%), R$_t$ 11.1 (0.073%); ee=99.85%.

Example 8.h.2

(S)-1,2-Epoxy-4-phenylbutane

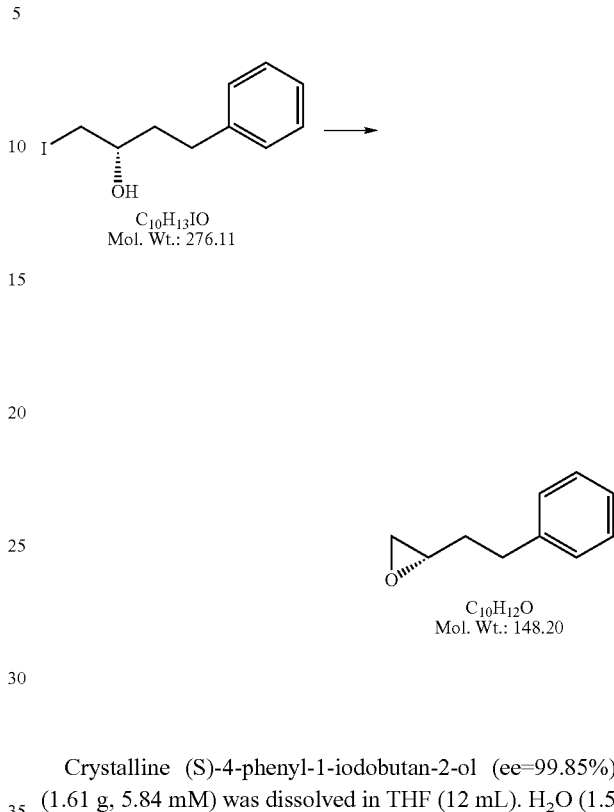

C$_{10}$H$_{13}$IO
Mol. Wt.: 276.11

C$_{10}$H$_{12}$O
Mol. Wt.: 148.20

Crystalline (S)-4-phenyl-1-iodobutan-2-ol (ee=99.85%) (1.61 g, 5.84 mM) was dissolved in THF (12 mL). H$_2$O (1.5 mL) and solid KOH (1.95 g) were added. The reaction mixture was stirred at 20° C. under argon. After 7 hours, the mixture was quantitatively transferred to the separator, in which brine (50 mL), water (100 mL) and Et$_2$O (120 mL) were previously placed. After extraction, the phases were separated, the organic phase was extracted with H$_2$O (150 mL), the organic phase was dried over anhydrous Na$_2$SO$_4$ (20 g, 0° C., 16 hours), the drying agent was filtered and washed with Et$_2$O (20 mL), the filtrates were combined and concentrated at 0° C., then they were dried (10° C., 5 mm Hg, 15 minutes).

(S)-1,2-Epoxy-4-phenylbutane was obtained as pale yellowish oil; [α]$_D$=(−)19.9° (CHCl$_3$, 20° C., c=1); $^1$H-NMR (200 MHz, CDCl$_3$) δ: 1.79-1.92 (2H, m), 2.47 (1H, dd: 4.9, 2.6 Hz), 2.66-2.87 (3H, m), 2.91-3.00 (1H, m), 7.15-7.34 (5H, m); $^{13}$C-NMR (50 MHz, CDCl$_3$) δ: 32.25, 34.29, 47.25 (CH$_2$), 51.79 (CH), 126.02, 128.38 (2C), 128.45 (2C), 141.26. Elem. analysis: for C$_{10}$H$_{12}$O calc. % C, 81.04; % H, 8.16. found. % C, 80.25; % H, 8.20.

Analysis of this sample by chiral HPLC chromatography was carried out on Chiracel OD column (250+20)×4.6 mm, 10 μm, eluent: hexane (85% vol)-2-propanol (15% vol), flow rate 1.0 mL/min.: R$_t$ 8.86 min. (97.34%), R$^t$ 10.6 min. (1.48%); ee=97.00%.

Example 9

1-{(Z)-6-[(1R,2R,3R,5S)-2-((1R/1S, 3S)-3-Triethylsilyloxy-5-phenyl-1-(phenylsulfonyl)pentyl)-3,5-bis-(triethylsilyloxy)cyclopentyl]hex-4-enyl}-4-methyl-2,6,7-trioxabicyclo[2.2.2]octane and 2,2-bis(hydroxymethyl)propyl (Z)-7-((1R,2R,3R,5S)-2-((1R/1S,3S)-3-triethylsilyloxy-5-phenyl-1-(phenylsulfonyl)pentyl)-3,5-bis-(triethylsilyloxy)cyclopentyl]hept-5-enate

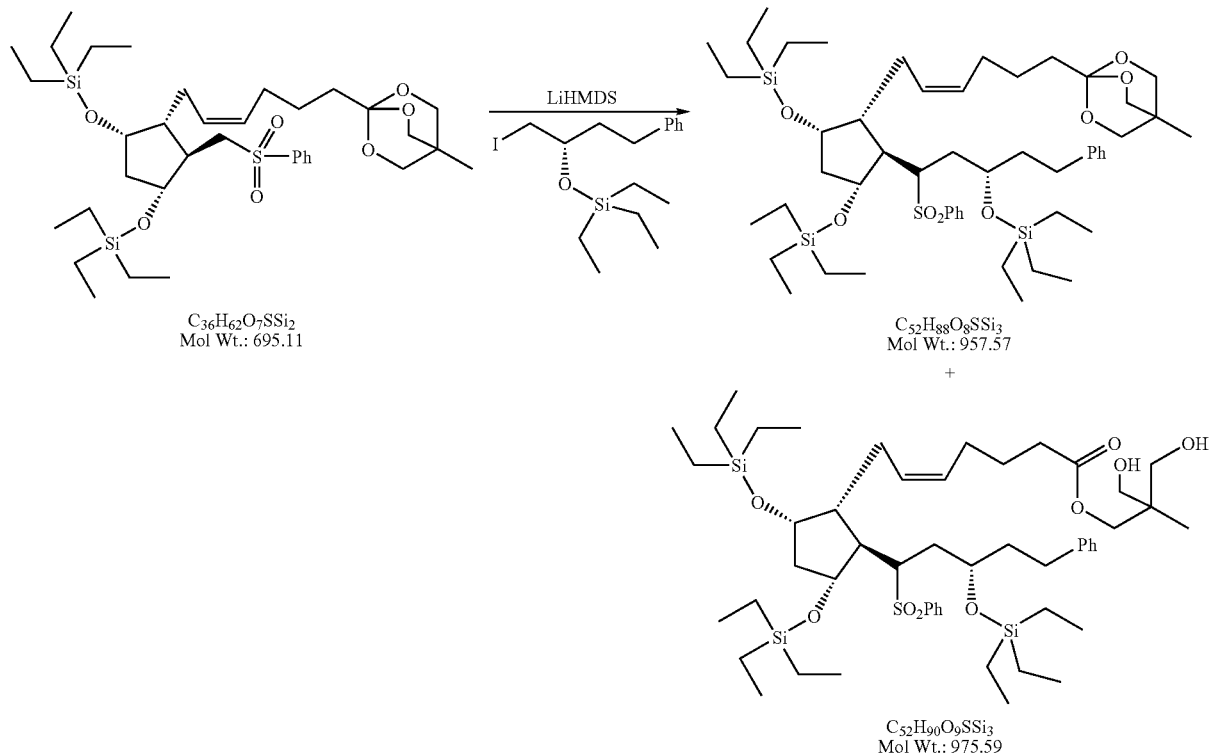

1-{(Z)-6-[(1R,2R,3R,5S)-2-((Phenylsulfonyl)methyl)-3,5-bis-(triethylsilyloxy)cyclopentyl]hex-4-enyl}-4-methyl-2,6,7-trioxabicyclo[2.2.2]octane (2.29 g, 3.29 mM) was dissolved in anhydrous THF (Aldrich, containing inhibitor); 15 mL). The solution was cooled to −75° C. under argon. Upon vigorous stirring, 1.0 M solution of lithium bis(trimethylsilyl)amide in THF (14 mL, 14 mM) was added over 3 minutes. It was stirred at −78° C. under argon (20 minutes), then the solution was heated to 0° C. and stirred at this temperature for 10 minutes, then the mixture was cooled again to −78° C. After 5 minutes of stirring at this temperature, the solution of (S)-1-phenyl-4-iodo-3-triethylsilyloxybutane (ee=99.2%, 4.96 g, 12.7 mM) in anhydrous THF (4 mL) was slowly added dropwise. It was stirred under argon at −78° C. for 10 minutes, then at 0° C. for 80 minutes. The cooling bath was removed and stirring was continued, allowing slow heating of the reaction mixture to +20° C. After the total reaction time of 5 hours and 10 minute, the reaction mixture was cooled again under argon to −78° C. and 1% solution of $C_5H_5N$ in the brine-saturated aqueous solution of $NaHCO_3$ mixture (1:1) (4 mL) was added dropwise, then the mixture of EtOAc-$CH_2Cl_2$ (6:1); 50 mL) was added and the cooling bath was exchanged for water bath (+101C). Upon stirring of flask content, 1% solution of $C_5H_5N$ in brine-saturated aqueous solution of $NaHCO_3$ mixture (1:1) (20 mL) was added. Then the mixture was transferred to the separator containing 1% solution of $C_5H_5N$ in saturated aqueous solution of $NaHCO_3$ mixture (1:1) (30 mL) and mixture of EtOAc-$CH_2Cl_2$ (6:1; 60 mL). After extraction, the phases were separated, the aqueous phase was extracted with EtOAc-$CH_2Cl_2$ mixture (6:1; 30 mL). The organic phases were combined and extracted with 1% solution of $C_5H_5N$ in brine-saturated aqueous solution of $NaHCO_3$ mixture (1:1) (50 mL). The phases were separated, the organic phase was dried over anhydrous $Na_2SO_4$ (15 g). The drying agent was filtered and washed with EttOAc (20 mL). The filtrates were combined, concentrated and dried (6.92 g, oil). This sample was separated by flash chromatography on silica gel column 230-400 mesh (250 g). As eluent, the following mixtures of solvents (phases) were subsequently used, I: 5% EtOAc in hexane+0.1% $C_5H_5N$, II: 10% EtOAc in hexane+0.1% $C_5H_5N$, III: 16.3% EtOAc in hexane+0.1% $C_5H_5N$, IV: 100% EtOAc+0.1% $C_5H_5N$. Concentration and drying of fractions pure on TLC eluted with Phase I gave (S)-1-phenyl-4-iodo-3-triethylsilylbutane (ee=99.2%; 3.757 g), $^1$H-NMR (CDCl$_3$; 200 MHz) identical with that described in Example 8d. 1; concentration and drying of fractions pure on TLC eluted with Phase III gave: (a) 1-{(Z)-6-[(1R,2R,3R,5S)-2-((1R/1S, 3S)-3-triethylsilyloxy-5-phenyl-1-(phenylsulfonyl)pentyl)-3,5-bis-(triethylsilyloxy)cyclopentyl]hex-4-enyl}-4-methyl-2,6,7-trioxabicyclo[2.2.2]octane (mixture of two epimers in a ratio of 5:2, of different configurations at carbon atom, to which phenylsulfonyl is attached) (1.456 g, 46.2%); elem. analysis: for $C_{52}H_{88}O_8SSi_3$ calc. % C, 65.22; % H, 9.26; % S, 3.35. found. % C, 65.58; % H, 9.37; % S, 3.55. Content of each isomer in this mixture was determined on the basis of integration of olefinic signals in ¹H-NMR spectrum (CDCl₃; 500 MHz); and (b) 1-{(Z)-6-[(1R,2R,3R,5S)-2-((phenylsulfonyl)methyl)-3,5-bis-(triethylsilyloxy)cyclopentyl]hex-4-enyl}-4-methyl-2,6,7-trioxabicyclo[2.2.2]octane (recovered substrate; 165 mg, 7.2%), colorless glaze; ¹H-NMR spectrum (CDCl₃; 200 MHz) identical with that described in Example 6; concentration and drying of fractions pure on TLC eluted with Phase IV allowed for preparation of (Z)-7-((1R,2R,3R,5S)-2-((1R/1S,3S)-3-triethylsilyloxy-5-phenyl-1-(phenylsulfonyl)pentyl)-3,5-bis-(triethylsilyloxy)-cyclopentyl]hept-5-enoic acid 2,2-bis(hydroxymethyl)propyl ester (mixture of two isomers in a ratio of approx. 5:2, of different configurations at carbon atom, to which phenylsulfonyl is attached) (435 mg, 13.5%), pale yellowish, thick oil; ¹H-NMR (CDCl₃+0.1% C₅D₅N; 200 MHz) δ 0.57 (18H, m), 0.83 (3H, s, CH₃), 0.94 (27H, m), 1.40-1.82 (5H, m), 1.90 (2H, m), 1.98-2.45 (10H, m), 3.10 (1H, bs, OH), 3.22 (0.29H, m), 3.47 (0.71H, m), 3.55 (4H, bs), 3.87 (1H, m), 3.89 (1H, bs), 4.18 (4H, m), 4.41 (0.29H, m), 4.53 (0.71H, m), 5.26-5.53 (2H, m), 7.08-7.33 (5H, m), 7.46-7.72 (3H, m), 7.84-7.94 (2H, m).

A sample of 1-{(Z)-6-[(1R,2R,3R,5S)-2-((1R/1S, 3S)-3-triethylsilyloxy-5-phenyl-1-(phenylsulfonyl)pentyl)-3,5-bis-(triethylsilyloxy)cyclopentyl]hex-4-enyl}-4-methyl-2,6,7-trioxabicyclo[2.2.2]octane (mixture of two isomers in a ratio of 5:2, 90 mg) was separated, by repeating twice a procedure on flash column LiChroprep (25-40 μm, 7 g), using 10% EtOAc in hexane+0.1% C₅H₅N as eluent. The following compounds were obtained: (a) major isomer 1-{(Z)-6-[(1R,2R,3R,5S)-2-((1R,3S)-3-triethylsilyloxy-5-phenyl-1-(phenylsulfonyl)pentyl)-3,5-bis-(triethylsilyloxy)cyclopentyl]hex-4-enylo}-4-methyl-2,6,7-trioxabicyclo[2.2.2]octane (27.6 mg), colorless, thick oil; ¹H-NMR (CDCl₃+1% C₅D₅N; 500 MHz) δ 0.572 (18H, m), 0.798 (3H, s), 0.940 (27H, m), 1.560 (4H, m), 1.654 (3H, m), 1.730 (2H, m), 1.992 (1H, m), 2.074-2.238 (5H, m), 2.362 (1H, ddd: 10.1, 8.2, 1.9 Hz), 2.494 (1H, ddd: 13.6, 11.0, 5.2 Hz), 2.584 (1H, ddd: 13.6, 11.0, 6.1 Hz), 3.471 (1H, ddd: 7.2, 5.2, 2.0 Hz; CHSO₂Ph), 3.898 (6H, s), 3.92 (1H, m, W=7.7 Hz), 4.168 (1H, m, W=8.2 Hz), 4.582 (1H, m, W=6.8 Hz), 5.402 (2H, m, W=15.7 Hz), 7.132 (2H, bd: 7.1 Hz), 7.181 (1H, bt: 7.3 Hz), 7.276 (2H, bt: 7.6 Hz), 7.532 (2H, bt: 7.8 Hz), 7.594 (1H, ddd: 7.4, 2.0, 1.6 Hz), 7.886 (2H, bdd: 7.2, 1.5 Hz). ¹³C-NMR (CDCl₃+1% C₅D₅N; 125 MHz) δ 4.96 (3C), 5.04 (3C), 5.22 (3C), 6.87 (6C), 6.93 (3C), 14.51, 23.21, 25.69, 27.24, 30.16, 31.11, 34.35, 36.30, 39.07, 44.14, 45.78, 50.44, 60.74, 69.04, 71.09, 72.52 (3C), 73.03, 109.02, 125.67, 128.22 (2C), 128.28 (2C), 128.37 (2C), 128.54, 128.91 (2C), 130.20, 133.10, 140.13, 142.17; and (b) minor isomer 1-{(Z)-6-[(1R,2R,3R,5S)-2-((1S,3S)-3-triethylsilyloxy-5-phenyl-1-(phenylsulfonyl)pentyl)-3,5-bis-(triethylsilyloxy)cyclopentyl]hex-4-enyl}-4-methyl-2,6,7-trioxabicyclo[2.2.2]octane (17.9 mg), colorless, thick oil; ¹H-NMR (CDCl₃+1% C₅D₅N; 500 MHz) δ 0.580 (18H, m), 0.783 (3H, s, CH₃), 0.950 (27H, m), 1.420-1.609 (6H, m), 1.677 (3H, m), 1.805 (1H, quintet 7.1 Hz), 1.924-2.374 (7H, m), 2.475 (1H, ddd: 13.8, 11.4, 4.8 Hz), 3.240 (1H, ddd: 7.0, 4.8, 1.9 Hz; CHSO₂Ph), 3.882 (6H, s), 3.896 (1H, m, W=24 Hz), 4.183 (1H, dd: 9.9, 5.1 Hz), 4.484 (1H, ddd: 12.6, 7.8, 5.9 Hz), 5.265 (2H, bdd: 5.0, 4.4 Hz), 7.027 (2H, dddd: 7.0, 2.2, 1.8, 1.4 Hz), 7.161 (1H, dd: 7.4, 1.4 Hz), 7.239 (2H, dddd: 7.4, 7.0, 2.2, 1.6 Hz), 7.494 (2H, dddd: 7.6, 7.1, 1.6, 1.2 Hz), 7.550 (1H, dd: 7.5, 1.3 Hz), 7.912 (2H, dddd: 7.1, 2.0, 1.5, 1.2 Hz). ¹³C-NMR (CDCl₃+1% C₅D₅N; 125 MHz) δ 4.97 (3C), 4.99 (3C), 5.05 (3C), 6.86 (3C), 6.92 (3C), 6.94 (3C), 14.53, 23.17, 25.70, 26.18, 27.07, 29.65, 30.16, 30.37 (quaternary C), 34.93, 36.29, 37.74, 43.57, 46.32, 51.51, 61.23, 69.49, 71.86, 72.53, 73.64, 109.05, 125.61, 128.13, 128.16 (2C), 128.19 (2C), 128.90 (2C), 128.92 (2C), 130.48, 133.31, 139.44, 142.10.

Example 9.a

1-{(Z)-6-[(1R,2R,3R,5S)-2-((Phenylsulfonyl)methyl)-3-hydroxy-5-(triethylsilyloxy)cyclopentyl]hex-4-enyl}-4-methyl-2,6,7-trioxabicyclo[2.2.2]octane

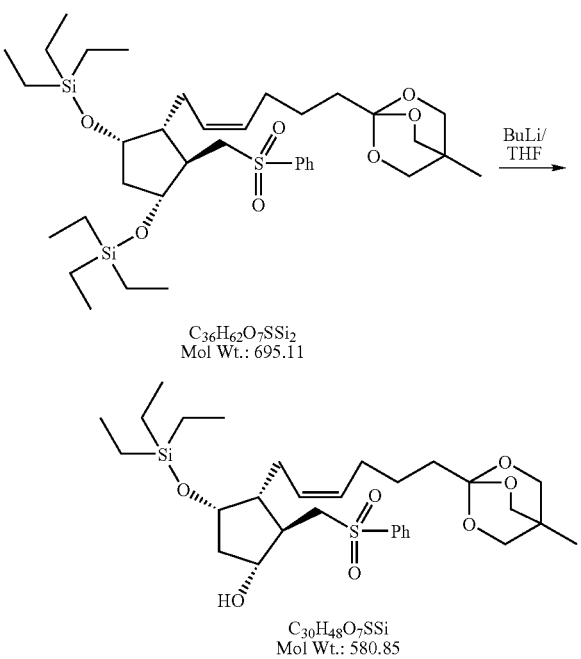

1-{(Z)-6-[(1R,2R,3R,5S)-2-((Phenylsulfonyl)methyl)-3,5-bis-(triethylsilyloxy)cyclopentylo]hex-4-enyl}-4-methyl-2,6,7-trioxabicyclo[2.2.2]octane (345 mg) was dissolved in anhydrous THF (2 mL). The solution was cooled to −78° C. and the solution of n-BuLi in hexane was added (2.4 M, 0.42 mL, 1.0 mM). After 1 hour of stirring at this temperature, solution of (S)-1-phenyl-4-iodo-3-triethylsilylbutane was added dropwise (ee=99.2%; 0.50 mL, approx. 0.62 g, 1.58 mM) in THF (0.50 mL). The mixture was stirred and slowly heated to room temperature over 2 hours. After processing similar to that of Example 9 above, the crude product was purified on chromatographic silica gel column 230-400 mesh (100 g), eluent gradient 10%-90% EtOAc in hexane+0.15% C₅H₅N. The following compounds were obtained: (a) unreacted alkyl iodide (532 mg) and (b) 1-{(Z)-6-[(1R,2R,3R,5S)-2-((phenylsulfonyl)methyl)-3-hydroxy-5-(triethylsilyloxy)cyclopentyl]hex-4-enyl}-4-methyl-2,6,7-trioxabicyclo[2.2.2]octane (139 mg, 48.2%), colorless glaze; ¹H-NMR (CDCl₃; 200 MHz) δ 0.60 (6H, q: 8.0 Hz), 0.80 (3H, s), 0.93 (9H, t: 8.0 Hz), 1.42 (3H, m), 1.60 (2H, m), 1.82 (4H, m), 1.97-2.23 (4H, m), 3.02 (1H, dd: 14.5, 11.0 Hz; CHSO₂Ph), 3.33 (1H, dd: 14.5, 2.6 Hz; CHSO₂Ph), 3.89 (6H, s), 4.12 (2H, m), 5.23 (2H, m), 7.60 (3H, m), 7.96 (2H, m). The second regioisomer (5-OH cyclopentane) of this compound was not isolated.

Example 10

1-{(Z)-6-[(1R,2R,3R,5S)-2-((R)-3-triethylsilyloxy-5-phenylpentyl)-3,5-bis-(triethylsilyloxy)cyclopentyl]hex-4-enyl}-4-methyl-2,6,7-trioxabicyclo[2.2.2]octane and 2,2-bis(hydroxymethyl)propyl (Z)-7-((1R,2R,3R,5S)-2-((R)-3-triethylsilyloxy-5-phenylpentyl)-3,5-bis-(triethylsilyloxy)cyclopentyl]hept-5-enate

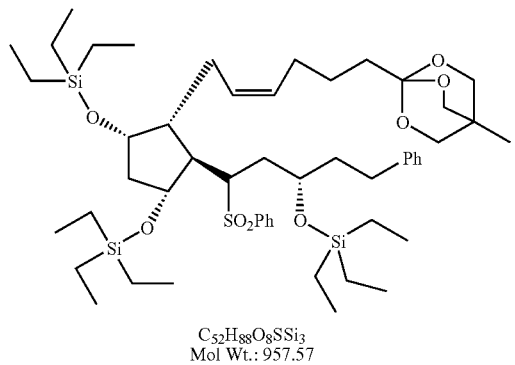

C₅₂H₈₈O₈SSi₃
Mol Wt.: 957.57

10% Na/Hg/
Na₂HPO₄ MeOH

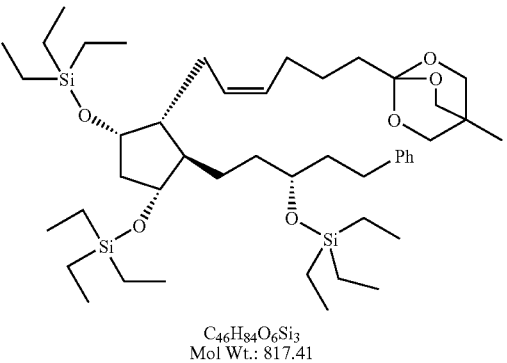

C₄₆H₈₄O₆Si₃
Mol Wt.: 817.41

+

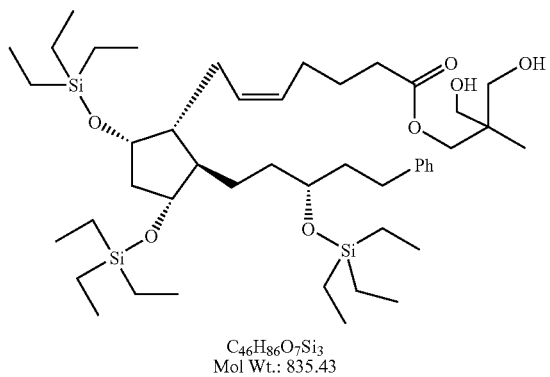

C₄₆H₈₆O₇Si₃
Mol Wt.: 835.43

1-{(Z)-6-[(1R,2R,3R,5S)-2-((1R/1S, 3S)-3-Triethylsilyloxy-5-phenyl-1-(phenylsulfonyl)pentyl)-3,5-bis-(triethylsilyloxy)cyclopentyl]hex-4-enyl}-4-methyl-2,6,7-trioxabicyclo[2.2.2]octane (the mixture of two epimers in a ratio of 5:2, of different configuration at C-1 carbon atom of omega chain) (770 mg, 0.80 mM) was dissolved in anhydrous MeOH (30 mL) and Na₂HPO₄ was added (1.00 g, 7.0 mM). The mixture was stirred in argon atmosphere at room temperature. After 10 minutes, the mixture was cooled under argon to 0° C. and 10% Na/Hg amalgam was added (2.86 g). The mixture was stirred at 0° C. for 1 hour, then the cooling bath was removed and stirring was carried out under argon, allowing the mixture to heat slowly to 20° C. After the total reaction time of 110 minutes, the mixture was cooled, vigorously stirring, again to 0° C. and, saturated aqueous solution of NH₄Cl (2.0 mL) was added dropwise. Immediately after the end of dropwise addition, 1% C₅H₅N solution in EtOAc (25 mL) was added. The mixture was vigorously stirred for 15 minutes, H₂O (5 mL) was added and stirring was carried out for further 10 minutes. Then the mixture was transferred to the separator containing saturated aqueous solution of NH₄Cl (40 mL) and 1% C₅H₅N solution in EtOAc (30 mL). Mercury was removed and secured. After extraction the phases were separated, the aqueous phase was extracted with EtOAc (30 mL), the organic phases were combined and dried over the anhydrous Na₂SO₄ (15 g, +4° C., over night). The drying agent was filtered and washed with EtOAc (15 mL). The combined filtrates were concentrated and dried under vacuum (5 mm Hg, 30 minutes, 25° C.). The crude product was purified by flash chromatography on LiChroprep column (25-40 μm; 70 g), eluent: gradient 7%-70% EtOAc in hexane+0.12% C₅H₅N.

After concentration and drying of homogenous fractions on TLC, the following compounds were obtained: (a) 1-{(Z)-6-[(1R,2R,3R,5S)-2-((R)-3-triethylsilyloxy-5-phenylpentyl)-3,5-bis-(triethylsilyloxy)cyclopentyl]hex-4-enyl}-4-methyl-2,6,7-trioxabicyclo[2.2.2]octane (420 mg, 69.6%), colorless glaze; $[\alpha]_D$=(+)10° (CHCl₃+0.1% Et₃N, 20° C., c=1); ¹H-NMR (CDCl₃+0.1% C₅H₅N; 200 MHz) δ 0.60 (18H, m), 0.79 (3H, s), 0.96 (27H, m), 1.30-1.61 (8H, m), 1.65-1.82 (5H, m), 2.01-2.32 (5H, m), 2.68 (2H, m), 3.73 (2H, m), 3.88 (6H, s), 4.09 (1H, bdd: 11.5, 5.8 Hz), 5.39 (2H, m, W=40 Hz), 7.20 (3H, m), 7.28 (2H, m); ¹³C-NMR (CDCl₃+0.1% C₅H₅N; 50 MHz) δ 4.87 (3C), 4.90 (3C), 5.09 (3C), 6.85 (3C), 6.86 (3C), 6.97 (3C), 14.49, 23.22, 25.74, 27.00, 27.93, 30.11, 31.66, 34.35, 36.21, 39.08, 44.19, 48.15, 50.10, 71.72, 72.34, 72.47 (3C), 76.23, 108.96, 125.51; 128.23 (2C), 128.26 (2C), 129.32, 129.71, 142.73; Elem. analysis: for C₄₆H₈₄O₆Si₃ calc. % C, 67.59; % H, 10.36. found. % C, 67.62; % H, 10.40; and (b) 2,2-bis(hydroxymethyl)propyl (Z)-7-((1R,2R,3R,5S)-2-((R)-3-triethylsilyloxy-5-phenylpentyl)-3,5-bis-(triethylsilyloxy)cyclopentyl]hept-5-enate (68 mg, 10.1%), pale yellowish glaze; TLC (Merck plates No. 1.05549; 25% EtOAc/hexane+0.1% C₅H₅N) $R_f$=0.07; ¹H-NMR (CDCl₃+0.1% C₅H₅N; 200 MHz) δ 0.58 (18H, 9×2H, q), 0.92 (30H, m: 9×3H, t+1×3H, s), 1.25-1.42 (2H, m), 1.43-1.90 (12H, m), 2.06-2.40 (6H, m), 2.64 (2H, m, W=60 Hz), 3.03 (1H, bs, OH), 3.54 (3H, m), 3.88 (2H, m), 4.04 (1H, m), 4.18 (2H, m), 5.40 (2H, m), 7.19 (3H, m), 7.27 (2H, m).

Example 11

1-{(Z)-6-[(1R,2R,3R,5S)-2-((R)-3-Triethylsilyloxy-5-phenylpentyl)-3,5-bis-(triethylsilyloxy)cyclopentyl]hex-4-enyl}-4-methyl-2,6,7-trioxabicylo[2.2.2]octane

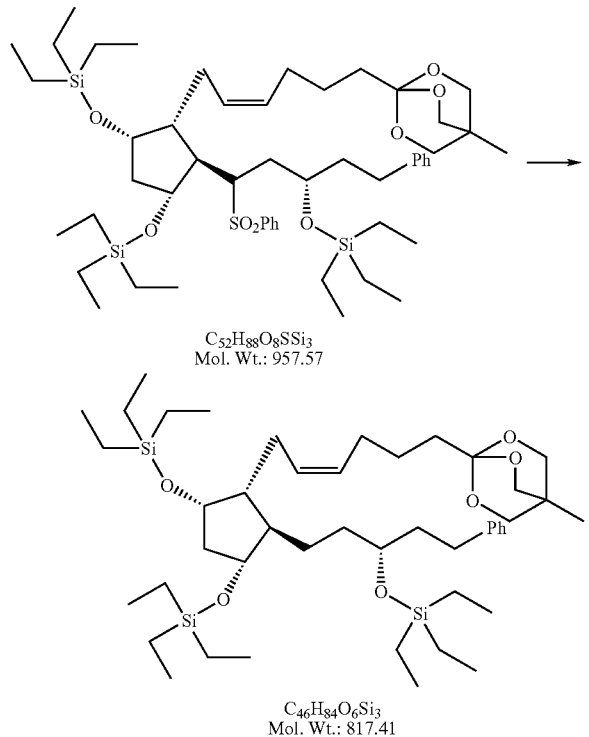

Example 11a

1-{(Z)-6-[(1R,2R,3R,5S)-2-((R)-3-Triethylsilyloxy-5-phenylpentyl)-3,5-bis-(triethylsilyloxy)cyclopentyl]hex-4-enyl}-4-methyl-2,6,7-trioxabicyclo[2.2.2]octane 1-{(Z)-6-[(1R,2R,3R,5S)-2-((1R/1S, 3S)-3-Triethylsilyloxy-5-phenyl-1-(phenylsulfonyl)pentyl)-3,5-bis-(triethylsilyloxy)cyclopentyl]hex-4-enyl}-4-methyl-2,6,7-trioxabicyclo[2.2.2]octane (the mixture of two epimers in a ratio of 5:2) (116 mg, 0.121 mM) was dissolved under argon in anhydrous MeOH (5.0 mL) and $Na_2HPO_4$ was added (150 mg, 1.06 mM). The mixture was stirred in argon atmosphere at room temperature. After 20 minutes, the mixture was cooled under argon to 0° C. and 10% Na/Hg amalgam was added (360 mg, approx. 1.5 mM of Na). The mixture was stirred at 0° C. for 1 hour, then the cooling bath was removed and stirring was carried out under argon, allowing the mixture to heat to 20° C. After the total reaction time of 100 minutes (starting from the moment of amalgam addition), the mixture was cooled again to 0° C. and, upon vigorous stirring, and saturated aqueous $NH_4Cl$ solution (3.0 mL) was added. The mixture was stirred for 10 minutes, then $H_2O$ (3 mL) was added and stirring was carried out under argon for 15 minutes. Then the mixture was transferred to the separator containing saturated aqueous $NH_4Cl$ solution (4 mL) and 1% solution of $C_5H_5N$ in EtOAc (40 mL). Mercury was removed and secured. After extraction, the phases were separated, the aqueous phase was extracted with EtOAc (30 mL), the organic phases were combined and extracted with saturated aqueous $NH_4Cl$ solution (30 mL). The layers were separated, the aqueous layer was dried over the anhydrous $Na_2SO_4$ (10 g, +4° C., over night). The drying agent was filtered and washed with EtOAc (10 mL).

The combined filtrates were concentrated and dried under vacuum (1 mm Hg, 40 minutes, 25° C.) to give 1-{(Z)-6-[(1R,2R,3R,5S)-2-((R)-3-triethylsilyloxy-5-phenylpentyl)-3,5-bis-(triethylsilyloxy)cyclopentyl]hex-4-enyl}-4-methyl-2,6,7-trioxabicyclo[2.2.2]octane (106 mg, 99%), pale yellowish glaze; $[\alpha]_D$=(+)9.9° ($CHCl_3$+0.1% $Et_3N$, 20° C., c=1); $^1$H-NMR ($CDCl_3$+0.1% $C_5H_5N$; 200 MHz): spectrum identical with that described for this compound in Example 10.

Example 11b

1-{(Z)-6-[(1R,2R,3R,5S)-2-((R)-3-Triethylsilyloxy-5-phenylpentyl)-3,5-bis-(triethylsilyloxy)cyclopentyl]hex-4-enyl}-4-methyl-2,6,7-trioxabicyclo[2.2.2]octane In a three-necked flask provided with a reflux condenser for dry ice and placed in a dry ice—methanol cooling bath in argon atmosphere, anhydrous $NH_3$ was condensed (Fluka; 50 mL). Then metallic calcium was added (20 mg, 5.5 mM), stirring was carried out for 25 minutes under argon, then the solution of 1-{(Z)-6-[(1R,2R,3R,5S)-2-((1R/1S,3S)-3-triethylsilyloxy-5-phenyl-1-(phenylsulfonyl)pentyl)-3,5-bis-(triethylsilyloxy)cyclopentyl]hex-4-enyl}-4-methyl-2,6,7-trioxabicyclo[2.2.2]octane was added (the mixture of two epimers in a ratio of 5:2) (80 mg, 0.0835 mM) in anhydrous THF (5 mL). The mixture was stirred at −78° C. for 5 hours, then THF was added (5 mL), the cooling bath was removed and stirring was carried out over night, allowing ammonia to evaporate slowly. After 16 hours, THF was added (20 mL), the mixture was cooled to 0° C. and saturated aqueous $NH_4Cl$ solution (5 mL) was slowly added dropwise. EtOAc (30 mL) and $NH_4Cl$ (30 mL) were added, phases were separated after the extraction. The aqueous phase was extracted again with EtOAc (10 mL), the organic phases were combined and extracted with saturated aqueous $NH_4Cl$ solution (25 mL). The organic phase was dried over $Na_2SO_4$ (7 g), the drying agent was filtered, the filtrate was concentrated under vacuum (1 mm Hg, 50° C., 1 hour). Pale yellowish glaze (64 mg) was obtained, which was purified by flash chromatography on silica gel column (10 g), eluent: gradient 5-50% EtOAc in hexane+0.1% $C_5H_5N$.

1-{(Z)-6-[(1R,2R,3R,5S)-2-((R)-3-Triethylsilyloxy-5-phenylpentyl)-3,5-bis-(triethylsilyloxy)cyclopentyl]hex-4-enyl}-4-methyl-2,6,7-trioxabicyclo[2.2.2]octane was obtained (35.8 mg, 52.4%), colorless glaze; $^1$H-NMR ($CDCl_3$+0.1% $C_5H_5N$; 200 MHz): spectrum in accordance with that described for this compound in Example 10, however, additional signals, indicating presence of unknown olefinic impurity, were observed (approx. 25% mol.): δ 5.71 (bs), 3.89 (s, OBO—$CH_2$), 0.79 (s, OBO—$CH_3$).

Example 11c

1-{(Z)-6-[(1R,2R,3R,5S)-2-((R)-3-Triethylsilyloxy-5-phenylpentyl)-3,5-bis-(triethylsilyloxy)cyclopentyl]hex-4-enyl}-4-methyl-2,6,7-trioxabicyclo[2.2.2]octane In a three-necked 100 mL flask provided with a reflux condenser for dry ice and placed in a dry ice—methanol cooling bath in argon atmosphere, anhydrous NH₃ was condensed (Fluka; 50 mL). Then metallic lithium was added (71 mg, 10.2 mM), stirring was carried out for 20 minutes under argon, then the solution of 1-{(Z)-6-[(1R,2R,3R,5S)-2-((1R/1S, 3S)-3-triethylsilyloxy-5-phenyl-1-(phenylsulfonyl)pentyl)-3,5-bis-(triethylsilyloxy)cyclopentyl]hex-4-enyl}-4-methyl-2,6,7-trioxabicyclo[2.2.2]octane was added (the mixture of two epimers in a ratio of 5:2) (92 mg, 0.095 mM) in anhydrous THF (5 mL). The mixture was stirred at −78° C. for 1 hour, then the cooling bath was removed and stirring was carried out, allowing ammonia to evaporate. After 3 hours, THF (5.5 mL) was added and anhydrous MeOH (0.90 mL) was slowly added dropwise. The mixture was left over night for slow ammonia evaporation. Then saturated aqueous NH₄Cl (30 mL) solution and EtOAc (40 mL) were added, the phases were separated after extraction. The aqueous phase was extracted again with EtOAc (10 mL), the organic phases were combined and extracted with saturated aqueous NH₄Cl solution (25 mL). The organic phase was dried over Na₂SO₄ (6 g), the drying agent was filtered; the filtrate was concentrated under vacuum (1 mm Hg, 30° C., 30 min.). 1-{(Z)-6-[(1R,2R,3R,5S)-2-((R)-3-triethylsilyloxy-5-phenylpentyl)-3,5-bis-(triethylsilyloxy)cyclopentyl]hex-4-enyl}-4-methyl-2,6,7-trioxabicyclo[2.2.2]octane was obtained as colourless, thick oil (73 mg); ¹H-NMR (CDCl₃+0.1% C₅H₅N; 200 MHz): spectrum in accordance with that described for this compound in Example 10; additional signals, indicating presence of unknown olefinic impurity, were observed (approx. 20% mol.): δ 5.71 (bs), 3.89 (s, OBO—CH₂), 0.79 (s, OBO—CH₃).

Example 11d

1-{(Z)-6-[(1R,2R,3R,5S)-2-((R)-3-Triethylsilyloxy-5-phenylpentyl)-3,5-bis-(triethylsilyloxy)cyclopentyl]hex-4-enyl}-4-methyl-2,6,7-trioxabicyclo[2.2.2]octane To a 100 mL flask, placed in the ice-water cooling bath, n-propylamine (Fluka, 20 mL) was added in argon atmosphere. Then metallic lithium was added (90 mg, 13 mM), stirring was carried out for 30 minutes under argon, then the solution of 1-{(Z)-6-[(1R,2R,3R,5S)-2-((1R/1S,3S)-3-triethylsilyloxy-5-phenyl-1-(phenylsulfonyl)pentyl)-3,5-bis-(triethylsilyloxy)cyclopentyl]hex-4-enyl}-4-methyl-2,6,7-trioxabicyclo[2.2.2]octane was added (the mixture of two epimers in a ratio of 5:2) (77 mg, 0.08 mM) in anhydrous THF (3 mL). Stirring was carried out at 0° C. for 4 hours, then the cooling bath was removed and stirring was carried out for 1 hour. THF (5.5 mL) was added and anhydrous MeOH (1 mL) was very slowly added dropwise. Stirring was carried out for 0.5 hour, then the mixture was concentrated under vacuum to approx. 7 mL, saturated aqueous NH₄Cl solution (30 mL) and EtOAc (40 mL) were added, the phases were separated after extraction. The aqueous phase was extracted again with EtOAc (10 mL), the organic phases were combined and extracted with saturated aqueous NH₄CL solution (25 mL). The organic phase was dried over Na₂SO₄ (6 g), the drying agent was filtered; the filtrate was concentrated under vacuum. (1 mm Hg, 30° C., 2 hrs). 1-{(Z)-6-[(1R,2R,3R,5S)-2-((R)-3-triethylsilyloxy-5-phenylpentyl)-3,5-bis-(triethylsilyloxy)cyclopentyl]hex-4-enyl}-4-methyl-2,6,7-trioxabicyclo[2.2.2]octane was obtained as pale yellowish, thick oil (59 mg); ¹H-NMR (CDCl₃+0.1% C₅H₅N; 200 MHz): spectrum in accordance with that described for this compound in Example 10; additional signals, indicating presence of unknown olephinic impurity, were observed (approx. 27% mol.): δ 5.71 (bs), 3.89 (s, OBO—CH₂), 0.79 (s, OBO—CH₃).

Example 12

1-{(Z)-6-[(1R,2R,3R,5S)-2-((1R/1S,3S)-3-triethylsilyloxy-5-phenyl-1-(phenylsulfonyl)pentyl)-3,5-bis-(triethylsilyloxy)cyclopentyl]hex-4-enyl}-4-methyl-2,6,7-trioxabicyclo[2.2.2]octane

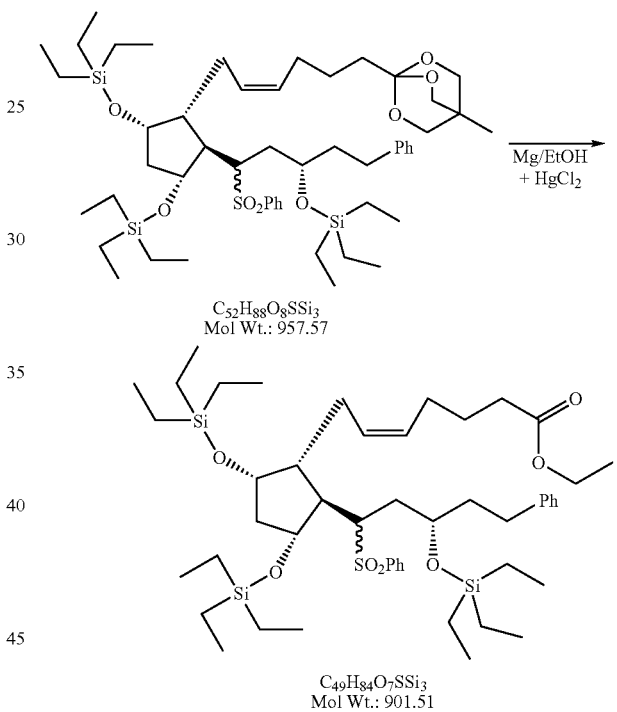

Example 12

1-{(Z)-6-[(1R,2R,3R,5S)-2-((1R/1S,3S)-3-triethylsilyloxy-5-phenyl-1-(phenylsulfonyl)pentyl)-3,5-bis-(triethylsilyloxy)cyclopentyl]hex-4-enyl}-4-methyl-2,6,7-trioxabicyclo[2.2.2]octane (the mixture of two epimers in a ratio of approx. 5:2) (82 mg, 0.856 mM) was dissolved under argon in anhydrous EtOH (0.50 mL). Mg was added (powder, 50 mesh; 12.7 mg. 0.52 mM) and HgCl₂ (3.1 mg). Stirring was carried out in a tightly closed flask for 48 hours. Then, C₅H₅N was added (0.3 mL) and the mixture was concentrated under vacuum nearly to dryness, then it was purified by flash chromatography on silica gel column 230-400 mesh, eluent: gradient 7%-18% EtOAc in hexane.

The following compounds were obtained: (a) (Z)-7-((1R, 2R,3R,5S)-2-((1R/1S,3S)-3-triethylsilyloxy-5-phenyl-1-(phenylsulfonyl)pentyl)-3,5-bis-(triethylsilyloxy)cyclopentyl]hept-5-enoic acid ethyl ester, 5:2 mixture, epimers at C-1 of omega chain (30.3 mg, 39.2%), colorless thick oil; TLC (Merck plates No. 1.05549; 10% EtOAc/hexane+0.1% $C_5H_5N$) $R_f$=0.38; $^1$H-NMR (CDCl$_3$+0.1% $C_5H_5N$; 200 MHz) δ 0.58 (18H, 9×2H, q), 0.92 (27H, m: 9×3H, t), 1.25 (3H, t: 7.3 Hz), 1.43-1.78 (5H, m), 1.90-2.36 (11H, m), 2.50 (2H, m, W=62 Hz), 3.23 (0.29H, m), 3.45 (0.71H, m), 3.90 (1H, m), 4.12 (2H, q: 7.2 Hz), 4.14 (1H, m), 4.48 (1H, ddd: 13.4, 7.8, 5.5 Hz), 5.40 (2H, m, W=47 Hz), 7.11 (2H, m), 7.23 (3H, m), 7.55 (3H, m), 7.87 (2H, bdd: 8.0, 1.5 Hz); and (b) 1-{(Z)-6-[(1R,2R,3R,5S)-2-((1R/1S,3S)-3-triethylsilyloxy-5-phenyl-1-(phenylsulfonyl)pentyl)-3,5-bis(triethylsilyloxy)cyclopentyl]hex-4-enyl}-4-methyl-2,6,7-trioxabicyclo[2.2.2]octane (the mixture of two epimers in a ratio of approx. 5:2) (34.9 mg, 42%; substrate recovery), thick, colorless oil, $^1$H-NMR spectrum identical with that described in Example 9.

Example 13

(Z)-7-{[(1R,2R,3R,5S)-3,5-Dihydroxy-2-((R)-3-hydroxy-5-phenylpentyl]cyclopentyl}hept-5-enoic acid

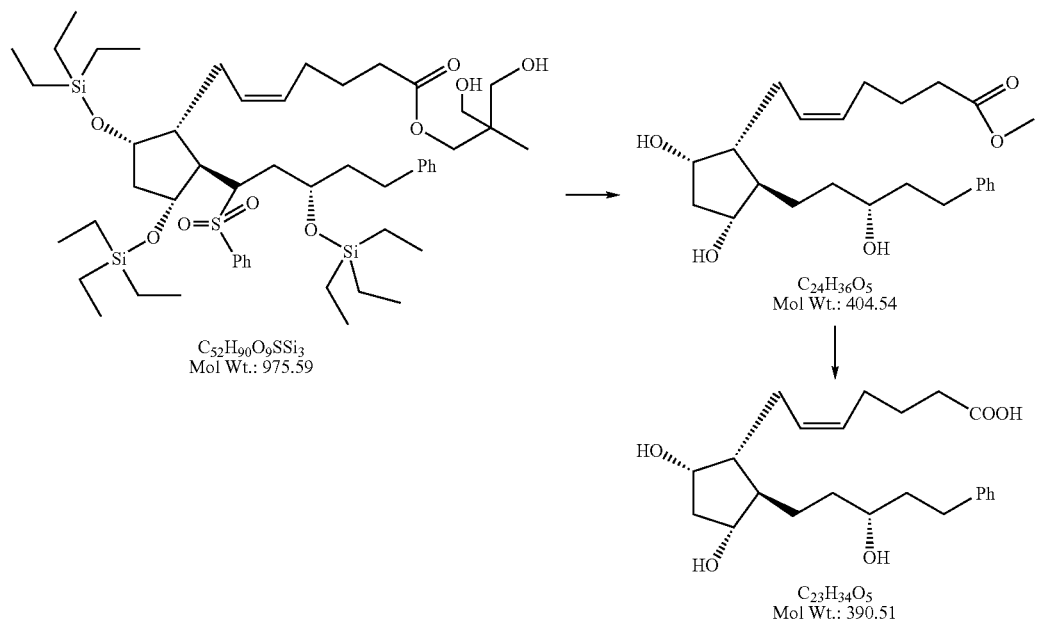

Example 13

(Z)-7-((1R,2R,3R,5S)-2-((1R/1S,3S)-3-triethylsilyloxy-5-phenyl-1-(phenylsulfonyl)pentyl)-3,5-bis-(triethylsilyloxy)cyclopentyl]hept-5-enoic acid 2,2-bis(hydroxymethyl)propyl ester (the mixture of two epimers in a ratio of approx. 5:2) (305 mg, 0.313 mM) was dissolved under argon in anhydrous MeOH (10 mL). The solution was stirred and Na$_2$HPO$_4$ was added (334 mg, 2.35 mM). Stirring was continued for 10 minutes, then the reaction mixture was cooled under argon to 0° C. and 10% Na(Hg) amalgam was added (956 mg). Stirring was carried out at 0° C. for 1 hour, then the cooling bath was removed and stirring was carried out while allowing the reaction mixture to heat slowly to 20° C. After the total reaction time of 120 minutes from the moment of amalgam addition, the mixture was cooled again to 0° C. and, upon vigorous stirring, saturated aqueous NH$_4$Cl solution (1 mL) was added dropwise. EtOAc (5 mL) and saturated aqueous solution of NH$_4$Cl (5 mL) were added, stirring was carried out for 15 minutes. Then H$_2$O was added (1.5 mL), stirring was carried out for 10 minutes, then the reaction mixture was transferred to the separator containing saturated aqueous NH$_4$Cl solution (20 mL) and EtOAc (10 mL). Mercury was removed and secured. The phases were separated after extraction; the aqueous phase was extracted with EtOAc (20 mL). The organic phases were combined and extracted with brine (30 mL). The organic layer was separated and dried over the anhydrous Na$_2$SO$_4$ (10 g), then the drying agent was filtered and washed on the filter with EtOAc (10 mL), the combined filtrates were concentrated and dried under vacuum. A colorless, thick oil was obtained (227 mg). This sample was dissolved in acetone (6 mL), then H$_2$O (0.9 mL) and PPTS (122 mg) were added. Stirring was carried out in argon atmosphere, at room temperature, for 6 hours. Then the reaction mixture was concentrated to approx. 1 mL, EtOAc (10 mL) and saturated aqueous NaHCO$_3$ solution (10 mL) were added. The phases were separated after extraction, saturated brine (25 mL) was added to the aqueous phase and two-time extraction with EtOAc was carried out (2×10 mL). The organic phases were combined and washed with saturated brine (25 mL). After separation of the layers, the organic layer was dried over anhydrous Na$_2$SO$_4$ (10 g). The drying agent was filtered and washed with EtOAc (5 mL). The combined filtrates were concentrated and dried under vacuum. Thick oil was obtained (177 mg), which was purified by chromatography on LiChroprep column (25-40µ; 9.0 g), eluent: 5% (vol) of MeOH in EtOAc. The fractions, which were pure on TLC, were combined, concentrated and dried under vacuum (1 mm Hg, 20° C., 2 hours).

(Z)-7-{[(1R,2R,3R,5S)-3,5-dihydroxy-2-((R)-3-hydroxy-5-phenylpentyl]cyclopentyl}hept-5-enoic acid methyl ester was obtained (45 mg, 36%), thick, colorless oil; $^1$H-NMR (CDCl$_3$; 200 MHz) δ 1.37 (2H, m), 1.50-1.81 (7H, m), 1.86

(2H, m, W=9 Hz), 1.97-2.40 (8H, m), 2.56-2.88 (3H, m), 3.66 (3H, s), 3.67 (1H, m, W=8 Hz), 3.95 (1H, m), 4.15 (1H, m), 5.42 (2H, m, W=45 Hz), 7.20 (3H, m), 7.27 (2H, m); $^{13}$C-NMR (CDCl$_3$; 50 MHz) δ 24.83, 26.61, 26.89, 29.62, 32.14, 33.41, 35.80, 39.05, 42.49, 51.64, 51.87, 52.80, 71.31, 74.65, 78.74, 125.83, 128.42 (4C), 129.45 (2C), 142.11, 174.46.

Sample of (Z)-7-{[(1R,2R,3R,5S)-3,5-dihydroxy-2-((R)-3-hydroxy-5-phenylpentyl]cyclopentyl}hept-5-enoic acid methyl ester (28 mg, 0.069 mM) was dissolved in MeOH (3 mL). H$_2$O (0.15 mL) and LiOH×1H$_2$O (60 mL, 1.43 mM) were added to the solution, stirred at room temperature, in argon atmosphere. After 20 hours, the reaction mixture was transferred to the separator containing saturated aqueous NH$_4$Cl solution (15 mL), 2M aqueous NaHSO$_4$ solution (10 mL) and EtOAc (15 mL). The phases were separated after extraction. 2M aqueous NaHSO$_4$ solution (5 mL) and EtOAc (10 mL) were added to the aqueous phase. The phases were separated after extraction. The organic phases were combined and extracted with the mixture of saturated aqueous NH$_4$Cl solution (10 mL) and 2M aqueous NaHSO$_4$ solution (5 mL). The organic phase was dried over Na$_2$SO$_4$ (5 g). The drying agent was filtered; the filtrate was concentrated and dried under vacuum (1 mm Hg, 25° C., 3 hours).

(Z)-7-{[(1R,2R,3R,5S)-3,5-dihydroxy-2-((R)-3-hydroxy-5-phenylpentyl]cyklopentyl}hept-5-enoic acid was obtained (26.0 mg, 96%) as pale yellowish glaze; [α]$_D$=(+)29.7° (MeOH, 20° C., c=1); $^1$H-NMR (CDCl$_3$+1% C$_5$D$_5$N; 200 MHz) δ 1.35 (2H, m), 1.45-1.86 (10H, m), 2.07-2.37 (7H, m), 2.71 (2H, m, W=61 Hz), 3.66 (1H, m), 3.94 (1H, m), 4.14 (1H, m), 4.94 (3H, bs), 5.43 (2H, m, W=60 Hz), 7.21 (5H, m).

Example 14

(Z)-7-{[(1R,2R,3R,5S)-3,5-Dihydroxy-2-((R)-3-hydroxy-5-phenylpentyl]cyclopentyl}hept-5-enoic acid 2,2-bis(hydroxymethyl)propyl ester lyloxy)cyclopentyl]hex-4-enyl}-4-methyl-2,6,7-trioxabicyclo[2.2.2]octane (378 mg, 0.462 mM) was dissolved in acetone (11 mL). The solution was stirred in argon atmosphere, H$_2$O was added (1.5 mL), then pyridinium p-toluenesulfonate (PPTS, 210 mg, 0.836 mM) was added. Stirring was carried out at the temperature of 18° C. for 5 hours, then the solution was concentrated to the volume of 1.5 mL, EtOAc (40 mL), brine (30 mL) and saturated aqueous solution of NaHCO$_3$ (20 mL) were added. The layers were separated after extraction; the aqueous layer was extracted twice with EtOAc (2×20 mL). The organic layers were combined and extracted with saturated brine (50 mL). The organic layer was dried over anhydrous Na$_2$SO$_4$ (7 g). The drying agent was filtered and washed with EtOAc (10 mL). The filtrates were combined, concentrated and dried under vacuum (1 mm Hg, 35° C., 1 hour). The prepared crude product was purified by flash chromatography on silica gel column 230-400 mesh (14 g), eluent: 5% MeOH/EtOAc. The fractions, which were pure on TLC, were concentrated and dried under vacuum do the constant mass.

(Z)-7-{[(1R,2R,3R,5S)-3,5-Dihydroxy-2-((R)-3-hydroxy-5-phenylpentyl]cyclopentyl}hept-5-enoic acid 2,2-bis(hydroxymethyl)propyl ester, colorless glaze was obtained (217 mg, 95%); [α]$_D$=(+)29.7° (CHCl$_3$, 20° C., c=1.8); $^1$H-NMR (CDCl$_3$; 200 MHz) δ 0.85 (3H, s), 1.36 (2H, m), 1.48-1.88 (1H, m), 2.02-2.39 (6H, m), 2.71 (2H, m, W=60 Hz), 3.42 (4H, bs), 3.55 (4H, s), 3.63 (1H, m), 3.95 (1H, m), 4.12 (2H, bs), 5.41 (2H, m, W=50 Hz), 7.18 (3H, m), 7.28 (2H, m); $^{13}$C-NMR (CDCl$_3$+1% C$_5$D$_5$N; 50 MHz) δ 16.88, 24.80, 26.52, 27.02, 29.61, 32.15, 33.54, 35.74, 39.05, 40.51, 42.51, 51.70, 52.63, 66.55, 67.00 (2C), 71.15, 74.53, 78.53, 125.78, 128.39 (2C), 128.42 (2C), 129.21, 129.77, 142.23, 174.56; HR ESI MS for C$_{28}$H$_{44}$O$_7$Na calc. (M+Na$^+$) m/z 515.29847, found. 515.2962.

Example 15

(Z)-7-{[(1R,2R,3R,5S)-3,5-Dihydroxy-2-((R)-3-hydroxy-5-phenylpentyl]cyclopentyl}hept-5-enoic acid

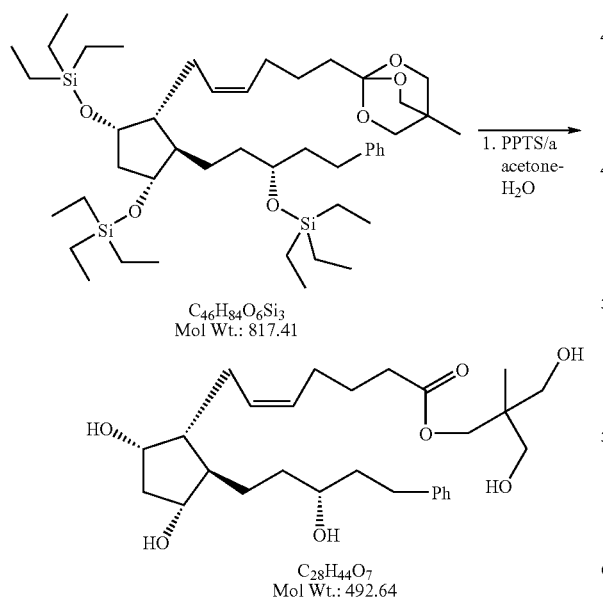

Example 14

1-{(Z)-6-[(1R,2R,3R,5S)-2-((1R/1S,3S)-3-Triethylsilyloxy-5-phenyl-1-(phenylsulfonyl)pentyl)-3,5-bis-(triethylsi-

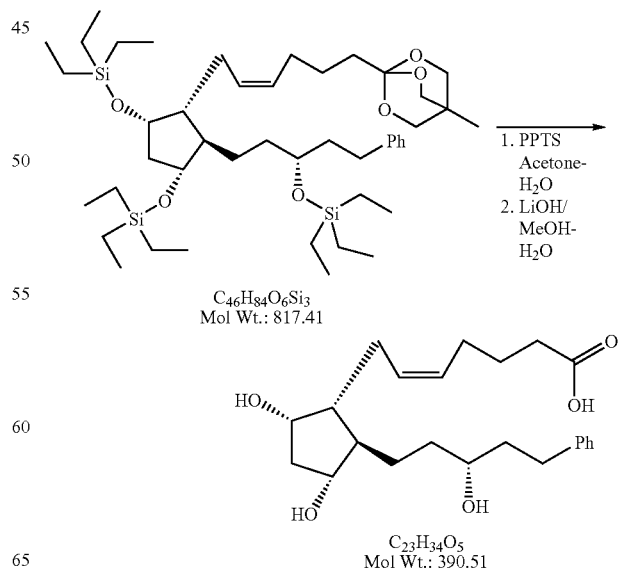

1-{(Z)-6-[(1R,2R,3R,5S)-2-((1R/1S, 3S)-3-Triethylsilyloxy-5-phenyl-1-(phenylsulfonyl)pentyl)-3,5-bis(triethylsilyloxy)cyclopentyl]hex-4-enyl}-4-methyl-2,6,7-rioxabicyclo[2.2.2]octane (99 mg, 0.121 mM) was dissolved in acetone (17 mL). The solution was stirred in argon atmosphere, $H_2O$ was added (1 mL), then pyridinium p-toluenesulfonate (PPTS, 77 mg) was added. Stirring was carried out at 18° C. for 16 hours, then the solution was concentrated to the volume of approx. 1 mL, MeOH (10 mL) and $H_2O$ were added. Stirring was carried out under argon at room temperature and LiOH×1$H_2O$ was added (320 mg, 7.62 mM). After 5.5 h, the mixture was transferred to the separator containing saturated aqueous $NH_4Cl$ solution (50 mL), 2M aqueous $NaHSO_4$ solution (15 mL) and EtOAc (45 mL). The phases were separated after extraction, 2M aqueous $NaHSO_4$ solution was added to the aqueous phase and extraction with EtOAc (30 mL) was carried out again. The organic phases were combined, dried over anhydrous $Na_2SO_4$ (12 g), the drying agent was filtered; the filtrate was concentrated and dried under vacuum. Pale yellowish glaze was obtained (62 mg). This sample was purified by flash chromatography on LiChroprep column (25-40 μm; 10 g), eluent: 0.5% AcOH in EtOAc. The fractions, which were pure on TLC, were combined, concentrated and dried under vacuum (1 mm Hg, 30° C., 2 hours) to the constant mass.

(Z)-7-{[(1R,2R,3R,5S)-3,5-Dihydroxy-2-((R)-3-hydroxy-5-phenylpentyl]cyclopentyl}hept-5-enoic acid was obtained (20.0 mg, 42.3%) as thick, colorless oil; $[\alpha]_D$=(+)30° (MeOH, 20° C., c=1); $^1$H-NMR (CDCl$_3$+1% C$_5$D$_5$N; 200 MHz) δ 1.35 (2H, m), 1.45-1.86 (10H, m), 2.07-2.37 (7H, m), 2.71 (2H, m, W=61 Hz), 3.66 (1H, m), 3.94 (1H, m), 4.14 (1H, m), 5.42 (2H, m, W=60 Hz), 5.70 (3H, bs), 7.21 (5H, m); $^{13}$C-NMR (CDCl$_3$+1% C$_5$D$_5$N; 50 MHz) δ 24.82, 26.50, 26.68, 29.23, 32.10, 33.49, 35.38, 38.86, 42.44, 51.62, 52.32, 71.33, 74.28, 78.42, 125.74, 128.35 (2C), 128.41 (2C), 129.44, 129.50, 142.21, 177.10; HR ESI MS for $C_{23}H_{34}O_5Na$ calc. (M+Na$^+$) m/z 413.23039, found. 413.2279.

Example 16

(Z)-7-{[(1R,2R,3R,5S)-3,5-Dihydroxy-2-((R)-3-hydroxy-5-phenylpentyl]cyclopentyl}hept-5-enoic acid

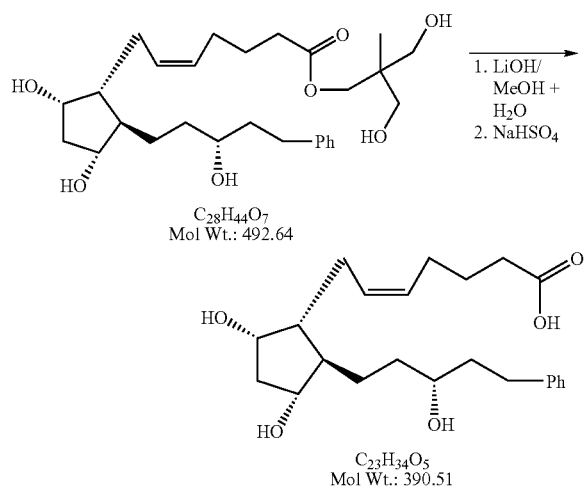

(Z)-7-{[(1R,2R,3R,5S)-3,5-Dihydroxy-2-((R)-3-hydroxy-5-phenylpentyl]cyclopentyl}hept-5-enoic acid 2,2-bis(hydroxymethyl)propyl ester, (120 mg, 0.243 mM) was dissolved in MeOH (5 mL). $H_2O$ was added (0.50 mL), the solution was stirred under argon at room temperature and LiOH×1$H_2O$ was added (240 mg, 5.72 mM). Stirring was carried out under argon for 8 hours; then the reaction mixture was quantitatively transferred to the separator containing saturated aqueous $NH_4Cl$ solution (50 mL), 2M aqueous $NaHSO_4$ solution (30 mL) and EtOAc (50 mL). The phases were separated after extraction; 2M aqueous $NaHSO_4$ solution (20 mL) and EtOAc (30 mL) were added to the aqueous phase. The phases were separated after extraction; the organic phases were combined and extracted with the mixture of saturated aqueous $NH_4Cl$ solution (20 mL) and 2M aqueous $NaHSO_4$ solution (10 mL). The organic phase was dried over $Na_2SO_2$ (10 g), the drying agent was filtered and washed with EtOAc (10 mL). The filtrates were combined, concentrated under vacuum (5 mm Hg, 30° C.) and dried under vacuum (1 mm Hg, 25° C., 3 hours).

(Z)-7-{[(1R,2R,3R,5S)-3,5-Dihydroksy-2-((R)-3-hydroksy-5-fenylopentylo]cyklopentylo}hept-5-enoic acid was obtained (94.1 mg, 99%) as thick, pale yellowish oil; $[\alpha]_D$=(+)29.7° (MeOH, 20° C., c=1); $^1$H-NMR (CDCl$_3$+1% C$_5$D$_5$N; 200 MHz) identical with that described for this compound in Example 15.

Example 17

(Z)-7-{[(1R,2R,3R,5S)-3,5-Dihydroxy-2-((R)-3-hydroxy-5-phenylpentyl]cyclopentyl}hept-5-enoic acid isopropyl ester

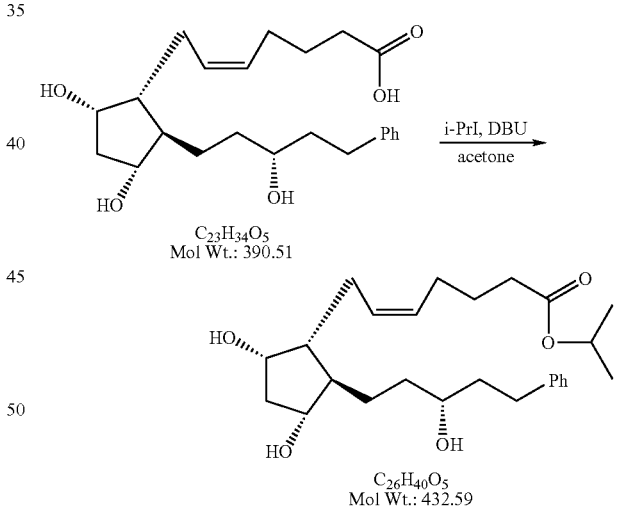

(Z)-7-{[(1R,2R,3R,5S)-3,5-dihydroxy-2-((R)-3-hydroxy-5-phenylpentyl]cyclopentyl}hept-5-enoic acid (20.0 mg, 0.051 mM) was dissolved in acetone (2.0 mL). The solution was stirred under argon for 10 minutes, then DBU was added (100 μL, 102 mg, 0.67 mM). After 3 minutes of stirring, 2-iodopropane was added (100 μL, 170 mg, 1.0 mM). The solution was stirred under argon at 20° C. for 14 hours. Then the reaction mixture was concentrated to the volume of approx. 0.50 mL, 4% aqueous citric acid solution (4 mL) and EtOAc (10 mL) were added. The mixture was quantitatively transferred to the separator containing EtOAc (20 mL), brine (30 mL) and 4% aqueous citric acid solution (2 mL). The layers were separated after extraction; the aqueous layer was extracted again with EtOAc (10 mL).

The organic layers were combined and extracted with the mixture of brine (20 mL) and saturated aqueous $NaHCO_3$ solution (20 mL). The organic layer was dried over $Na_2SO_4$ (7 g), the drying agent was filtered and washed on the filter with EtOAc (5 mL). The filtrates were combined, concentrated under vacuum (5 mm Hg, 30° C.) and dried under vacuum (1 mm Hg, 20° C., 1 hour). A colorless, thick oil was obtained (24 mg). This sample was purified by chromatography on LiChroprep column (25-40 µm; 4.0 g), eluent: 20% vol of hexane in EtOAc. The fractions, which were pure on TLC (Merck plates No. 1.05549, mobile phase: EtOAc-hexane 6:1) were combined, concentrated and dried under vacuum (1 mm Hg, 20° C., 4 hours, in darkness). The obtained product (91% HPLC purity) was purified by preparative HPLC (Example 17a).

(Z)-7-{[(1R,2R,3R,5S)-3,5-Dihydroxy-2-((R)-3-hydroxy-5-phenylpentyl]cyclopentyl}hept-5-enoic acid isopropyl ester (latanoprost) was obtained (14.0 mg, 63.2%) as thick, colorless oil; 99.83% HPLC purity; $[\alpha]_D$=(+) 32.5+/−0.5° ($CHCl_3$, 20° C., c=1); signals in spectra of $^1H$-NMR ($CDCl_3$; 500 MHz) and $^{13}C$-NMR ($CDCl_3$; 125 MHz): Table 1.

TABLE 1

Assignment of signals $^1H$-NMR ($CDCl_3$; 500 MHz) and $^{13}C$-NMR of latanoprost ($CDCl_3$; 125 MHz); based on DEPT, H,H-COSY 90, C,H-HETCOR and LR C,H-HETCOR spectra.

| Position | Signal $^{13}C$ [ppm] | Signals $^1H$ [ppm] |
|---|---|---|
| 1 | 173.45 | — |
| 2 | 34.05 | 2.278 (2H, t: 7.3 Hz) |
| 3 | 24.93 | 1.679 (2H, m) |
| 4 | 26.62 | 2.121 (2H, m, W = 42 Hz) |
| 5 | 129.56 | 5.390 (1H, m, W = 25 Hz) |
| 6 | 129.34 | 5.464 (1H, m, W = 25 Hz) |
| 7 | 26.90 | 2.216 (1H, m, W = 31.5 Hz); 2.332 (1H, m, W = 23.5 Hz) |
| 8 | 51.87 | 1.380 (1H, m, W = 30 Hz) |
| 9 | 74.67 | 4.159 (1H, bdd: 2.1, 1.9 Hz) |
| 10 | 42.52 | 1.864 (2H, dd: 4.4, 2.8 Hz) |
| 11 | 78.77 | 3.940 (1H, bdd: 5.4, 2.8 Hz) |
| 12 | 52.88 | 1.705 (1H, m, W = 20 Hz) |
| 13 | 29.63 | 1.339 (1H, m, W = 37 Hz), 1.524 (1H, m, W = 40 Hz) |
| 14 | 35.79 | 1.606 (1H, m, W = 30 Hz), 1.630 (1H, m, W = 20 Hz) |
| 15 | 71.29 | 3.660 (1H, m, W = 24 Hz) |
| 16 | 39.04 | 1.782 (2H, m, W = 45 Hz) |
| 17 | 32.11 | 2.675 (1H, ddd: 13.8, 9.4, 6.8 Hz), 2.798 (1H, ddd: 13.9, 9.4, 6.1 Hz) |
| 2-propyl (CH—O) | 67.63 | 4.997 (1H, h: 6.3 Hz) |
| 2-propyl (2 × $CH_3$) | 21.82 | 1.223 (6H, d: 6.3 Hz) |
| ipso | 142.09 | — |
| 2 × ortho | 128.38 | 7.201 (bd: 7.2 Hz) |
| 2 × meta | 128.38 | 7.279 (bt: 7.5 Hz) |
| para | 125.80 | 7.180 (bt: 7.3 Hz) |

HR ESI MS for $C_{26}H_{40}O_5Na$: calc. $(M+Na^+)$ m/z 455.27734, found 455.2756.

Example 17a

Synthesis of latanoprost according to the above procedure of Example 17 was repeated, starting from the appropriate acid (84 mg). The reaction was carried out over 5.5 h. After processing and purification on LiChroprep column (25-40 µm, 5.0 g; eluent: 20% vol of hexane in EtOAc). The fractions, which were pure on TLC (Merck plates No. 1.05549, mobile phase: EtOAc-hexane 6:1), were combined, concentrated and dried under vacuum. The product (59 mg) thus obtained was purified to the purity above 99.8% with use of preparative HPLC. After drying of isolated pure fraction under vacuum (1 mm Hg, 25° C., 4 hours), latanoprost was prepared (35 mg) as colorless, thick oil; 99.82% HPLC purity; $[\alpha]_D$=(+) 32°+/−0.5° ($CHCl_3$, 20° C., c=1); $^1H$-NMR ($CDCl_3$; 500 MHz): spectrum identical with that described in Example 17.

HPLC analyses of the prepared latanoprost samples were carried out on 4.0×250 mm column, Waters Spherisorb 5 µm Silica; UV detection (210 nm). As a mobile phase (flow rate 1 mL/min.), the following mixtures were used: (a) the mixture of hexane (91.50% vol), isopropanol (8.40% vol) and acetic acid (0.10% vol), retention time of latanoprost: 16.6 min., retention time of Impurity I: 15.4 min., of Impurity II: 18.8 min., or (b) the mixture of heptane (94% vol), $CH_3CN$ (2.5%) and isopropanol (3.5%), retention time of latanoprost: 18.8 min., retention time of Impurity I: 16.9 min., of Impurity II: 22.2 min.

Latanoprost samples, synthesized in the process according to the invention before purification by preparative HPLC were of purity (HPLC) approx. 91%, Impurity I: approx. 0.5-0.7%, Impurity II: approx. 5-8%.

Preparative purification of latanoprost samples was carried out on Waters RCM 40 mm set, 2 Nova-Pak 40×100 mm cartridges, (HR Silica, 6µ, 60 A), mobil phase (flow rate of 35 mL/min.): the mixture of hexane (91.50 vol), isopropanol (8.40% vol) and acetic acid (0.10% vol) or the mixture of heptane (94% vol), $CH_3CN$ (2.5%) and isopropanol (3.5%).

After purification by preparative HPLC (single), latanoprost of 99.83% purity (HPLC) was obtained.

As a result of preparative HPLC purification of consecutive batches of latanoprost, samples of Impurity I and Impurity II were isolated (HPLC data presented above).

Characteristics of Impurity I (data in accordance with B. Resul et al.; J. Med. Chem. 36 (1993), 243-248):

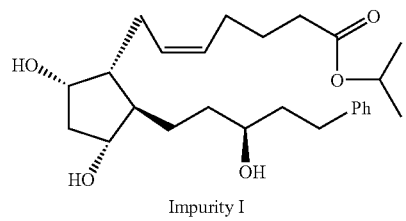

Impurity I

Impurity I: (Z)-7-{[(1R,2R,3R,5S)-3,5-dihydroxy-2-((S)-3-hydroxy-5-phenylpentyl]cyclopentyl}hept-5-enoic acid isopropyl ester $[\alpha]_D$=+34.3° ($CHCl_3$, 20° C., c=1); $^1H$— and $^{13}C$-NMR data: Table 2.

TABLE 2

Assignment of signals of Impurity I in $^1H$-NMR ($CDCl_3$; 500 MHz) and $^{13}C$-NMR ($CDCl_3$; 125 MHz) spectra; based on DEPT, H,H-COSY 90, C,H-HETCOR i LR C,H-HETCOR spectra.

| Position | $^{13}C$ [ppm] signal | $^1H$ [ppm] signals |
|---|---|---|
| 1 | 173.42 | — |
| 2 | 34.05 | 2.273 (2H, t: 7.3 Hz) |
| 3 | 24.92 | 1.683 (2H, bdd: 14.9, 7.4 Hz) |
| 4 | 26.59 | 2.116 (2H, bdd: 14.7, 7.4 Hz) |
| 5 | 129.39 | 5.374 (1H, m, W = 28 Hz) |

TABLE 2-continued

Assignment of signals of Impurity I in $^1$H-NMR (CDCl$_3$; 500 MHz) and $^{13}$C-NMR (CDCl$_3$; 125 MHz) spectra; based on DEPT, H,H-COSY 90, C,H-HETCOR i LR C,H-HETCOR spectra.

| Position | $^{13}$C [ppm] signal | $^1$H [ppm] signals |
|---|---|---|
| 6 | 129.43 | 5.476 (1H, m, W = 28 Hz) |
| 7 | 26.87 | 2.198 (1H, m, W = 32 Hz), 2.319 (1H, m, W = 35 Hz) |
| 8 | 51.91 | 1.353 (1H, ddd: 14.1, 9.1, 4.7 Hz) |
| 9 | 74.54 | 4.132 (1H, m, W = 17 Hz) |
| 10 | 42.41 | 1.861 (2H, m, W = 11 Hz) |
| 11 | 78.47 | 3.939 (1H, m, W = 17 Hz) |
| 12 | 52.51 | 1.726 (1H, m, W = 20 Hz) |
| 13 | 30.11 | 1.240 (1H, m, W = 30 Hz), 1.630 (1H, m, W = 30 Hz) |
| 14 | 35.71 | 1.561 (1H, m, W = 35 Hz), 1.630 (1H, m, W = 10 Hz) |
| 15 | 71.46 | 3.631 (1H, m, W = 28 Hz) |
| 16 | 39.26 | 1.779 (2H, m, W = 42 Hz) |
| 17 | 32.00 | 2.679 (1H, m, W = 40 Hz), 2.792 (1H, ddd: 14.0, 8.0, 4.5 Hz) |
| 2-propyl (CH—O) | 67.57 | 4.996 (1H, h: 6.3 Hz) |
| 2-propyl (2 × CH$_3$) | 21.80 | 1.221 (6H, d: 6.3 Hz) |
| ipso | 142.16 | — |
| 2 × ortho | 128.36 | 7.192 (2H, bd: 7.0 Hz) |
| 2 × meta | 128.33 | 7.270 (2H, bt: 7.5 Hz) |
| para | 125.72 | 7.173 (1H, bt: 7.3 Hz) |

HR ESI MS for $_{26}$H$_{40}$O$_5$Na: calc. (M+Na$^+$) m/z 455.27734, found. 455.2763.

Characteristics of Impurity II:.

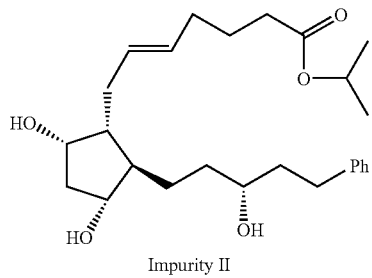

Impurity II

Impurity II: (E)-7-{[(1R,2R,3R,5S)-3,5-dihydroxy-2-((R)-3-hydroxy-5-phenylpentyl]cyclopentyl}hept-5-enoic acid isopropyl ester [α]$_D$=(+)21° (CHCl$_3$, 20° C., c=1); NMR data: Table 3.

TABLE 3

Assignment of signals of Impurity II in $^1$H-NMR (CDCl$_3$; 500 MHz) and $^{13}$C-NMR (CDCl$_3$; 125 MHz) spectra; based on DEPT, H,H-COSY 90, C,H-HETCOR i LR C,H-HETCOR spectra.

| Position | $^{13}$C [ppm] signal | $^1$H [ppm] signals |
|---|---|---|
| 1 | 173.25 | — |
| 2 | 34.01 | 2.258 (2H, dt: 15.2, 7.7 Hz) |
| 3 | 24.73 | 1.675 (2H, m, W = 35 Hz) |
| 4 | 31.86 | 2.026 (2H, m, W = 23 Hz) |
| 5 | 130.43 | 5.485 (1H, m, W = 14 Hz) |
| 6 | 129.99 | 5.485 (1H, m, W = 14 Hz) |
| 7 | 32.50 | 2.226 (1H, m, W = 40 Hz); 2.258 (1H, dd: 15.2, 7.7 Hz) |
| 8 | 51.70 | 1.405 (1H, m, W = 30 Hz) |

TABLE 3-continued

Assignment of signals of Impurity II in $^1$H-NMR (CDCl$_3$; 500 MHz) and $^{13}$C-NMR (CDCl$_3$; 125 MHz) spectra; based on DEPT, H,H-COSY 90, C,H-HETCOR i LR C,H-HETCOR spectra.

| Position | $^{13}$C [ppm] signal | $^1$H [ppm] signals |
|---|---|---|
| 9 | 74.95 | 4.188 (1H, m, W = 17 Hz) |
| 10 | 42.43 | 1.868 (2H, m, W = 10 Hz) |
| 11 | 78.86 | 3.937 (1H, m, W = 15 Hz) |
| 12 | 52.88 | 1.683 (1H, m, W = 30 Hz) |
| 13 | 29.65 | 1.325 (1H, m, W = 45 Hz) 1.506 (1H, m, W = 37 Hz) |
| 14 | 35.80 | 1.608 (2H, m, W = 27 Hz) |
| 15 | 71.34 | 3.668 (1H, bddd: 13.0, 5.6, 5.4 Hz) |
| 16 | 39.07 | 1.786 (2H, m, W = 48 Hz) |
| 17 | 32.13 | 2.676 (1H, ddd: 13.9, 9.2, 7.1 Hz); 2.796 (1H, ddd: 13.8, 9.3, 6.2 Hz) |
| 2-propyl (CH—O) | 67.49 | 5.001 (h: 6.3 Hz) |
| 2-propyl (2 × CH$_3$) | 21.85 | 1.137 (d: 6.3 Hz) |
| ipso | 142.04 | — |
| 2 × ortho | 128.39 | 7.203 (2H, bd: 7.1 Hz) |
| 2 × meta | 128.42 | 7.284 (2H, bt: 7.5 Hz) |
| para | 125.84 | 7.185 (1H, bt: 7.3 Hz) |

HR ESI MS for C$_{26}$H$_{40}$O$_5$Na: calc. (M+Na$^+$) m/z 455.27734, found. 455.2791.

Example 18

Preparation of latanoprost from (3aR,4R,5R,6aS)-hexahydro-5-triethylsilyloxy-4-[(R)-3-triethylsilyloxy-5-phenylpentyl]cyclopenta[b]furan-2-one

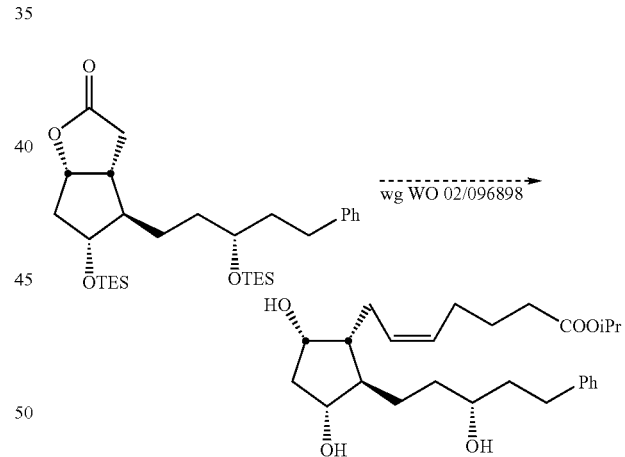

Latanoprost was prepared according to the procedure described in WO 02/096898, starting from (3aR,4R,5R,6aS)-hexahydro-5-triethylsilyloxy-4-[(R)-3-triethylsilyloxy-5-phenylpentyl]cyclopenta[b]furan-2-one. Latanoprost yield: 45-59% equivalent to (3aR,4R,5R,6aS)-hexahydro-5-triethylsilyloxy-4-[(R)-3-triethylsilyloxy-5-phenylpentyl]cyclopenta[b]furan-2-on. Latanoprost samples prepared in this way (70-94% purity, HPLC) were analyzed as in Example 17a. Presence of Impurity I, Impurity II and Impurity III was determined.

In the case of the use of mobile phase composed of heptane (94% vol), CH$_3$CN (2.5%), isopropanol (3.5%), latanoprost R$_t$: 18.9 min., Impurity I R$_t$: 17.1 min., Impurity II R$_t$: 23.1 min., Impurity III R$_t$: 31 min. Amount of impurities determined on the basis of integration at 210 nm: Impurity I (1.2-8.1%), Impurity II (1.3-4.6%), Impurity III (0.3-2.8%).

Preparative purification by HPLC, both in conditions of Example 17a of the present invention and in conditions described in WO 02/096898 A2, does not allow purification of latanoprost samples of Impurity I. For example, in the sample of Impurity I content=1.2%, its content after the first purification was 0.9%, whereas content of Impurity II and Impurity III was below 0.1%. Reduction of content of Impurity I to the level of below 0.1% required repeating of preparative resolution.

What is claimed is:

1. A process for the preparation of a 13,14-dihydro-PGF$_{2\alpha}$ derivative of the general formula (VIII) having an R or an S optical configuration at carbon 15

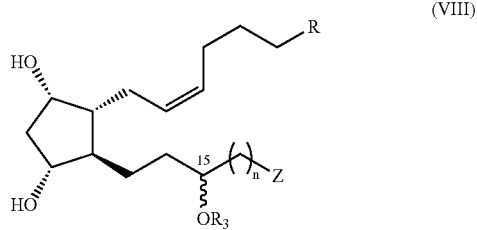

(VIII)

wherein:

R represents —COOH or —COOY;

Y is a $C_{1-6}$-alkyl, an alkylphenyl or a phenyl, optionally substituted by $C_{1-3}$-alkyl;

Z represents H, a methyl or a phenyl, optionally substituted by a $C_{1-3}$-alkyl, a $C_{1-3}$-alkoxy or at least one halogen atom;

$R_3$ represents H or a hydroxyl protecting group, and n represents an integer from 0 to 6;

the process comprising the steps of:

(a) generating an anion of the sulfone of formula (V) at the α position in relation to the sulfonyl group

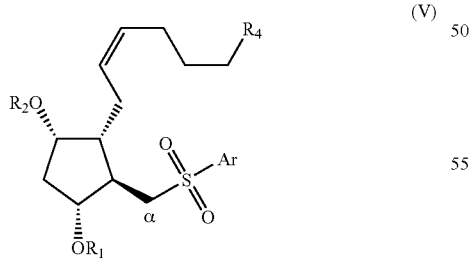

(V)

wherein $R_1$ and $R_2$, independently, represent a hydroxyl protecting group;

Ar represents a substituted or an unsubstituted aryl or heteroaryl containing at least one heteroatom selected from the group consisting of O, N, P and S atoms;

$R_4$ is an orthoester group represented by the general formula —C(OR$_6$)$_3$ or by the general formula (Va),

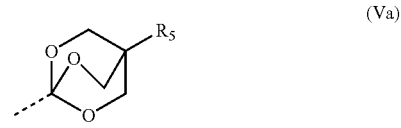

(Va)

$R_5$ represents H, a substituted or an unsubstituted $C_1$-$C_6$-alkyl or Ar; and $R_6$ is a substituted or an unsubstituted $C_1$-$C_{10}$-alkyl or Ar;

(b) reacting the anion generated in step (a) with an alkylating agent of the general formula (VI),

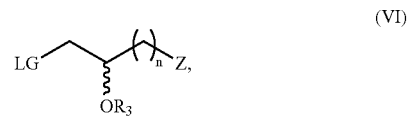

(VI)

to yield a compound of the general formula (VII)

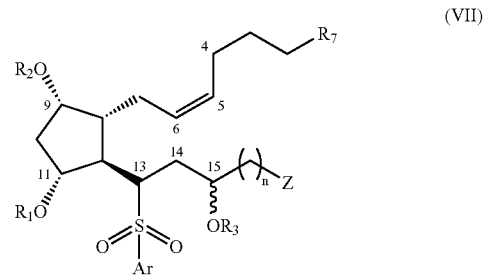

(VII)

wherein

LG represents a leaving group, and $R_3$ represents a hydroxyl protecting group; or LG and $R_3$ represent a chemical bond and/or taken together with the atoms to which they are attached and with an —S(O)— or an —SO$_2$— group form a cyclosulfite or a cyclosulfate; or LG and $R_3$ represent chemical bonds and/or taken together with the atoms to which they are attached form an epoxide;

$R_7$ is —C(=O)—OR$_8$, —CH$_2$—C(CH$_2$OH)$_2$—R$_5$, or an orthoester group represented by the general formula —C(OR$_6$)$_3$ or by the general formula (Va),

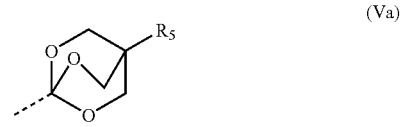

(Va)

$R_5$ represents H, substituted or unsubstituted $C_1$-$C_6$-alkyl or Ar; and $R_6$ is substituted or unsubstituted $C_1$-$C_{10}$-alkyl or aryl;

$R_8$ represents H, substituted or unsubstituted $C_{1-10}$-alkyl or phenyl;

Z represents H, methyl or phenyl, optionally substituted by $C_{1-3}$-alkyl, $C_{1-3}$-alkoxy or at least one halogen atom;

n represents an integer from 0 to 6;

$R_1$ and $R_2$, independently, represent a hydroxyl protecting group; and

Ar represents a substituted or an unsubstituted aryl or heteroaryl containing at least one heteroatom selected from the group consisting of O, N, P and S atoms;

(c) performing a reductive desulfonation of the compound of the general formula (VII) obtained in step (b) to yield the compound of the general formula (VIIa)

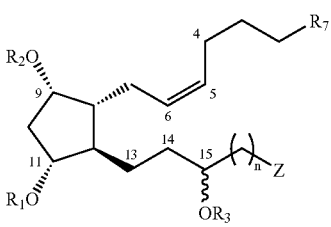

(VIIa)

wherein $R_1$, $R_2$ and $R_3$, independently, represent a hydroxyl protecting group;

$R_7$ is —C(=O)—$OR_8$, —$CH_2$—C($CH_2OH$)$_2$—$R_5$, or an orthoester group represented by the general formula —C($OR_6$)$_3$ or by the general formula (Va),

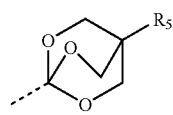

(Va)

$R_5$ represents H, substituted or unsubstituted $C_1$-$C_6$-alkyl or Ar; and $R_6$ is substituted or unsubstituted $C_1$-$C_{10}$-alkyl or aryl;

$R_8$ represents H, substituted or unsubstituted $C_{1-10}$-alkyl or phenyl;

Ar represents substituted or unsubstituted aryl or heteroaryl containing at least one heteroatom selected from the group consisting of O, N, P and S atoms;

n represents an integer from 0 to 6; and

Z represents H, methyl or phenyl, optionally substituted by $C_{1-3}$-alkyl, $C_{1-3}$-alkoxy or at least one halogen atom;

(d) removing the hydroxyl protecting groups from the compound of the general formula (VIIa) to yield the compound of formula (VIIb)

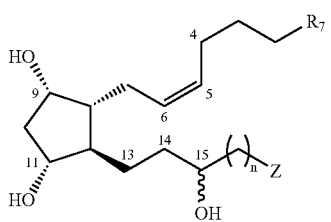

(VIIb)

wherein $R_7$ is —C(=O)—$OR_8$, —$CH_2$—C($CH_2OH$)$_2$—$R_5$, or an orthoester group represented by the general formula —C($OR_6$)$_3$ or by the general formula (Va),

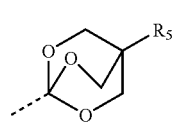

(Va)

$R_5$ represents H, substituted or unsubstituted $C_1$-$C_6$-alkyl or Ar; and $R_6$ is substituted or unsubstituted $C_1$-$C_{10}$-alkyl or aryl;

$R_8$ represents H, substituted or unsubstituted $C_{1-10}$-alkyl or phenyl;

Ar represents substituted or unsubstituted aryl or heteroaryl containing at least one heteroatom selected from the group consisting of O, N, P and S atoms;

n represents an integer from 0 to 6; and

Z represents H, methyl or phenyl, optionally substituted by $C_{1-3}$-alkyl, $C_{1-3}$-alkoxy or at least one halogen atom; and (e) converting the compound of formula (VIIb) obtained in step (d) to a compound of the general formula (VIII);

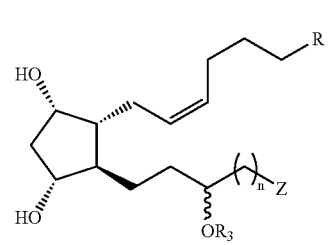

(VIII)

wherein

R represents COOH;

$R_3$ represents H;

n represents an integer from 0 to 6; and

Z represents H, methyl or phenyl, optionally substituted by $C_{1-3}$-alkyl, $C_{1-3}$-alkoxy or at least one halogen atom.

2. The process of claim 1 wherein the chiral configuration at the $R_3$O— substituted carbon of the alkylating agent corresponds to the chiral configuration at carbon 15 of the 13,14-dihydro-PGF$_{2\alpha}$ derivative of the general formula (VIII).

3. The process of claim 1 further comprising step (f): esterifying the compound of formula (VIII) obtained at step (e) to yield the compound of formula (VIII),

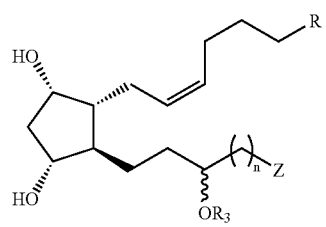

wherein

R represents COOY;

$R_3$ represents H;

Y is a $C_{1-6}$-alkyl, an alkylphenyl or a phenyl, optionally substituted by a $C_{1-3}$-alkyl;

Z represents H, a methyl or a phenyl, optionally substituted by a $C_{1-3}$-alkyl or a $C_{1-3}$-alkoxy or at least one halogen atom; and n represents an integer from 0 to 6.

4. The process of claim 1, wherein in step (a) generating an anion of the sulfone of formula (V) in situ by means of an organic base.

5. The process of claim 4, wherein said organic base is a bis(trimethylsilyl)amide of an alkaline metal.

6. The process of claim 5, wherein said organic base is lithium bis(trimethyl silyl)amide.

7. The process of claim 1, wherein
said alkylating agent is a compound of the general formula (VI)

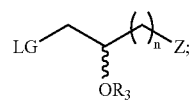

(VI)

LG represents a halogen, an alkylsulfonyloxy, an arylsulfonyloxy or an alkylarylsulfonyloxy group, and $R_3$ represents a hydroxyl protecting group; or LG and $R_3$ represent a chemical bond and/or taken together with the atoms to which they are attached and with an —S(O)— or an —SO$_2$— group form a cyclosulfite or a cyclosulfate; or LG and $R_3$ represent chemical bonds and/or taken together with the atoms to which they are attached form an epoxide;

Z represents H, a methyl or a phenyl, optionally substituted by a $C_{1-3}$-alkyl, a $C_{1-3}$-alkoxy or at least one halogen atom;

n represents an integer from 0 to 6; and the enantiomeric excess of said alkylating agent is greater than 99%.

8. The process of claim 1, wherein the reductive desulfonation in step (c) is carried out with sodium amalgam.

9. The process of claim 1, wherein the diastereoisomeric excess of the 13,14-dihydro-PGF$_{2\alpha}$ derivative of the general formula (VIII) is greater than 99%.

10. The process of claim 1, wherein the diastereoisomeric excess of the 13,14-dihydro-PGF$_{2\alpha}$ derivative of the general formula (VIII) is greater than 99.5%.

11. The process of claim 1, wherein the 13,14-dihydro-PGF$_{2\alpha}$ derivative of the general formula (VIII) is 13,14-dihydro-15(R)-17-phenyl-18,19,20-trinor-PGF$_{2\alpha}$.

12. The process of claim 11, wherein the diastereoisomeric excess of the 13,14-dihydro-15(R)-17-phenyl-18,19,20-trinor-PGF$_{2\alpha}$ is greater than 99%.

13. The process of claim 11, wherein the diastereoisomeric excess of the 13,14-dihydro-15(R)-17-phenyl-18,19,20-trinor-PGF$_{2\alpha}$ is greater than 99.5%.

14. A compound of the general formula (V)

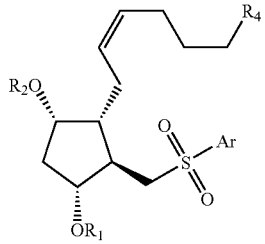

(V)

wherein $R_1$ and $R_2$, independently, represent H or a hydroxyl protecting group;

Ar represents a substituted or an unsubstituted aryl or heteroaryl containing at least one heteroatom selected from the group consisting of O, N, P and S atoms;

$R_4$ is an orthoester represented by the general formula —C(OR$_6$)$_3$ or by the general formula (Va),

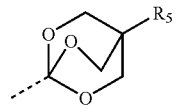

(Va)

$R_5$ represents H, substituted or unsubstituted $C_1$-$C_6$-alkyl or an Ar; and $R_6$ is a substituted or an unsubstituted $C_1$-$C_{10}$-alkyl, or Ar.

15. A process for the preparation of a compound of claim 14 comprising the steps of (a) converting a derivative of Corey (−)-lactone of the general formula (I) to a sulfide of the general formula (II)

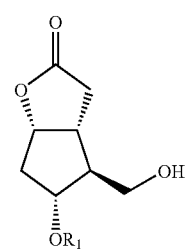

(I)

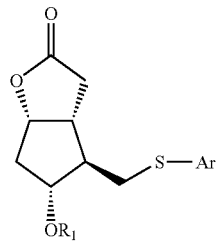

(II)

wherein $R_1$ represents H or a hydroxyl protecting group; and

Ar represents a substituted or an unsubstituted aryl or heteroaryl containing at least one heteroatom selected from the group consisting of O, N, P and S atoms;

(b) selectively oxidizing the sulfide of the general formula (II) to a sulfone of the general formula (III);

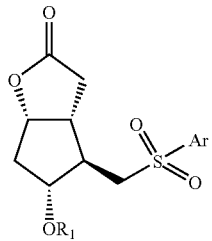
(III)

wherein
- $R_1$ represents H or a hydroxyl protecting group; and
- Ar represents a substituted or an unsubstituted aryl or heteroaryl containing at least one heteroatom selected from the group consisting of O, N, P and S atoms;

(c) reducing the carbonyl group of sulfone of formula (III) and isolating the derivative of lactol of formula (IV) having a desired chiral configuration at the reduced carbon

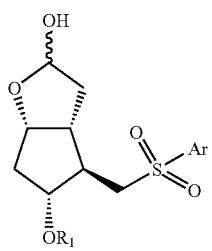
(IV)

wherein
- $R_1$ represents H or a hydroxyl protecting group; and
- Ar represents a substituted or an unsubstituted aryl or heteroaryl containing at least one heteroatom selected from the group consisting of O, N, P and S atoms;

(d) reacting the lactol of formula (IV) in a Wittig reaction with a precursor of the alpha side chain of the target prostaglandin to yield a compound of the general formula (V)

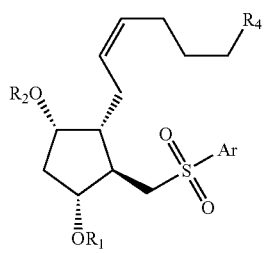
(V)

wherein
- $R_1$ represents H or a hydroxyl protecting group;
- $R_2$ represents H;
- Ar represents a substituted or an unsubstituted aryl or heteroaryl containing at least one heteroatom selected from the group consisting of O, N, P and S atoms;

$R_4$ is an orthoester represented by the general formula —$C(OR_6)_3$ or by the general formula (Va),

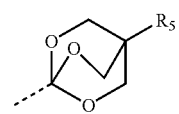
(Va)

$R_5$ represents H, substituted or unsubstituted $C_1$-$C_6$-alkyl or Ar; and
$R_6$ is a substituted or an unsubstituted $C_1$-$C_{10}$-alkyl or Ar.

16. The process of claim 15 comprising further (e) isolating the compound of the general formula (V), and (f) optionally, protecting the hydroxyl group —$OR_2$.

17. The process of claim 15 wherein magnesium monoperoxyphtalate is used as an oxidizing agent for selectively oxidizing the sulfide of the general formula (II) in step (b).

18. The process of claim 15 wherein step (b) is carried out in a biphasic solvent system of two or more non-miscible solvents at a temperature range of 0-40° C.

19. The process of claim 18 wherein the two or more non-miscible solvents are water and methylene chloride.

20. The process of claim 15 wherein step (d) is carried out in the presence of an organoaluminum compound.

21. The process of claim 20 wherein step (d) is carried out in the presence of Al(t-BuO)$_3$.

22. A compound of the general formula (VII)

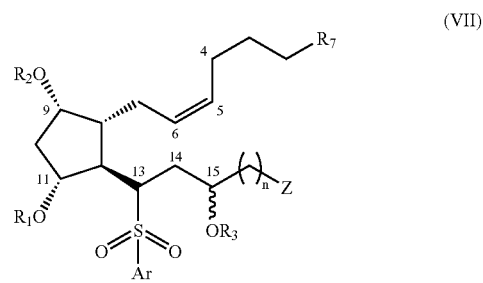
(VII)

wherein
- $R_1$, $R_2$ and $R_3$, independently, represent a hydroxyl protecting group;
- $R_7$ is —C(=O)—$OR_8$, —$CH_2$—$C(CH_2OH)_2$—$R_5$, or an orthoester group represented by the general formula —$C(OR_6)_3$ or by the general formula (Va),

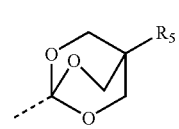
(Va)

$R_5$ represents H, substituted or unsubstituted $C_1$-$C_6$-alkyl or Ar; and
$R_6$ is a substituted or an unsubstituted $C_1$-$C_{10}$-alkyl or Ar;
$R_8$ represents H, a substituted or an unsubstituted $C_{1-10}$-alkyl, phenyl, or —$CH_2$—C—$(CH_2OH)_2$—$R_5$;
Z represents H, methyl or phenyl, optionally substituted by $C_{1-3}$-alkyl, $C_{1-3}$-alkoxy or at least one halogen atom;
n represents an integer from 0 to 6;

Ar represents substituted or unsubstituted aryl or heteroaryl containing at least one heteroatom selected from the group consisting of O, N, P and S atoms; and the compound has an R or S chiral configuration at the carbon atom substituted by —OR$_3$.

23. A compound of the general formula (VIIa)

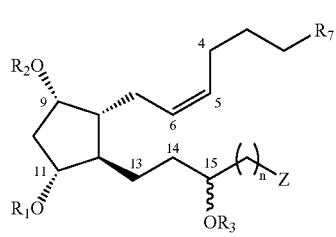
(VIIa)

wherein
R$_1$, R$_2$ and R$_3$, independently, represent H or a hydroxyl protecting group;
R$_7$ is —C(=O)—OR$_8$, or an orthoester group represented by the general formula —C(OR$_6$)$_3$ or by the general formula (Va),

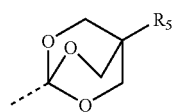
(Va)

R$_5$ represents H, substituted or unsubstituted C$_1$-C$_6$-alkyl or Ar; and
R$_6$ is substituted or unsubstituted C$_1$-C$_{10}$-alkyl or Ar;
R$_8$ represents —CH$_2$—C(CH$_2$OH)$_2$—R$_5$ group;
n represents an integer from 0 to 6;

Ar represents substituted or unsubstituted aryl or heteroaryl containing at least one heteroatom selected from the group consisting of O, N, P and S atoms;
Z represents H, methyl or phenyl, optionally substituted by C$_{1-3}$-alkyl, C$_{1-3}$-alkoxy or at least one halogen atom; and
the compound has an R or S chiral configuration at the carbon atom substituted by —OR$_3$.

24. A compound of claim 23 wherein the compound is

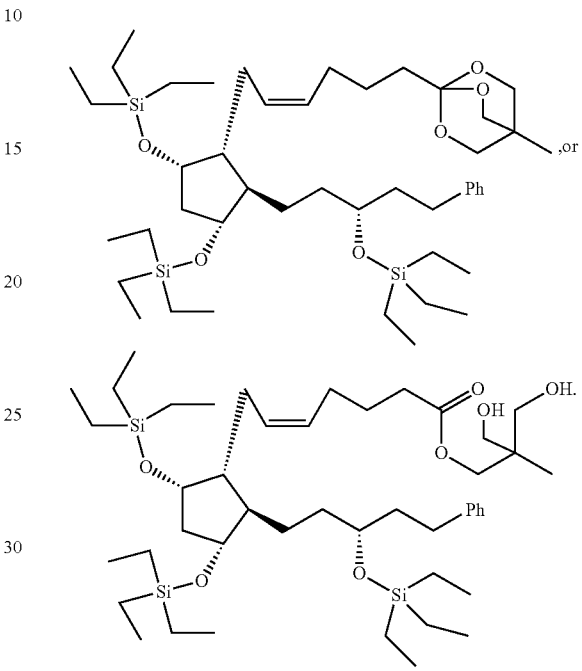

* * * * *